US012727798B2

(12) United States Patent
Fernando et al.

(10) Patent No.: US 12,727,798 B2
(45) Date of Patent: Sep. 8, 2026

(54) EAR-WEARABLE OXYGEN MONITORING SYSTEM

(71) Applicant: OXIWEAR, INC., Arlington, VA (US)

(72) Inventors: Shavini Fernando, Arlington, VA (US); George Donald Beckstein, III, Buffalo, NY (US); Ben Salthouse, San Francisco, CA (US); Keeline Wilcox, Arlington, VA (US)

(73) Assignee: OXIWEAR, INC., Arlington, VA (US)

(*) Notice: Subject to any disclaimer, the term of this patent is extended or adjusted under 35 U.S.C. 154(b) by 162 days.

(21) Appl. No.: 18/740,978

(22) Filed: Jun. 12, 2024

(65) Prior Publication Data

US 2024/0324916 A1 Oct. 3, 2024

Related U.S. Application Data

(62) Division of application No. 18/197,275, filed on May 15, 2023, now Pat. No. 12,042,282.

(Continued)

(51) Int. Cl.

*A61B 5/1455* (2006.01)
*A61B 5/00* (2006.01)

(52) U.S. Cl.

CPC ........ *A61B 5/14552* (2013.01); *A61B 5/6815* (2013.01); *A61B 5/746* (2013.01); *A61B 2560/0456* (2013.01)

(58) Field of Classification Search

CPC .............. A61B 5/1455; A61B 5/14551; A61B 5/14552; A61B 5/6815; A61B 5/746; A61B 2560/0456

See application file for complete search history.

(56) References Cited

U.S. PATENT DOCUMENTS 1,497,905 A 6/1924 Hathaway
1,625,114 A 4/1927 Coryell (Continued)

FOREIGN PATENT DOCUMENTS

CN 101080192 A 11/2007
CN 107405085 A 11/2017

(Continued)

OTHER PUBLICATIONS

First Office Action and Search Report for Chinese Application No. 202080053888.9 mailed May 22, 2025, with English translation, 28 total pages.

(Continued)

*Primary Examiner* — Eric F Winakur
(74) *Attorney, Agent, or Firm* — COOLEY LLP

(57) ABSTRACT

An apparatus for monitoring an oxygen saturation level of a wearer includes a first body portion, a second body portion, and a connection member. The first body portion contains a processor, a memory operably coupled to the processor, at least one light-emitting diode, and at least one optical sensor configured to detect, during operation, a reflected portion of light emitted from the at least one light-emitting diode. The second body portion includes a grommet, and the connection member is mechanically coupled to each of the first body portion and the second body portion. The memory stores instructions to cause the processor to cause light to be emitted from the at least one light-emitting diode when the apparatus is positioned on an ear of a wearer and during operation of the apparatus, and to calculate a blood oxygen saturation level of the wearer based on the reflected portion of light.

20 Claims, 94 Drawing Sheets

Related U.S. Application Data

(60) Provisional application No. 63/342,100, filed on May 14, 2022.

(56) References Cited

U.S. PATENT DOCUMENTS 2,438,841 A 3/1948 Joseph et al.
3,043,354 A 7/1962 Fitzgerald
3,145,872 A 8/1964 Thomas et al.
D209,789 S 1/1968 Huston
3,416,655 A 12/1968 Jerome et al.
D234,968 S 4/1975 Ervin
3,876,130 A 4/1975 Haase
4,101,023 A 7/1978 Schuander
D257,930 S 1/1981 Conti
D260,134 S 8/1981 Bercu
D281,033 S 10/1985 Mohri
4,589,431 A 5/1986 Yuhara
D309,690 S 8/1990 Carlson
D333,560 S 3/1993 Miyashita et al.
D335,085 S 4/1993 Wacker
D337,177 S 7/1993 Tiramani et al.
D350,757 S 9/1994 Carpenter
5,638,838 A 6/1997 Lombardi
5,830,137 A 11/1998 Scharf
5,887,720 A 3/1999 Lin
D408,591 S 4/1999 Litton et al.
6,144,867 A 11/2000 Walker et al.
D439,376 S 3/2001 Lerolle
D459,299 S 6/2002 Hughes et al.
D460,218 S 7/2002 Thorpe
6,497,495 B1 12/2002 Janz
6,580,800 B1 6/2003 Yamasaki et al.
6,654,622 B1 11/2003 Eberhard et al.
D483,014 S 12/2003 Hsiao
D485,390 S 1/2004 Stancik et al.
6,677,078 B2 1/2004 Reise et al.
D504,672 S 5/2005 Hirano
D507,078 S 7/2005 Greenfield
D512,982 S 12/2005 Rodarte
D515,069 S 2/2006 Naito
D516,025 S 2/2006 Quinn
7,010,137 B1 3/2006 Leedom et al.
D518,477 S 4/2006 Chen
D551,216 S 9/2007 Wei
D552,087 S 10/2007 Wei
D553,077 S 10/2007 Kim et al.
D586,935 S 2/2009 Lassen
7,557,533 B2 7/2009 Yang
D598,375 S 8/2009 Nomi
D606,971 S 12/2009 Christopher et al.
7,738,935 B1 6/2010 Turcott
7,746,028 B1 6/2010 Yang et al.
D621,389 S 8/2010 Nagayama et al.
D626,289 S 10/2010 Lee
D633,899 S 3/2011 Zheng et al.
D635,961 S 4/2011 Gidden et al.
7,983,437 B2 7/2011 Wong et al.
D648,470 S 11/2011 Rains
D651,208 S 12/2011 Pacyga et al.
D652,817 S 1/2012 Lee et al.
D670,396 S 11/2012 Doogan
D671,096 S 11/2012 Song et al.
8,345,912 B2 1/2013 Akihiko et al.
8,430,817 B1 4/2013 Al-Ali et al.
D683,331 S 5/2013 Nylen
D698,026 S 1/2014 Kuwata et al.
D699,226 S 2/2014 Yoon
8,655,005 B2 2/2014 Birger et al.
D708,377 S 7/2014 Osiecki et al.
8,891,800 B1 11/2014 Shaffer
8,983,108 B2 3/2015 Ho
D727,301 S 4/2015 Smith et al.
D740,223 S 10/2015 Yoneta
D740,786 S 10/2015 Huang et al.
D744,698 S 12/2015 Kalyanpur et al.
D751,053 S 3/2016 Shin et al.
D756,971 S 5/2016 Park et al.
D758,901 S 6/2016 Benoit et al.
D771,599 S 11/2016 Kim
D783,422 S 4/2017 Kashimoto
D786,221 S 5/2017 Stoch
D801,312 S 10/2017 Birger
D809,664 S 2/2018 Ma et al.
D814,457 S 4/2018 Willis
D821,392 S 6/2018 Kwon et al.
D822,007 S 7/2018 Willis et al.
D826,748 S 8/2018 Kim et al.
D835,286 S 12/2018 Sebban
D846,264 S 4/2019 Wu
D851,035 S 6/2019 Hong
D851,913 S 6/2019 Yu
D853,350 S 7/2019 Linden et al.
D853,358 S 7/2019 Damboulev et al.
D853,992 S 7/2019 Kuh et al.
D853,993 S 7/2019 Kuh et al.
D855,808 S 8/2019 Smith et al.
D863,261 S 10/2019 Zhu
D865,663 S 11/2019 Yao
D871,069 S 12/2019 Carlson
D873,217 S 1/2020 Zhang
D880,458 S 4/2020 Minarsch et al.
D881,810 S 4/2020 Zhang
D886,083 S 6/2020 Cho et al.
D886,455 S 6/2020 Williamson et al.
D888,664 S 6/2020 Ma
D890,136 S 7/2020 Cohen et al.
D891,774 S 8/2020 Yu
D892,770 S 8/2020 Gao
D894,123 S 8/2020 Xiong
D902,856 S 11/2020 Klein et al.
D913,223 S 3/2021 Li
D916,291 S 4/2021 Fernando
10,987,067 B2 4/2021 Fernando
D920,236 S 5/2021 Xie
D937,774 S 12/2021 Fernando
D942,948 S 2/2022 Song
D962,900 S 9/2022 Fernando
12,042,282 B2 7/2024 Fernando et al.
12,402,844 B2 9/2025 Fernando
12,502,145 B2 12/2025 Fernando et al.
2006/0173406 A1 8/2006 Hayes et al.
2006/0258412 A1 11/2006 Liu
2007/0106126 A1 5/2007 Mannheimer et al.
2009/0227852 A1 9/2009 Glaser
2009/0275813 A1 11/2009 Davis
2009/0292166 A1 11/2009 Ito et al.
2010/0308999 A1 12/2010 Chornenky
2011/0034783 A1 2/2011 Lisogurski et al.
2012/0253159 A1 10/2012 Medina et al.
2013/0311104 A1 11/2013 Inoue
2014/0107493 A1 4/2014 Yuen et al.
2014/0243617 A1 8/2014 LeBoeuf et al.
2015/0305674 A1 10/2015 McPherson et al.
2016/0081562 A1 3/2016 Lachhman
2017/0094394 A1 3/2017 McPeak et al.
2018/0014113 A1 1/2018 Boesen
2018/0042496 A1 2/2018 Lachhman et al.
2018/0049654 A1 2/2018 Melker et al.
2018/0235692 A1 8/2018 Efimov et al.
2019/0045291 A1* 2/2019 Kofman .............. A61B 5/0075
2019/0059752 A1 2/2019 Botsva et al.
2019/0082974 A1 3/2019 LeBoeuf et al.
2019/0090812 A1* 3/2019 Martin .................. A61B 5/746
2019/0117159 A1 4/2019 Peeters et al.
2019/0212198 A1 7/2019 Marsh
2019/0313983 A1 10/2019 Horiguchi et al.
2020/0110569 A1 4/2020 Deng
2020/0162807 A1 5/2020 Lim
2020/0196042 A1 6/2020 Cai
2020/0216228 A1 7/2020 Wang et al.
2020/0304899 A1 9/2020 Cramer et al.
2020/0321791 A1 10/2020 Rugolo et al.
2020/0330012 A1 10/2020 Lamego et al.
2020/0390402 A1 12/2020 Fernando

(56) References Cited

U.S. PATENT DOCUMENTS

| | | | | |
|---|---|---|---|---|
| 2021/0100507 | A1 | 4/2021 | Kimmig et al. | |
| 2021/0204887 | A1 | 7/2021 | Fernando | |
| 2021/0235178 | A1 | 7/2021 | Cai | |
| 2021/0275111 | A1 | 9/2021 | Fernando | |
| 2021/0377646 | A1 | 12/2021 | Luo | |
| 2021/0377672 | A1 | 12/2021 | Grinnip, III et al. | |
| 2022/0376530 | A1* | 11/2022 | Bluhme | H02J 7/731 |
| 2023/0363670 | A1 | 11/2023 | Fernando et al. | |
| 2025/0345008 | A1 | 11/2025 | Fernando | |

FOREIGN PATENT DOCUMENTS

| | | | |
|---|---|---|---|
| CN | 109074715 | A | 12/2018 |
| CN | 208799232 | U | 4/2019 |
| EA | 001936 | B1 | 10/2001 |
| EM | 0079552240001 | | 5/2020 |
| EM | 0083245520001 | | 12/2020 |
| EM | 0086695270001 | | 9/2021 |
| EP | 2094152 | B1 | 4/2016 |
| GB | 2546775 | A | 8/2017 |
| GB | 90082652500001 | | 11/2020 |
| IN | 3294250010001 | | 5/2020 |
| JP | S61279224 | A | 12/1986 |
| JP | 2003220052 | A | 8/2003 |
| JP | 2012200267 | A | 10/2012 |
| JP | 2014008310 | A | 1/2014 |
| JP | 2016514992 | A | 5/2016 |
| JP | 2018508325 | A | 3/2018 |
| JP | 2018509201 | A | 4/2018 |
| JP | 2019037547 | A | 3/2019 |
| JP | D1692300 | | 7/2021 |
| JP | D1696301 | | 9/2021 |
| RU | 2107280 | C1 | 3/1998 |
| RU | 2001134563 | A | 3/2004 |
| RU | 2008121176 | A | 12/2009 |
| RU | 151514 | U1 | 4/2015 |
| RU | 166763 | U1 | 12/2016 |
| WO | WO-9715229 | A1 | 5/1997 |
| WO | WO-9822804 | A1 | 5/1998 |
| WO | WO-2006064399 | A2 | 6/2006 |
| WO | WO-2014007210 | A1 | 1/2014 |
| WO | WO-2014096353 | A1 | 6/2014 |
| WO | WO-2016120870 | A1 | 8/2016 |
| WO | WO-2016130545 | A1 | 8/2016 |
| WO | WO-2016193049 | A1 | 12/2016 |
| WO | WO-2017119638 | A1 | 7/2017 |
| WO | WO-2017120208 | A1 | 7/2017 |
| WO | WO-2019039223 | A1 | 2/2019 |
| WO | WO-2020257291 | A1 | 12/2020 |
| WO | WO-2023225479 | A2 | 11/2023 |
| WO | WO-2024181889 | A1 | 9/2024 |

OTHER PUBLICATIONS

Notice of Acceptance for New Zealand Application No. 784042, by Oxiwear, Inc., mailed Jun. 24, 2025, 2 pages.

Notice of Allowance for U.S. Appl. No. 17/209,667 mailed Apr. 28, 2025, 5 pages.

Notice of Allowance for U.S. Appl. No. 17/209,872 mailed Aug. 19, 2025, 5 pages.

Office Action for Canadian Application No. 3143201 mailed Aug. 28, 2025, 5 pages.

Office Action for Japanese Application No. 2021-571384, by Oxiwear, Inc., mailed Jun. 24, 2025, 6 pages, with English Translation.

Office Action for Korean Application No. 10-2022-7001060 mailed Jul. 9, 2025, with English Translation, 33 pages.

Office Action for Mexican Application No. MX/a/2021/015218, by Oxiwear, Inc., mailed May 23, 2025, 16 pages with English Translation.

Office Action for New Zealand Application No. 784042 mailed May 16, 2025, 3 pages.

AU Application No. 2025201555, Office Action mailed Dec. 3, 2025, Applicant OxiWear, Inc.; 4 pages.

AU Application No. 2025202686, Examination report No. 1 mailed Dec. 18, 2025; Applicant OxiWear, Inc.; 4 pages.

BR Application No. 112021024790.4, Office Action and Search Report mailed Oct. 14, 2025, Applicant OxiWear Inc.; with English translation, 5 pages.

EP Application No. 23808491.7, Extended European Search Report mailed Nov. 12, 2025; Applicant OxiWear, Inc.; 14 pages.

IL Application No. 288809, Office Action mailed Jan. 1, 2026; Applicant Oxiwear Inc., 5 total pages.

JP Application No. 2021571384, Decision to Grant mailed Dec. 1, 2025; Applicant OxiWear, Inc.; with English Translation; 5 pages.

MX Application No. MX/a/2021/015218, Notice of Allowance mailed Nov. 14, 2025; Applicant Oxiwear, Inc; English Machine Translation; 6 pages.

U.S. Appl. No. 17/209,872, Notice of Allowance mailed Nov. 10, 2025; Inventor Fernando, Shavini.; 4 pages.

U.S. Appl. No. 19/410,816, filed Dec. 5, 2025; Inventor Fernando, Shavini Evendri et al.

Final Office Action for U.S. Appl. No. 17/209,872 mailed Apr. 2, 2025, 19 pages.

Office Action for Australian Application No. 2020296003 mailed Jan. 30, 2025, 4 pages.

Office Action for Australian Application No. 2020296003 mailed Mar. 14, 2025, 4 pages.

Office Action for European Application No. 20827530.5 mailed Mar. 21, 2025, 7 pages.

Office Action for Indian Application No. 202117060391 mailed Jan. 31, 2025, 6 pages.

Office Action for Israel Application No. 288809 mailed Feb. 23, 2025, 6 pages.

Office Action for New Zealand Application No. 784042 mailed Jan. 14, 2025, 6 pages.

Extended European Search Report for European Application No. EP20200827530 dated May 25, 2023, 7 pages.

Final Office Action for U.S. Appl. No. 17/209,667 dated Sep. 28, 2023, 10 pages.

Final Office Action for U.S. Appl. No. 17/209,872 dated Nov. 8, 2023, 12 pages.

International Preliminary Report on Patentability for International Application No. PCT/US2020/038146 dated Dec. 30, 2021, 8 pages.

International Search Report and Written Opinion for International Application No. PCT/US2020/038146, mailed Sep. 28, 2020, 9 pages.

International Search Report and Written Opinion for PCT Application No. PCT/US2023/067008 dated Jan. 22, 2024, 18 pages.

Invitation to pay additional fees for International Application No. PCT/US2023/067008, dated Oct. 2, 2023, 2 pages.

Nikandrov, P. A., "Approbation of experimental apparatus for visualization of blood vessels", Engineering Bulletin of the Don (2018); 1(48); p. 25; 14 pages with English Abstract.

Non-Final Office Action for U.S. Appl. No. 18/197,275 dated Nov. 6, 2023, 7 pages.

Notice of Allowance for U.S. Appl. No. 18/197,275 dated Mar. 13, 2024, 7 pages.

Office Action and Search report for Russian Application No. RU2022100627 dated Oct. 2, 2023, 32 pages.

Office Action for Canadian Application No. CA3143201 dated Dec. 7, 2023, 5 pages.

Office Action for Japanese Patent Application No. JP20210571384 dated Mar. 29, 2024, 41 pages.

Office Action for New Zealand Application No. NZ784042 mailed Jun. 25, 2024, 5 pages.

Office Action for Russian Patent Application No. RU2022100627 dated Feb. 27, 2024, 40 pages.

Pokrovsky, V. I., "Encyclopedic Dictionary of Medical Terms", "Meditsina" Publishing House, Moscow (2001); p. 102; 3 pages with English translation.

Search Report for Japanese Application No. JP2021571384 dated Feb. 21, 2024, 105 pages with English Translation.

(56) References Cited

OTHER PUBLICATIONS

Sesin, E. M., et al., "Personal identification systems based on the integration of several biometric characteristics of a person", TUSUR Reports (Jun. 2012); No. 1 (25), part 2; pp. 175-179; 10 pages with English Machine Translation.
Singapore Application No. 11202112831U: Written Opinion, dated Aug. 9, 2023, 9 pages.
U.S. Appl. No. 16/903,732: Notice of Allowance, mailed Feb. 22, 2021, 12 pages.
U.S. Appl. No. 16/903,732: Office Action, mailed Oct. 2, 2020, 10 pages.
U.S. Appl. No. 17/209,667: Non-Final Office Action, dated Mar. 30, 2023, 9 pages.
U.S. Appl. No. 17/209,872: Non-Final Office Action, mailed Apr. 12, 2023, 18 pages.
U.S. Appl. No. 18/197,275: Restriction Requirement, mailed Aug. 3, 2023, 6 pages.
Decision to Grant for Russian Application No. 2022100627, by Oxiwear, Inc., mailed Jul. 22, 2024, 36 pages with English Translation.
International Preliminary Report on Patentability for International Application No. PCT/US2023/067008, by Oxiwear, Inc., mailed Nov. 28, 2024, 14 pages.
Non-Final Office Action for U.S. Appl. No. 17/209,667 mailed Sep. 10, 2024, 22 pages.
Non-Final Office Action for U.S. Appl. No. 17/209,872, Fernando, Shavini, mailed Sep. 10, 2024, 20 pages.
Office Action for Canadian Application No. 3,143,201, by Oxiwear, Inc., mailed Oct. 23, 2024, 5 pages.
Office Action for Israel Application No. 288809, by Oxiwear, Inc., mailed Aug. 8, 2024, 3 pages.
Office Action for Japanese Application No. 2021-571384, by Oxiwear, Inc., mailed Nov. 27, 2024, 27 pages with English Machine Translation.
Office Action for Mexican Application No. MX/a/2021/015218, by Oxiwear, Inc., mailed Oct. 8, 2024, 10 pages with English Translation.
CN Application No. 202080053888.9, Office Action and Search Report mailed Mar. 26, 2026; Applicant Oxiwear, Inc., with English Translation; 22 pages.
EP Application No. 20827530.5, Office Action mailed Feb. 6, 2026; Applicant OXIWEAR Inc., 10 total pages.
PCT Application No. PCT/IB2025/062515, International Search Report and Written Opinion mailed Mar. 12, 2026, Applicant Oxiwear, Inc.; 14 pages.
CA Application No. 3143201 Office Action mailed Jun. 30, 2026; Applicant Oxiwear, Inc., 6 total pages.
RU Application No. 2024137404, Office Action mailed Jun. 5, 2026; Applicant Oxiwear, Inc., with English Translation; 19 total pages.

* cited by examiner

150

100
150

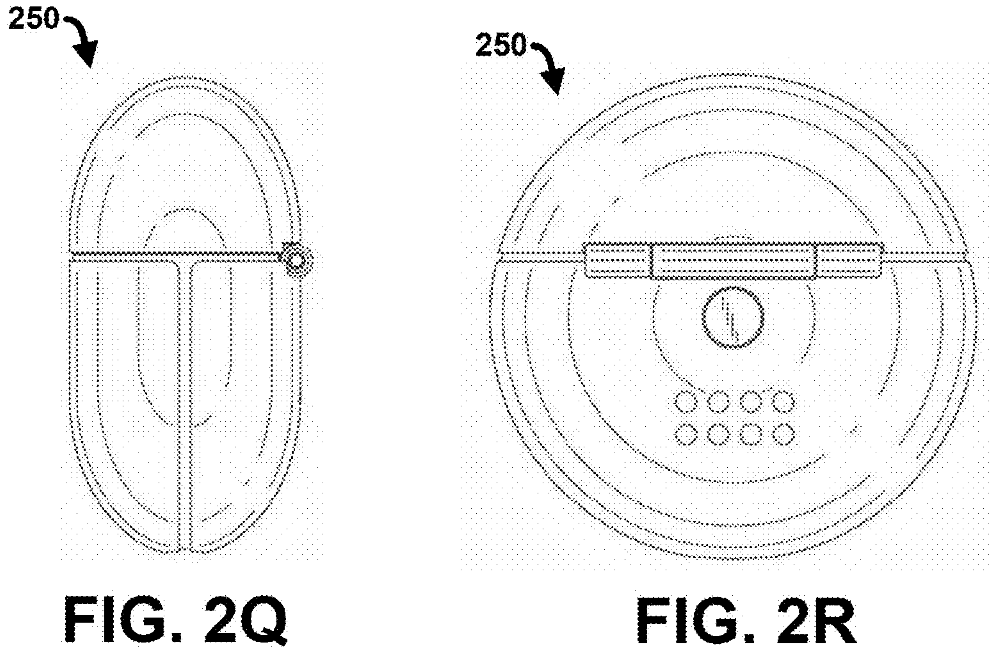
FIG. 2Q
FIG. 2R
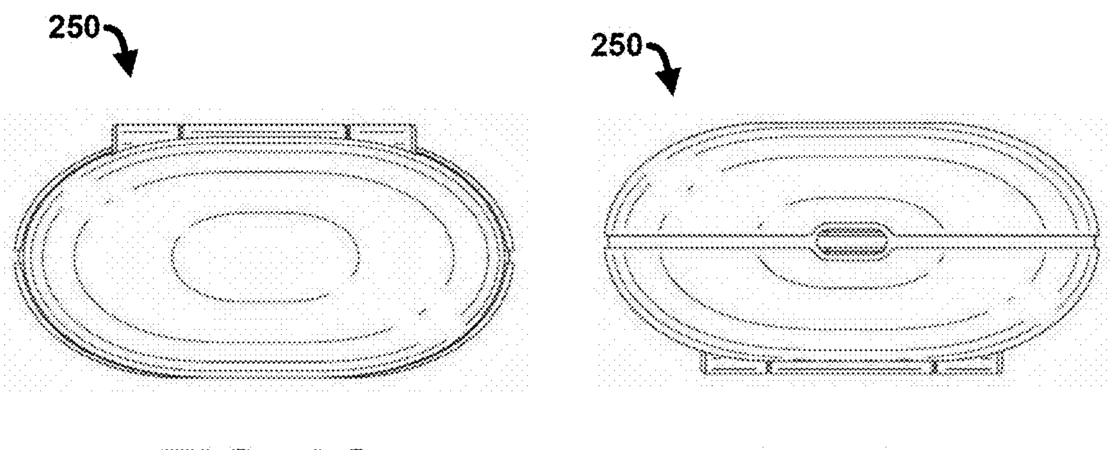
FIG. 2S
FIG. 2T

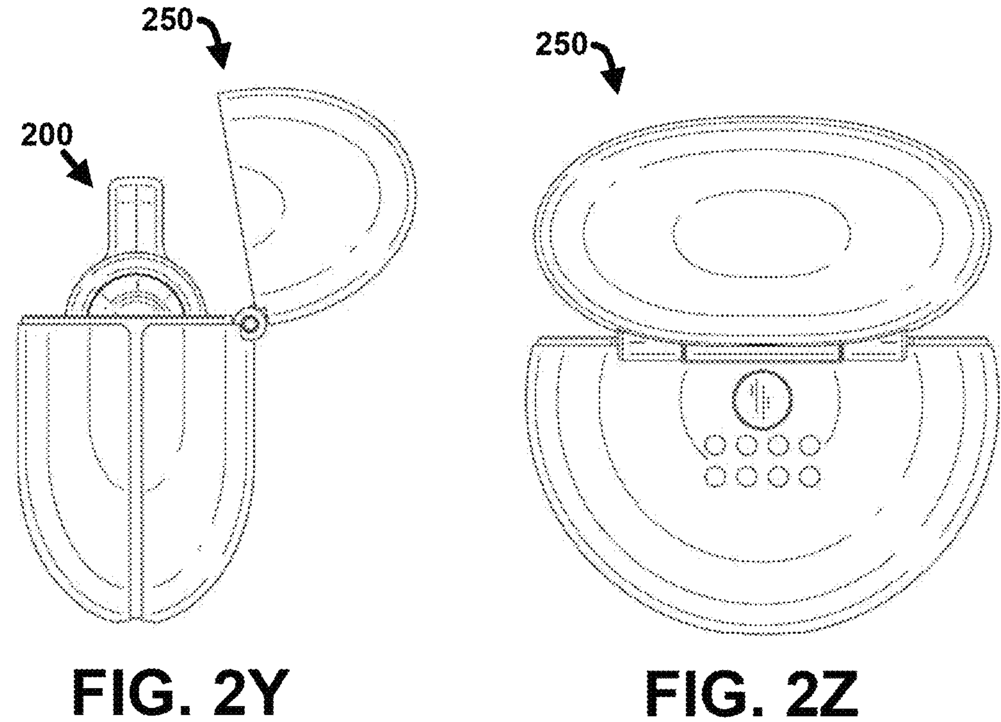
FIG. 2Y
FIG. 2Z
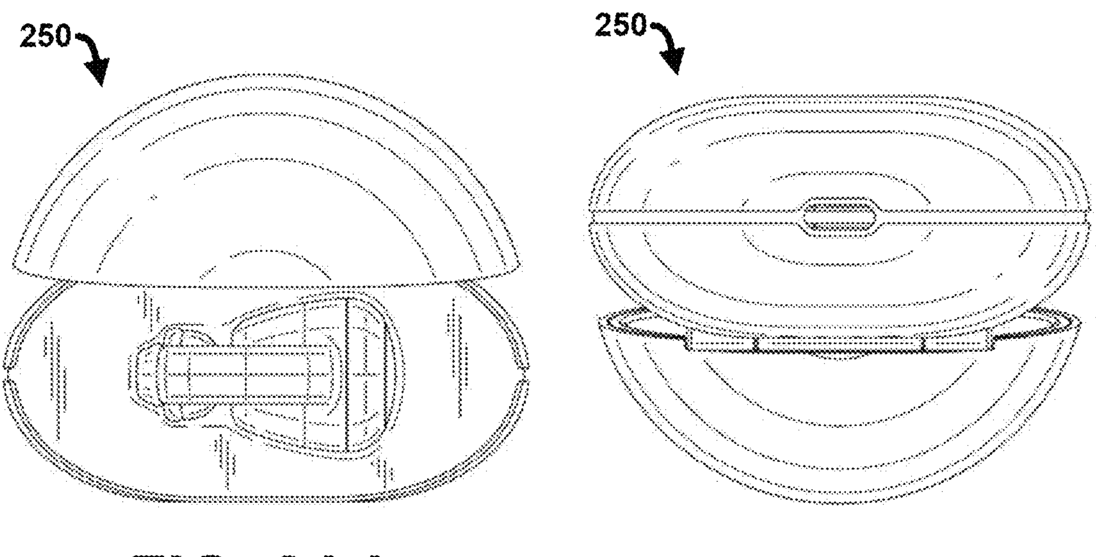
FIG. 2AA
FIG. 2AB

Welcome to Oxiwear

Personalize to your safe SPO2 threshold

Warning when SPO2 levels are low

Sign Up first name email password

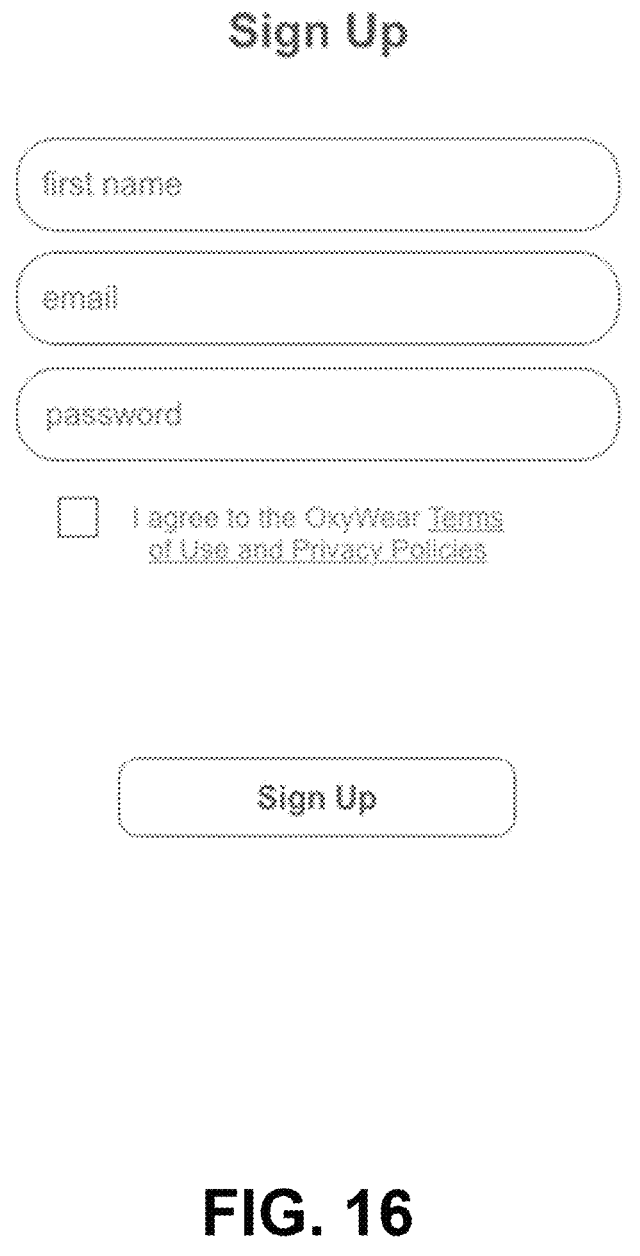

I agree to the OxyWear Terms of Use and Privacy Policies

Sign Up

FIG. 16

Welcome to Oxiwear

Dial 911 with the press of a button

Speak with 911 through your device

Welcome to Oxiwear

Enter emergency contacts
to enable text alerts

Make sure your bluetooth is on and
your OxiWear device is close by

Press "Start" to set up your device!

START

Welcome to Oxiwear

Continuous SPO2 Monitoring
SPO2 - amount of oxygen in the blood

Connected

The following questions will help us customize your OxiWear experience

Get Started

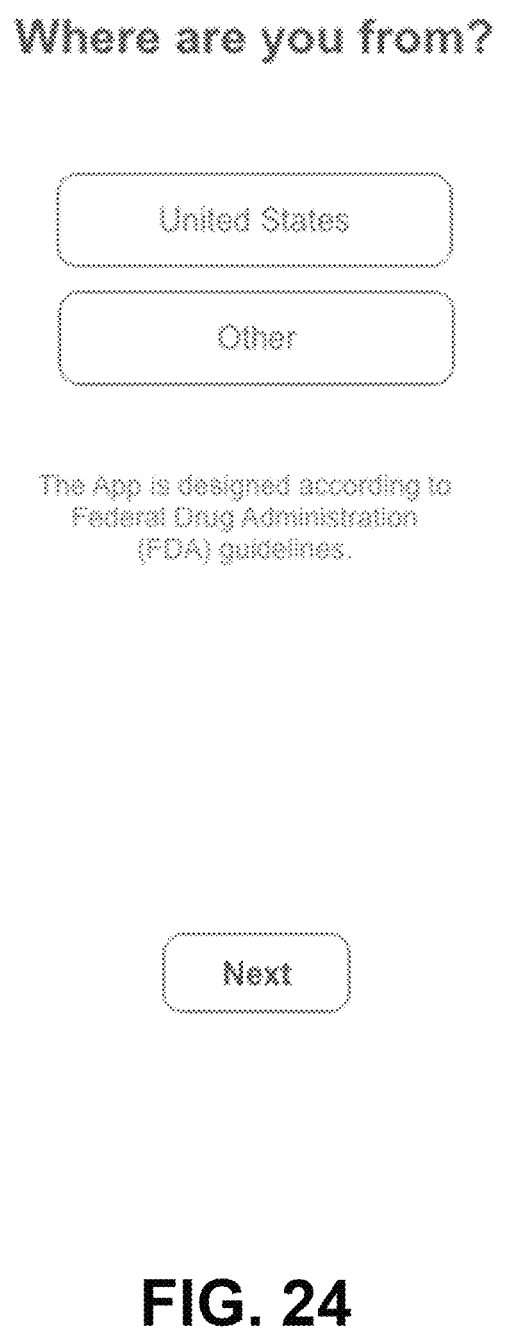

Where are you from?

United States

Other

The App is designed according to
Federal Drug Administration
(FDA) guidelines.

Next

FIG. 24

Settings

Alerts and Notifications

Location Services

Unit Preferences

Language Preference

App Sync

Personalization

Journal

Date
Time

SPO2: AQI:
HR: Altitude:

Medication (add icon)

add medication

Symptoms (add icon)

add symptom

Notes (add icon)
click to add notes

Emergency Info

Emergency Contacts

Doctor's Notes click to add notes

Notes for EMS click to add notes

Select your Gender

Male

Female

*blurb about why this information is important

Next

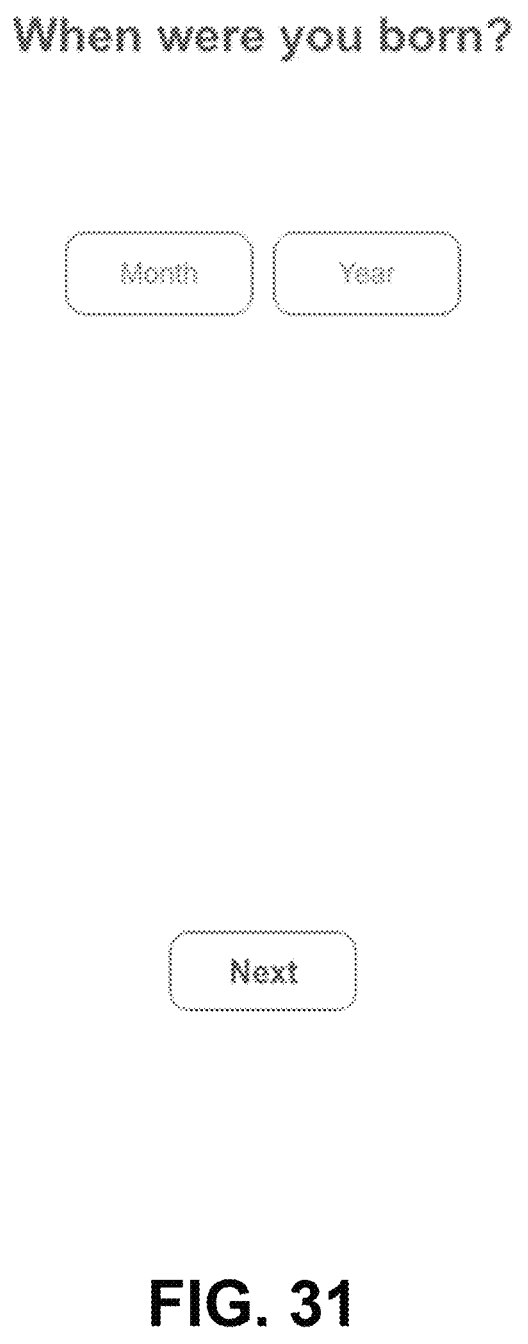

When were you born?

Month Year

Next

FIG. 31

What is your weight?

Sync with Apple Health

Next

FIG. 33

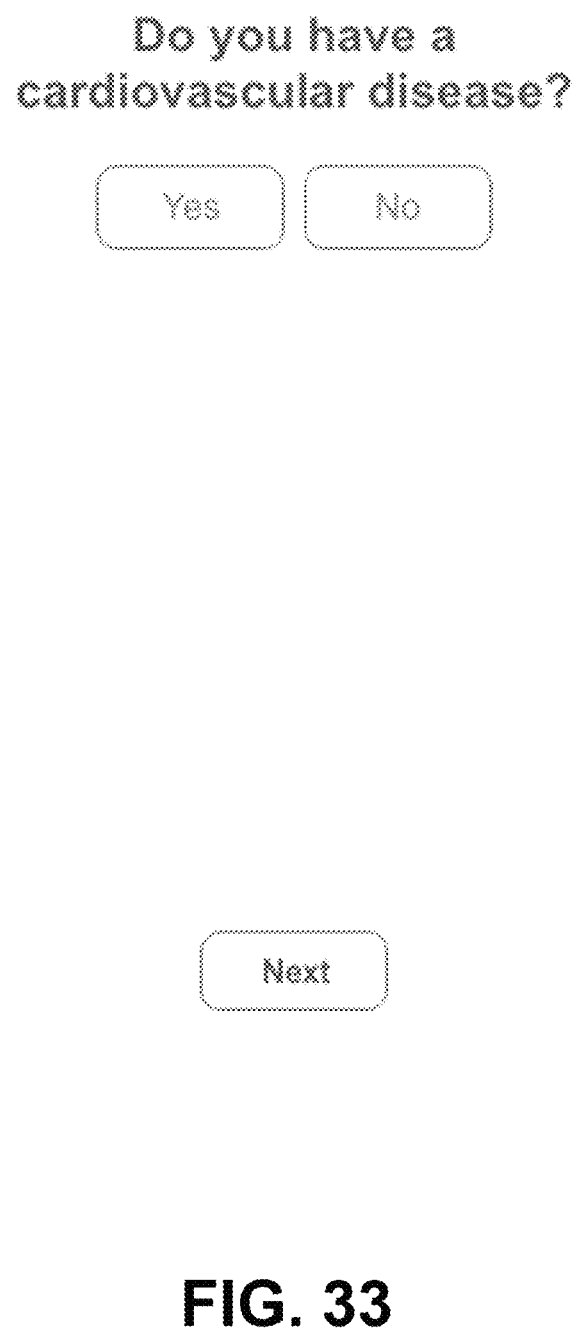

Sign In email password

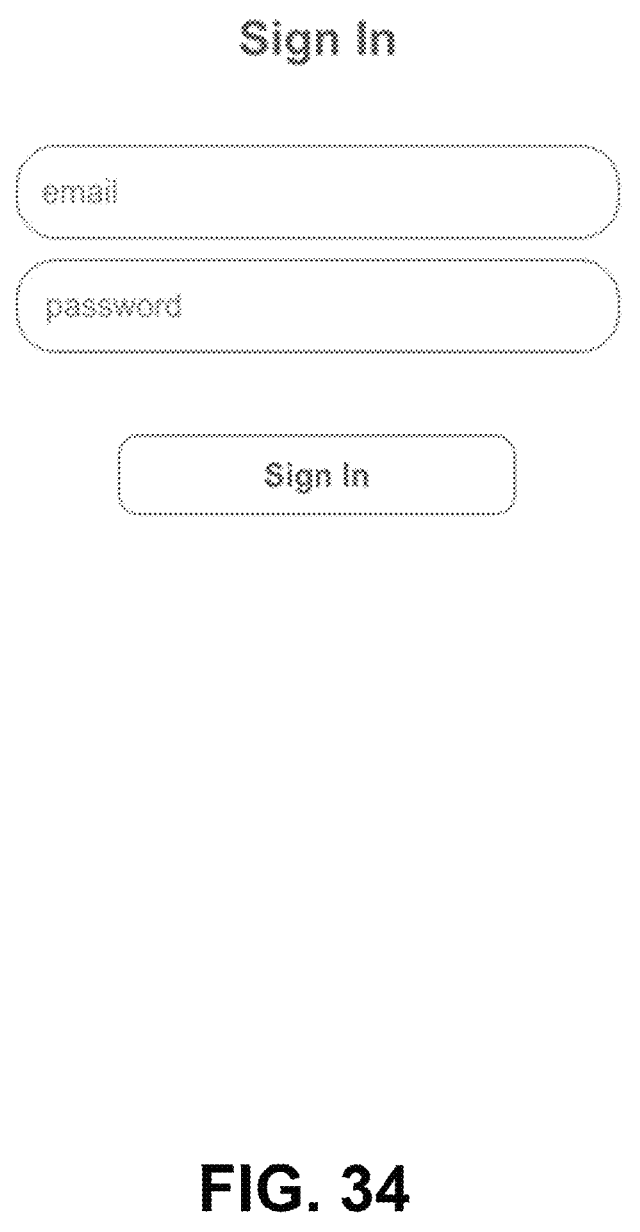

Sign In

FIG. 34

Do you have pulmonary hypertension (PH)?

Yes No

Next

Figure 36:
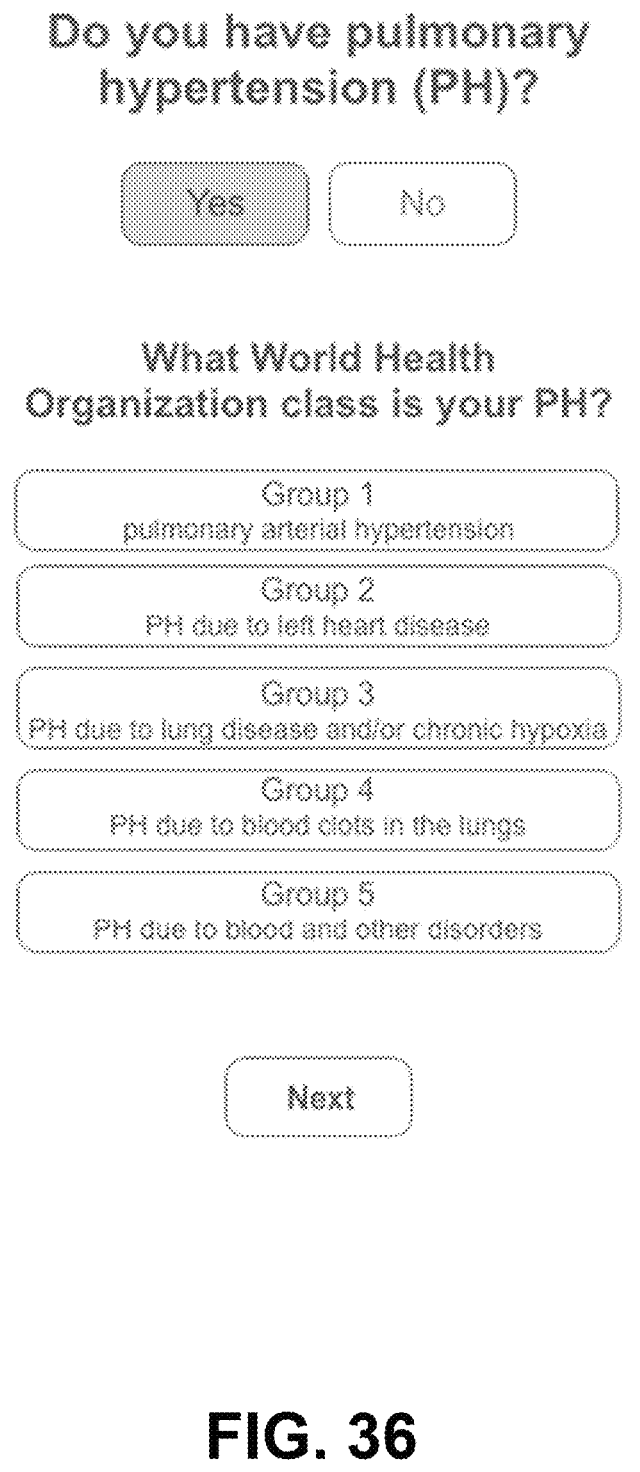

FIG. 42
9:41
Emergency
Premium Account
Predictive analysis and
Save or share detailed reports
View weekly and monthly SPO2 and HR data on your dashboard
START
Dashboard
Reports
Medical ID
Progress
Journal

« December 2021 »

| S | M | T | W | T | F | S |
|---|---|---|---|---|---|---|
| 29 | 30 | 1 | 2 | 3 | 4 | 5 |
| 6 | 7 | 8 | 9 | 10 | 11 | 12 |
| 13 | 14 | 15 | 16 | 17 | 18 | 19 |
| 20 | 21 | 22 | 23 | 24 | 25 | 26 |
| 27 | 28 | 29 | 30 | 31 | | |

Endurance traning
Completed 2 hours of Endurance training to... 10:28:03 pm

Finished 2 Miles Cycling
Today I finished 2 miles cycling and feels go... 11:28:03 pm

EAR-WEARABLE OXYGEN MONITORING SYSTEM

CROSS-REFERENCE TO RELATED APPLICATIONS

The application is a divisional of U.S. patent application Ser. No. 18/197,275, filed May 15, 2023 and titled "Ear-Wearable Oxygen Monitoring System," which claims priority to and the benefit of U.S. Provisional Patent Application No. 63/342,100, filed May 14, 2022 and titled "Ear-Wearable Oxygen Monitoring System," the disclosures of each of which are hereby incorporated by reference in their entireties.

FIELD

The present disclosure relates to physiological monitoring technology, and more specifically, to the monitoring of an oxygen level of a wearer of a device.

BACKGROUND

Conditions such as pulmonary hypertension can be treated by providing the patient with supplemental oxygen therapy. The supplemental oxygen therapy can include delivering oxygen to the patient continuously, or during specific events such as exercise or sleep.

SUMMARY

In some embodiments, an apparatus for monitoring an oxygen saturation level of a wearer of the apparatus includes a first body portion, a second body portion, and a connection member. The first body portion includes a processor, a memory operably coupled to the processor, at least one light-emitting diode operably coupled to the processor, and at least one optical sensor configured to detect, during operation, a reflected portion of light emitted from the at least one light-emitting diode. The second body portion includes a grommet, and the connection member is mechanically coupled to each of the first body portion and the second body portion. The memory stores instructions to cause the processor to cause light to be emitted from the at least one light-emitting diode when the apparatus is positioned on an ear of a wearer and during operation of the apparatus, and to calculate a blood oxygen saturation level of the wearer based on the reflected portion of light.

In some embodiments, a kit includes an apparatus for monitoring an oxygen saturation level of a wearer of the apparatus, a charger case, and a plurality of flexible earpads. The apparatus is configured to be positioned on an ear of the wearer, and includes a first body portion, a second body portion, and a connection member mechanically coupled to each of the first body portion and the second body portion. The first body portion has a processor, a memory operably coupled to the processor, at least one light-emitting diode (LED), and at least one optical sensor. The at least one optical sensor is configured to detect, during operation, a reflected portion of light emitted from the at least one light-emitting diode, and the reflected portion of light can include light that is reflected from a surface of the ear of the wearer. The memory stores instructions to cause the processor to calculate a blood oxygen saturation level of the wearer based on the reflected portion of light. The charger case is configured to contain the apparatus and to supply power to the apparatus. Each flexible earpad from the plurality of flexible earpads is configured to be mechanically coupled to the second body portion, for example via a grommet/annular region of the second body portion.

In some embodiments, a method of manufacturing an oxygen saturation level monitoring apparatus includes bonding an electronics board to an earpad using at least one of silicone or epoxy such that the electronics board is affixed to the earpad within a cavity defined in a surface of the earpad, and attaching the earpad to a chassis. The chassis can include a first body portion, a second body portion, and a connection member, as described herein.

BRIEF DESCRIPTION OF THE DRAWINGS

FIGS. 2A-2N are drawings of a wearable oxygen monitor, configured to be worn about a portion of an ear of a user, according to some embodiments.

FIGS. 2O-2V are drawings of a charger case in a closed configuration, the charger case configured to contain, and to supply power to, the wearable oxygen monitor of FIGS. 2A-2N, according to some embodiments.

FIGS. 2W-2AD are drawings of the charger case of FIGS. 2O-2V in an open configuration, the charger case containing the wearable oxygen monitor of FIGS. 2A-2N.

FIGS. 2AE-2AF are drawings of the charger case of FIGS. 2O-2V in an open configuration and not containing a wearable oxygen monitor.

FIG. 2AG is a rendering of a charger case with a panel removed to show an underlying shape of a recess/pocket configured to receive a wearable oxygen monitor, according to some embodiments.

FIGS. 12-60 are wireframes of user interface screens of a mobile app that interacts with a wearable oxygen monitor, according to some embodiments.

DETAILED DESCRIPTION

Figures 1A, 1B:
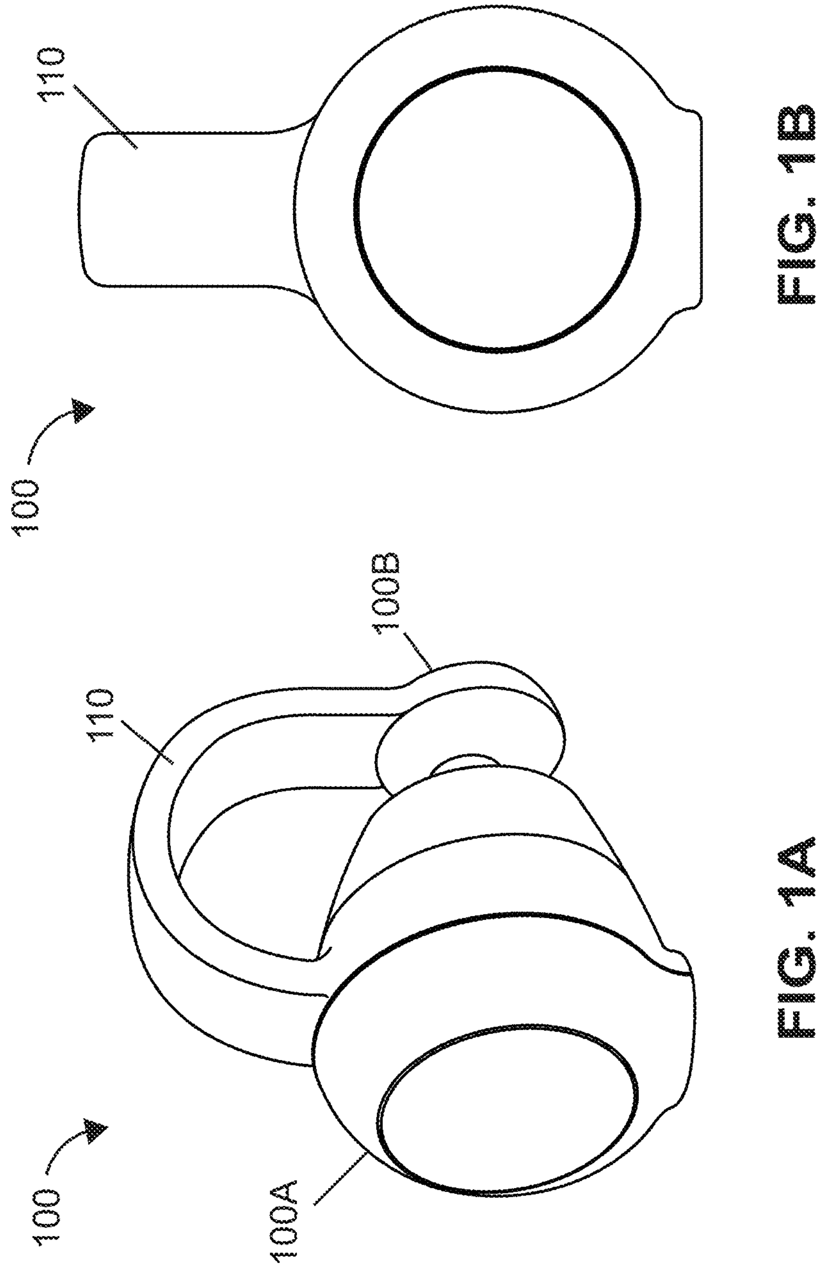
FIGS. 1A-1C are renderings of a wearable oxygen monitor, configured to be worn about a portion of an ear of a user, according to some embodiments.

Some health conditions, such as pulmonary hypertension (PH), pulmonary arterial hypertension (PAH) and idiopathic PAH (IPAH) are managed through the administration of oxygen and, relatedly, the monitoring of oxygen levels. Known devices for monitoring oxygen levels (such as pulse oximeters), however, are typically worn on the finger of a patient for discrete periods of time for measurement, and then taken off, for example because they are not designed or comfortable for continuous wear. Moreover, when a patient sleeps, he or she is not typically wearing a pulse oximeter, and is unable to view a digital readout of the pulse oximeter. As such, known pulse oximeters may not be effective for a notifying the patient of a critical drop in his or her oxygen level, for example while he/she sleeps, potentially leading to an exacerbation of the condition or even death. Moreover, known pulse oximeters do not include automated emergency detection and response capabilities. In other words, a user make take a voluntary action to measure his/her oxygen level, and upon determining that the level is too low, take another voluntary action to address it (e.g., call a doctor or emergency services using another device such as a telephone), if he/she is capable of doing so, potentially wasting valuable time.

Embodiments of the present disclosure include a wearable oxygen monitor that can be continuously worn and perform continuous oxygen monitoring and to alert a wearer/user when a detected oxygen level, detected during the oxygen monitoring, is lower than a predetermined or predefined threshold value. In some embodiments, the wearable oxygen monitor includes a first body portion, a second body portion, and a connection member or a connection portion that is disposed or positioned between the first body portion and the second body portion. The first body portion includes a processor, a memory operably coupled to the processor, at least one light-emitting diode (LED), and at least one optical sensor configured to detect, during operation, a reflected portion of light emitted from the at least one light-emitting diode. The second body portion includes a grommet, and the connection member is mechanically coupled to each of the first body portion and the second body portion. The memory stores instructions to cause the processor to cause light to be emitted from the at least one light-emitting diode when the apparatus is positioned on an ear of a wearer and during operation of the apparatus, and to calculate a blood oxygen saturation level of the wearer based on the reflected portion of light. Additional details about certain aspects of the wearable oxygen monitors described herein can be found, by way of example, in U.S. Pat. No. 10,987,067, titled "Wearable Earpiece Oxygen Monitor," issued Apr. 27, 2021, the entire contents of which are incorporated herein by reference for all purposes.

In some implementations, the connection member includes or is made of nylon, and thus is only slightly compliant (but primarily rigid), and an adjustability of the wearable oxygen monitor and/or a conformity of the wearable oxygen monitor to an ear shape of the wearer/user are accomplished via a pair of earpads, one or both of which may be flexible (e.g., silicone pads), and at least one of which is interchangeable with different sizes. In other words, at least one of the flexible earpads from the pair of flexible earpads can be removed from the wearable oxygen monitor and replaced with an earpad having different dimensions. In some such implementations, only one of the flexible earpads from the pair of flexible earpads is configured to be readily removable and replaced by the user. The removable earpad can be coupled, for example, to the second body portion via a ring-shaped structure thereof (also referred to herein as a "grommet" or "annular opening"), as discussed further below.

In some implementations, the at least one optical sensor is positioned within, and secured to, a cavity defined within a surface of one of the earpads (e.g., a flexible earpad that is coupled to the first body portion, and optionally not configured to be readily removed/replaced by the user, or a non-flexible earpad that is optionally not configured to be readily removed/replaced by the user). The at least one optical sensor can be "potted" in a substance such as an epoxy (e.g., an optically transparent epoxy, such that optical signals are not interfered with/altered, or are minimally interfered with/altered).

In some implementations, wearable oxygen monitors of the present disclosure include a flexible conductor (e.g., having a substantially S-shaped or curved/serpentine "ribbon" shape) such that at least a sub-assembly of the wearable oxygen monitor can "flex" to accommodate the process of positioning the wearable oxygen monitor on the ear of the user/wearer. Alternatively or in addition, wearable oxygen monitors of the present disclosure can include a DC power line communication transceiver chipset (e.g., Maxim MAX20340).

In some embodiments, a wearable oxygen monitoring kit includes an ear-wearable device ("wearable oxygen monitor"), a charger case, and optionally a set of flexible earpads configured to be interchangeably attached to the ear-wearable device via a grommet, as shown and described herein. Each flexible earpad from the set of flexible earpads can have a different set of associated dimensions, such that a "fit" of the ear-wearable device can be adjusted/customized for different user (ear) sizes/geometries. Improving the fit of the ear-wearable device relative to the user/wearer can result in improvements to optical signal quality during operation of the ear-wearable device, as well as improvements to user comfort and ergonomics. In some such implementations, the charger case and the ear-wearable device are configured to exchange data and power (e.g., simultaneously) via one or more (e.g., two) charging contacts. Although described above as being "flexible" for purposes of conforming to a user's ear, the earpads can alternatively be formed from inflexible or substantially inflexible materials, for example for applications calling for greater durability/ruggedization (e.g., for underwater use, military use, etc.).

In some embodiments, during manufacture/assembly of a wearable oxygen monitor, an optical board (i.e., a circuit board including at least one optical sensor and/or at least one optical detector) is bonded to an ear pad using silicone (e.g., optically-clear silicone) or another material such as epoxy, thereby producing at least a sub-assembly (i.e., the optical board and the earpad) that is waterproof and that provides optical transparency sufficient for acceptable performance of the at least one optical sensor and/or at least one optical detector.

In some embodiments, wearable oxygen monitors of the present disclosure can include an alert mechanism such as a button or touchscreen that, when interacted with by a user, initiates/activates one or more processes (e.g., stored in a memory of the wearable oxygen monitor and executable via a processor (e.g., a microprocessor) of the wearable oxygen monitor). The one or more processes can include an emergency plan. The emergency plan can include, but is not limited to, one or more of: contacting emergency services (e.g., initiating a telephone call to 911), sending a short message service (SMS) message (i.e., a text message) alert to a pre-programmed phone number (e.g., to a mobile device of the user or other designated person), emitting a sound from a sound emitter of the wearable oxygen monitor (e.g., an electronic beep sound effect emitted via a speaker), a vibration generated by a haptic feedback element of the wearable oxygen monitor (e.g., a piezoelectric transducer), transmitting (e.g., via a transceiver onboard the wearable oxygen monitor) a signal to a mobile device to cause an alert such as a sound effect and/or a vibration, etc.

In some embodiments, a wearable oxygen monitor is configured to dial 911 (or other emergency service) in response to button press (or other interaction with an alert mechanism) made by a wearer/user, for example as part of a defined emergency plan. The wearable oxygen monitor can also include a speaker and microphone such that the oxygen monitor functions as a headset. For example, the wearer/user can hear the voice of the emergency response dispatcher via the speaker of the wearable oxygen monitor, and the wearer/user can speak to the emergency response dispatcher via the microphone of the wearable oxygen monitor. In some implementations, in response to the button press and in addition to dialing 911, the wearable oxygen monitor can be configured to concurrently trigger the generation and sending (e.g., via a wireless communication channel) of an alert text message to one or more emergency contact numbers (e.g., three separate emergency contact numbers) stored in a memory of the wearable oxygen monitor and/or accessible by the wearable oxygen monitor via a mobile software application thereof. The alert text message(s) can include one or more of: an alert message, vital signs/biometrics of the wearer/user, and an indication that 911 has been called.

In some embodiments, a wearable oxygen monitor is in the form of a wearable, hardware-based earpiece that is sized and shaped to fit and be worn about a portion of a wearer's ear (e.g., a helix, scapha, pinna, or any other portion of the external ear). The earpiece can clip onto, mechanically attach to, or otherwise grip the portion of the ear. For example, the earpiece include a gap or recess, defined therein, that is sized and shaped to receive the portion of the ear. When the ear portion is inserted into or received by the gap or recess, the earpiece can be configured to exert a bias or spring force that provides a squeezing action about the ear portion, such that the earpiece is securely retained on the wearer's ear. The wearable oxygen monitor can include one or more of: one or more light-emitting diodes (LEDs), one or more photosensors/photodetectors, one or more lightweight, power-efficient, wireless sensors (e.g., temperature sensor(s), pressure sensor(s), accelerometer(s), GPS sensor(s), etc.), a speaker, a microphone, a processor and a memory operably coupled to the processor. The memory stores instructions executable by the processor during operation. During operation, the one or more LEDs (e.g., red and/or green LEDs) can emit light through the portion of the ear, and the light transmitted through the portion of the ear can be detected at the one or more photosensors/photodetectors. One or more biometrics or vital signs can then be calculated (e.g., blood oxygen level, blood oxygen saturation (SpO2), heart rate, body temperature, pulse rate, respiration rate, blood pressure, hydration, etc.) based on the amount of light that is detected at the one or more photosensors/photodetectors and/or based on an amount of light that is absorbed by the ear (and, thus, does not reach the one or more photosensors/photodetectors). For example, blood oxygen saturation (SpO2) can be calculated based on the amount of light that is absorbed by the ear and using Beer's law (also referred to as the Beer-Lambert law, which states that absorbance is proportional to the concentration of one or more attenuating species in a material sample). In some implementations, an accuracy of the determination of the blood oxygen saturation increases with the thickness of the portion of the ear on which the wearable oxygen monitor is positioned during operation.

In some embodiments, the one or more LEDs include two LEDs—a first LED being a red (650 nm) LED and a second LED being an infrared (950 nm) LED. During operation, when light from each of the two LEDs passes through an adjacent portion of the ear, light emitted from the first (red) LED is partially absorbed by deoxyhemoglobin of the portion of the ear, and light emitted from the second (infrared) LED is partially absorbed by oxyhemoglobin of the portion of the ear (the amounts of which can be determined based on the detected light at the photodector(s)/photosensor(s)). An oxygen concentration can then be calculated/detected, e.g., based on the ratio between the amount of light absorbed by deoxyhemoglobin and the amount of light absorbed by oxyhemoglobin. In some embodiments, the one or more LEDs includes at least one red and/or infrared LED for detecting a blood oxygen concentration of the wearer, and at least one green LED for detecting a pulse of the wearer. In some implementations, the determination of a blood oxygen concentration includes an adjustment to the detected signal (e.g., at the photodetector/photosensor) to correct for ambient or environmental light, such as sunlight. The adjustment can be based on an additional light sensor positioned, for example, on an outer surface of the wearable oxygen monitor. Such adjustments can be made, for example, when the wearable oxygen monitor is worn outdoors, in an environment with low lighting, and/or in an environment with a direct or indirect lighting source.

The memory can communicate with/via and/or store a software application that is compatible with one or more mobile devices (e.g., Windows, iOS, Android). The wearable oxygen monitor can be lightweight, power-efficient, and configured to communicate with one or more mobile devices and/or software application using one or more wireless communications protocols (e.g., Bluetooth®, 4G®, 5G®, etc.). The wearable oxygen monitor earpiece can include a power source that is rechargeable by a wired or wireless charging pod. The charging of the earpiece can occur when the earpiece is received at least partially within the charging pod and, optionally, when in electrical contact therewith.

In some embodiments, an emergency plan is activated in response to the wearer interacting with (e.g., pressing, tapping, sliding, etc.) the alert mechanism a predetermined number of times (e.g., once, twice, three times, four times, etc.) and/or with a predetermined frequency (e.g., three rapid taps within 1-5 seconds of each other). For example, a wearer pressing a button on the wearable oxygen monitor three times can trigger implementation/deployment of the emergency plan.

In some embodiments, a wearable oxygen monitor is configured to communicate connected (e.g., via wireless network communication) with a software application running on a mobile device (e.g., a smartphone, tablet, laptop computer, etc.) of a user/wearer of the wearable oxygen monitor or other individual. The software application can include code to cause storage of all vital records (e.g., blood oxygen level, heartrate/pulse, body temperature, hydration level, etc.) detected by one or more sensors onboard the wearable oxygen monitor, for example so that they can be sent to or shown to a medical provider. Alternatively or in addition, the software application can facilitate the definition/setting/customization, e.g., by a wearer/user of the wearable oxygen monitor or other authorized individual, of one or more set points or thresholds. The one or more set points or thresholds can include oxygen levels that will trigger an alert or alarm. Alternatively or in addition, the software application can facilitate the definition/setting/customization, e.g., by a wearer/user of the wearable oxygen monitor or other authorized individual, of one or more emergency contact telephone numbers to which an SMS message will be sent and/or that will be called when an alert/alarm is triggered.

In some embodiments, a wearable oxygen monitor includes a processor and a memory operably coupled to the processor. The memory stores instructions executable by the processor during operation. The instructions can include instructions to calculate an oxygen concentration, for example continuously and/or at predetermined intervals of time (e.g., every second, every 2 seconds, every 3 seconds, every 4 seconds, every 5 seconds, every 6 seconds, every 7 seconds, every 8 seconds, every 9 seconds, every 10 seconds, every 11 seconds, every 12 seconds, every 13 seconds, every 14 seconds, every 15 seconds, every 16 seconds, every 17 seconds, every 18 seconds, every 19 seconds, every 20 seconds, every 21 seconds, every 22 seconds, every 23 seconds, every 24 seconds, every 25 seconds, every 26 seconds, every 27 seconds, every 28 seconds, every 29 seconds, every 30 seconds, every 45 seconds, every minute, every 5 minutes, every 10 minutes, every 15 minutes, every 30 minutes, etc.).

The time interval can be configurable by a wearer/user of the wearable oxygen monitor and/or another authorized user, for example via a software application running on a mobile device of that individual and via wireless communication with the wearable oxygen monitor. In some implementations, the instructions include instructions to compare measured oxygen concentration levels (as measured by the wearable oxygen monitor) with a predetermined threshold value stored within the memory of the wearable oxygen monitor. The predetermined threshold value can be configurable by a wearer/user of the wearable oxygen monitor and/or another authorized user, for example via the software application.

In some embodiments, a wearable oxygen monitor is configured to emit an alarm sound and/or vibration in response to detecting that an oxygen level of a wearer/user is lower than a defined threshold value (e.g., representing an "alarm state"). An intensity, volume and/or frequency of the alarm sound and/or vibration can increase over time until the alarm is acknowledged by the wearer/user (e.g., via interaction of the wearer/user with an alert mechanism of the wearable oxygen monitor or via a graphical user interface (GUI) rendered by a software application of a mobile device of the wearer/user. Alternatively or in addition, an intensity, volume and/or frequency of the alarm sound and/or vibration can increase with and/or in proportion to an increase in a calculated difference between the detected oxygen level and the defined threshold value, such that the increasing intensity, volume and/or frequency of the alarm sound and/or vibration represents an increasing severity of the alarm state. Similarly, the intensity, volume and/or frequency of the alarm sound and/or vibration can decrease with and/or in proportion to a decrease in a calculated difference between the detected oxygen level and the defined threshold value, such that the increasing intensity, volume and/or frequency of the alarm sound and/or vibration represents a decreasing severity of the alarm state. The wearable oxygen monitor can terminate the alarm sound and/or vibration upon detection that a current oxygen level is equal to or greater than the defined threshold value.

In some embodiments, oxygen levels detected by (and, optionally, other sensor data gathered by/detected at) the wearable oxygen monitor are stored locally (e.g., within a memory of the wearable oxygen monitor) and/or are transmitted (e.g., via a transceiver of the wearable oxygen monitor) to a cloud-based server or other storage repository, for example using a software application. The wearable oxygen monitor, the cloud-based server and/or a software application associated with the wearable oxygen monitor can be configured to analyze sensor data collected/detected at the wearable oxygen monitor, for example to determine one or more conditions or biometric parameters based on the sensor data, to detect patterns associated with the sensor data over time, etc. Data stored locally and/or transmitted can include, in addition to the detected oxygen levels and optional other sensor data, information such as time and date of detection events associated with such data, an identifier of the earpiece, an identifier associated with the wearer, etc. Data stored at the cloud-based server can be downloaded therefrom by the wearer/user and/or other authorized person, for example to show a physician for purposes of diagnosis, investigation of anomalous events, etc. The ability of the wearer/user to download data from the cloud-based server can be limited, for example, to daily or weekly. Alternatively or in addition, a user may send a request to the cloud-based server, the request including a query specifying a range of dates for which he/she would like to retrieve data. Although described herein as pertaining to oxygen levels, systems and methods of the present disclosure can, alternatively or in addition, be used to detect other biometrics or vital signs, such as heartrate/pulse, body temperature, hydration level, salt level, etc.

In some embodiments, a mobile software application is configured for use with one or more wearable oxygen monitors of the present disclosure. The mobile software application can be compatible with one or more of Android, iOS and Windows, and can facilitate continuous communication between one or more mobile devices running the mobile software application and a wearable oxygen monitor (e.g., via one or more wireless sensors of the wearable oxygen monitor). The mobile software application can be configured to record/store detected vitals/biometric information (e.g., continuously, periodically, intermittently, and/or upon request or user interaction therewith) and, optionally, upload the detected data to a cloud-based storage for future reference. The mobile software application can be configured to send and/or receive a signal to cause display, e.g., in a GUI of a mobile device of the wearer/user, of one or more of the detected data values (and/or graphical representations thereof, for example over time), for example including oxygen levels, heart rate, etc. The mobile software application can be configured to identify and/or cause storage (e.g., in a database or other repository) of geometrics (e.g., geographic data such as GPS data) and/or barometrics (e.g., environmental data such as barometric pressure) in addition to the biometric information detected by the wearable oxygen monitor(s), and/or to track the occurrence of acute/emergency events over time (e.g., as indicated by the triggering of the emergency plan). Data received and/or stored by the software application can include crowd-sourced data (e.g., from multiple different wearable oxygen monitors associated with multiple different wearers, optionally without including identifying information associated with the individual wearers).

In some embodiments, data detected by one or more wearable oxygen monitors and information derived from such data is stored in a common repository and used to train a machine learning (ML) or artificial intelligence (AI) algorithm. The trained ML/AI algorithm can be used to predict future acute/emergency events (i.e., to perform predictive analytics), for example based on current (contemporaneous) sensor readings detected at the wearable oxygen monitor of a particular wearer. When a future acute/emergency event is predicted, an "early warning" alert can be generated and presented to a wearer/user (e.g., via a GUI of the wearer's mobile device, via the software application running thereon) such that the wearer/user can take remedial or preventative action (e.g., increase an oxygen intake).

Figure 1C:
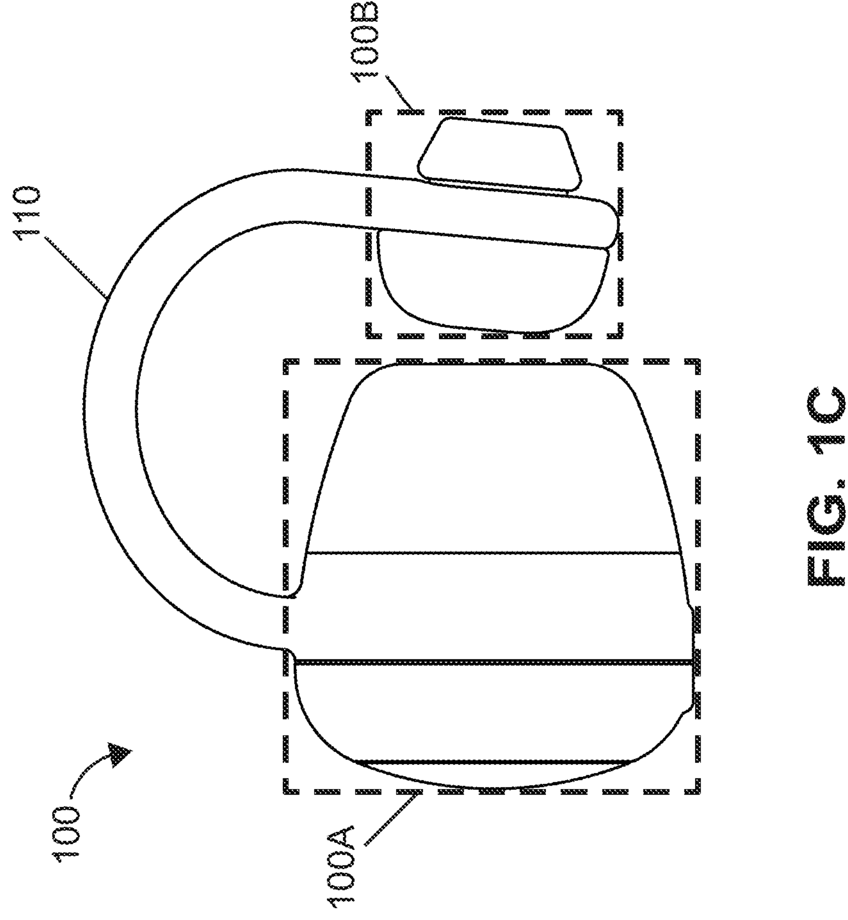

FIGS. 1A-1C are renderings of a wearable oxygen monitor 100, configured to be worn about a portion of an ear of a user, according to some embodiments. As shown in FIGS. 1A-IC, the wearable oxygen monitor 100 includes a first body portion 100A and a second body portion 100B, the first body portion 100A and the second body portion 100B mechanically coupled by a connection member 110. At least a portion of the first body portion 100A and the second body portion 100B may be integrally formed or monolithically formed with one another, for example from nylon, plastic, or another suitable material.

Figure 1D:
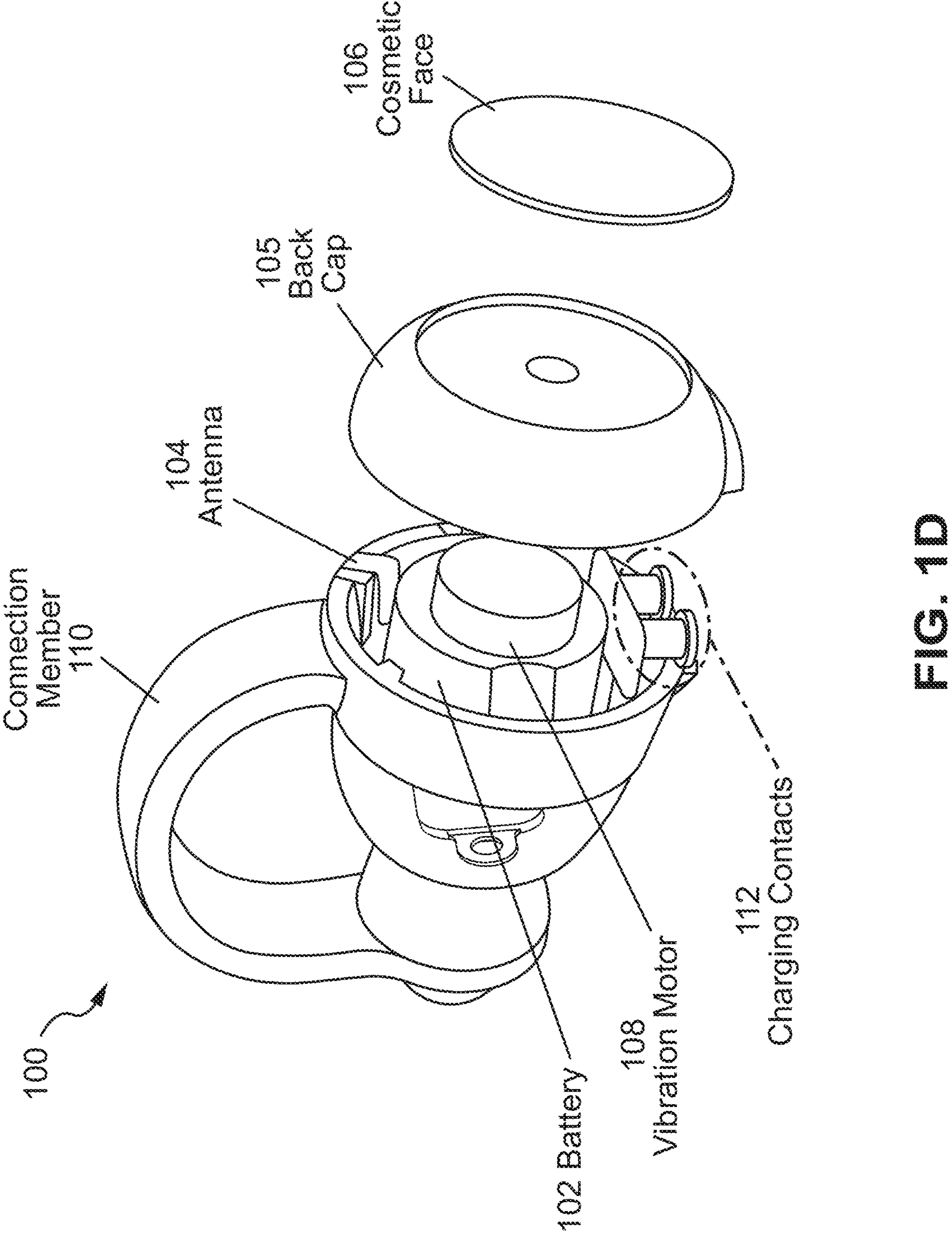
FIGS. 1D-1E are exploded-view renderings of the wearable oxygen monitor of FIGS. 1A-1C, showing components thereof.
Figure 1E:
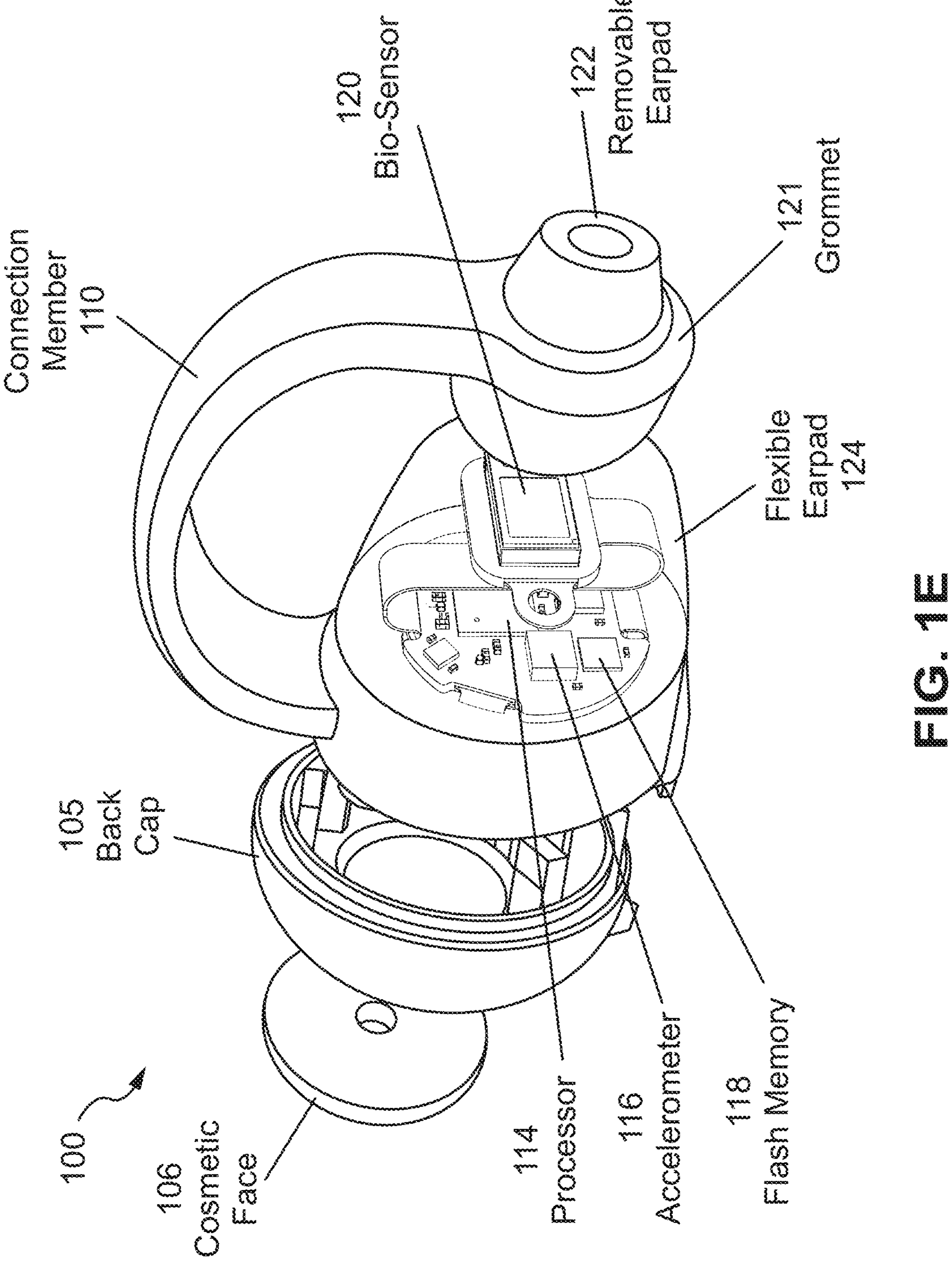

FIGS. 1D-1E are exploded-view renderings of the wearable oxygen monitor 100 of FIGS. 1A-1C, showing components thereof. For example, as shown in FIG. 1D, the wearable oxygen monitor 100 includes a battery 102, antenna 104, vibration motor 108, charging contacts 112, a back cap 105, and a cosmetic face 106. Each of the battery 102, antenna 104, vibration motor 108, charging contacts 112, back cap 105, and cosmetic face 106 can be contained within and/or attached to the first body portion (i.e., 100A of FIGS. 1A-1C). FIG. 1E is a view from a different perspective relative to FIG. 1D, and shows additional components of the first body portion-namely a processor 114, an accelerometer 116, a flash memory 118, a bio-sensor 120, and a flexible earpad 124. FIG. 1E also shows that the second body portion includes a grommet 121 and a removable earpad 122 positioned within the grommet 121.

Figures 1F, 1G:
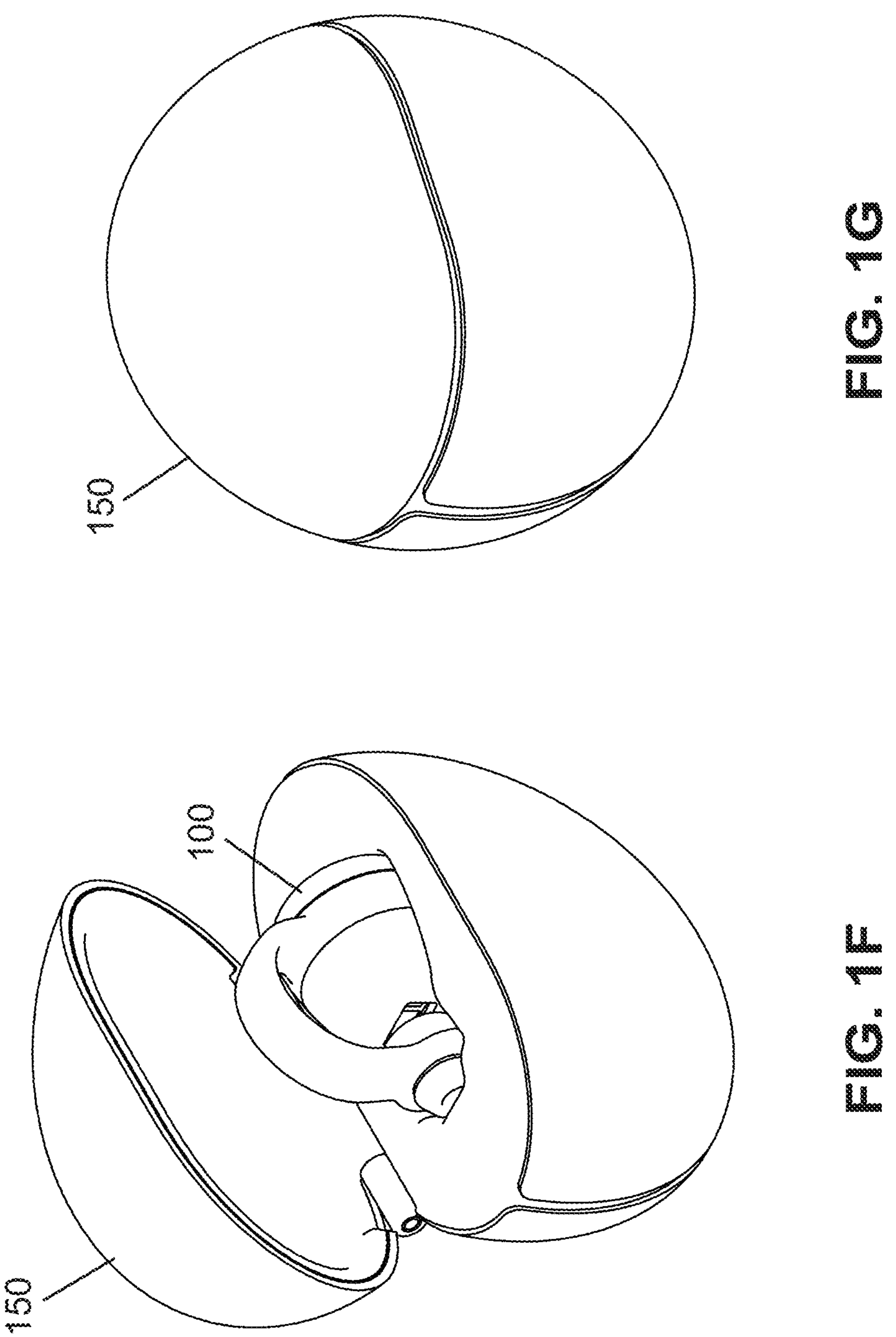
FIGS. 1F-1J are renderings of the wearable oxygen monitor of FIGS. 1A-1C and a charger case for the wearable oxygen monitor of FIGS. 1A-1C.
Figures 1H, 1I:
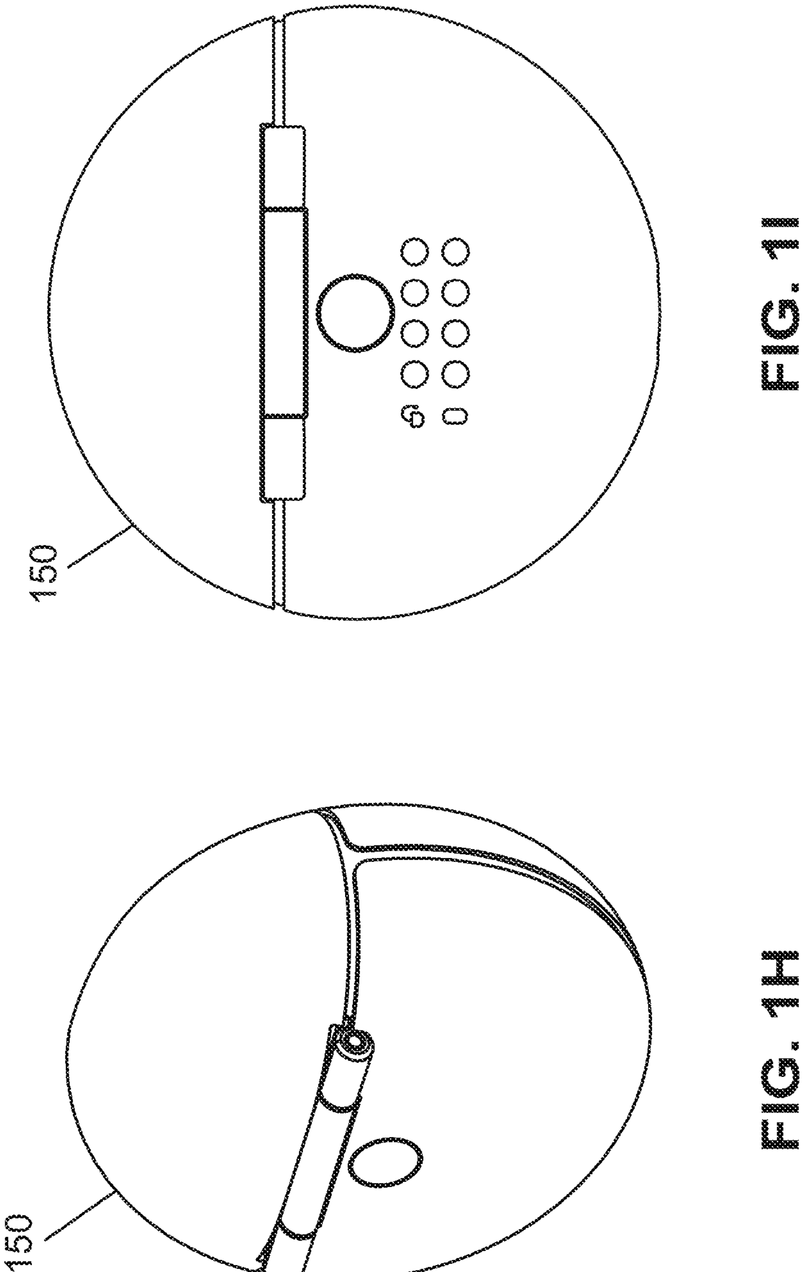
Figure 1J:
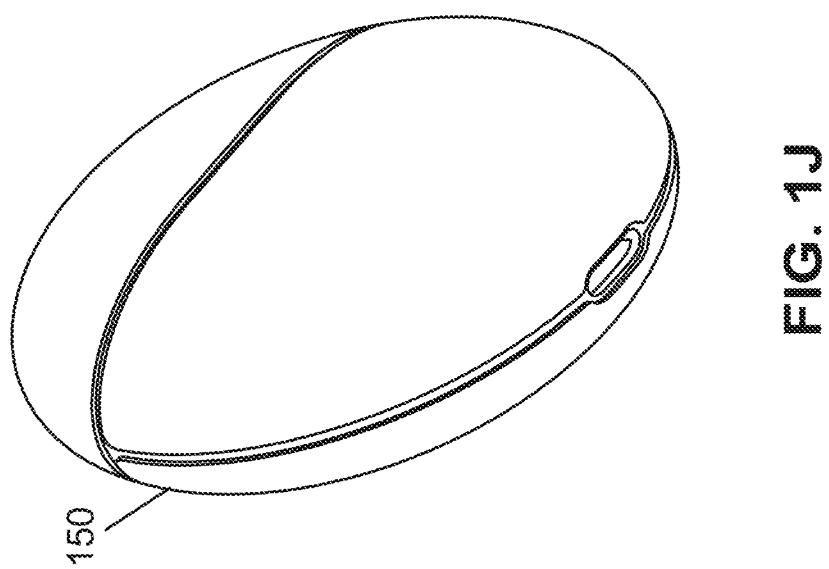

FIGS. 1F-1J are renderings of the wearable oxygen monitor of FIGS. 1A-1C and a charger case 150 for the wearable oxygen monitor of FIGS. 1A-IC. The charger case 150 has a lower/base portion and a lid portion, the base and lid portions coupled to one another by a hinge. As shown in FIG. 1F, the wearable oxygen monitor 100 fits within a complementary-shaped recess in the charger case 150, and is partially received therein. In other words, when positioned inside the charger case 150, a first portion of the wearable oxygen monitor 100 sits within the recess, and a second portion of the wearable oxygen monitor 100 is positioned within a recess defined by the lid of the charger case 150

Figure 2A:
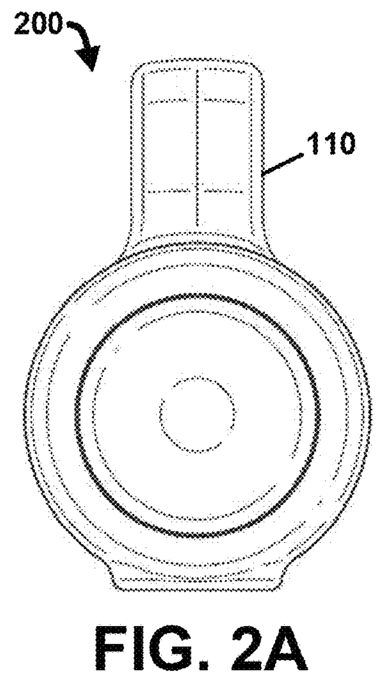
Figure 2B:
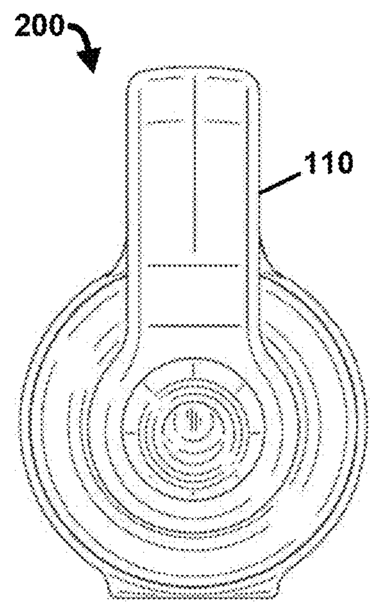
Figure 2C:
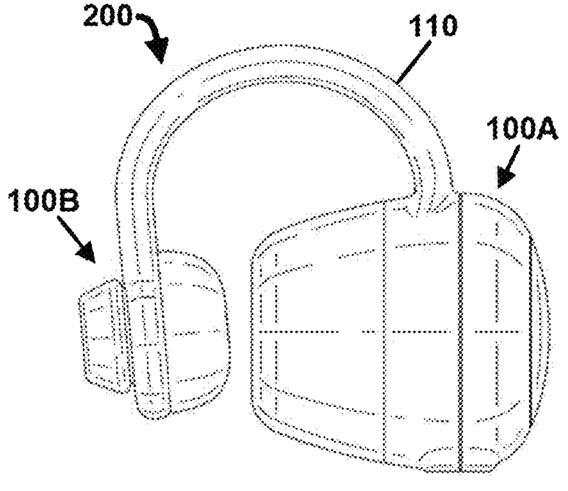
Figure 2D:
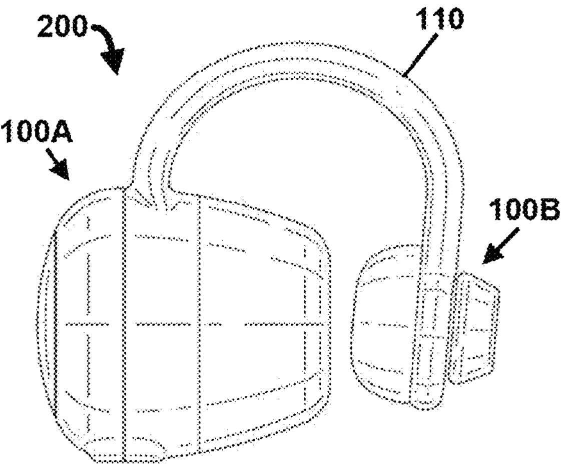
Figure 2E:
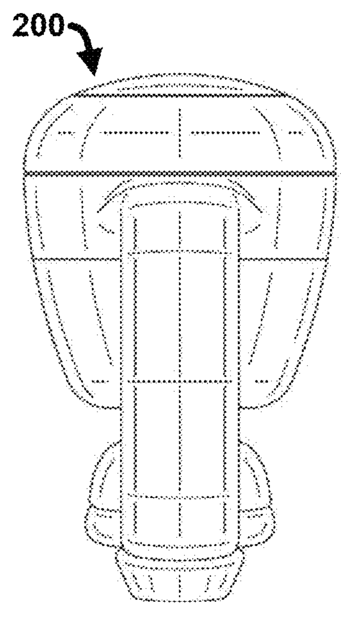
Figure 2F:
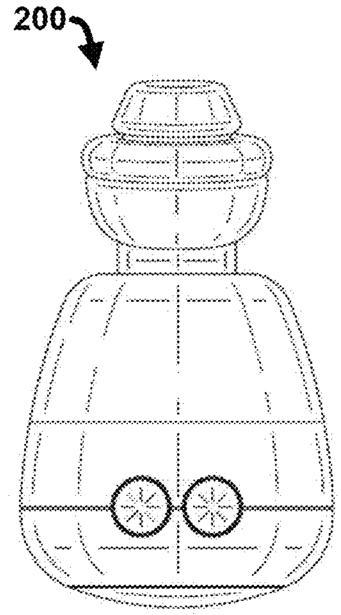
Figure 2G:
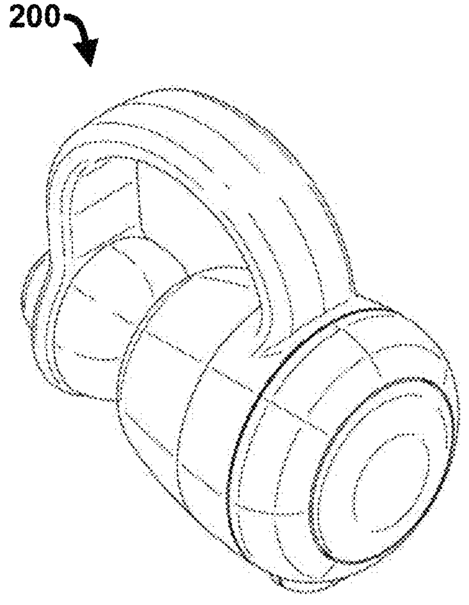
Figure 2H:
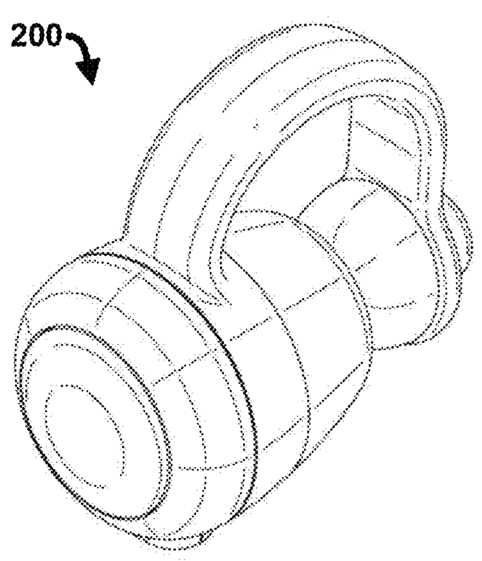
Figure 2I:
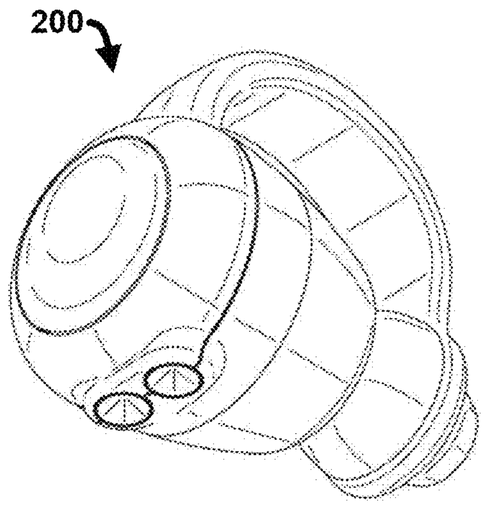
Figure 2J:
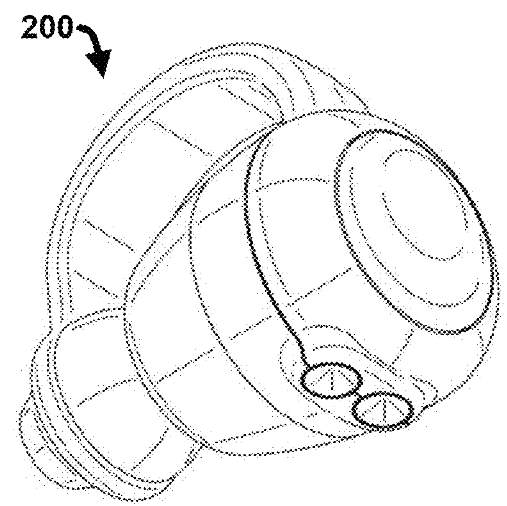
Figure 2K:
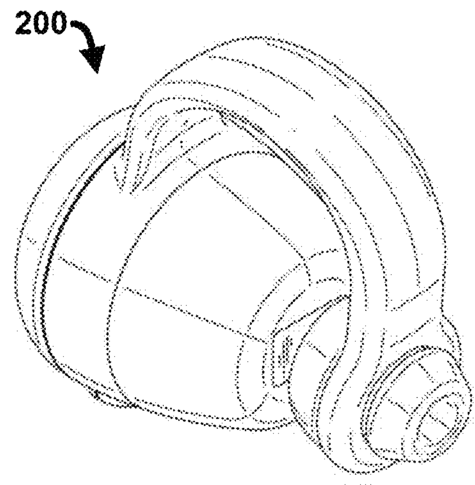
Figure 2L:
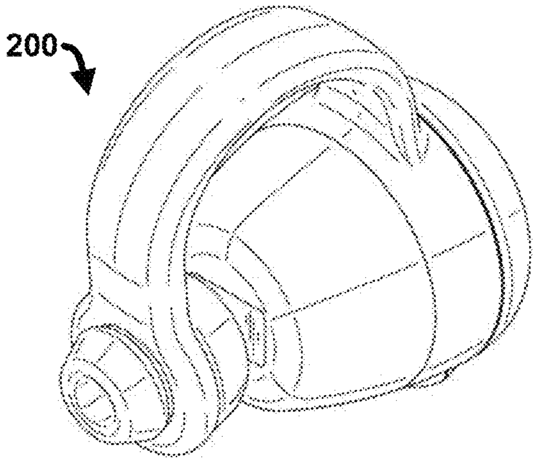
Figures 2M, 2N, 2O, 2P:
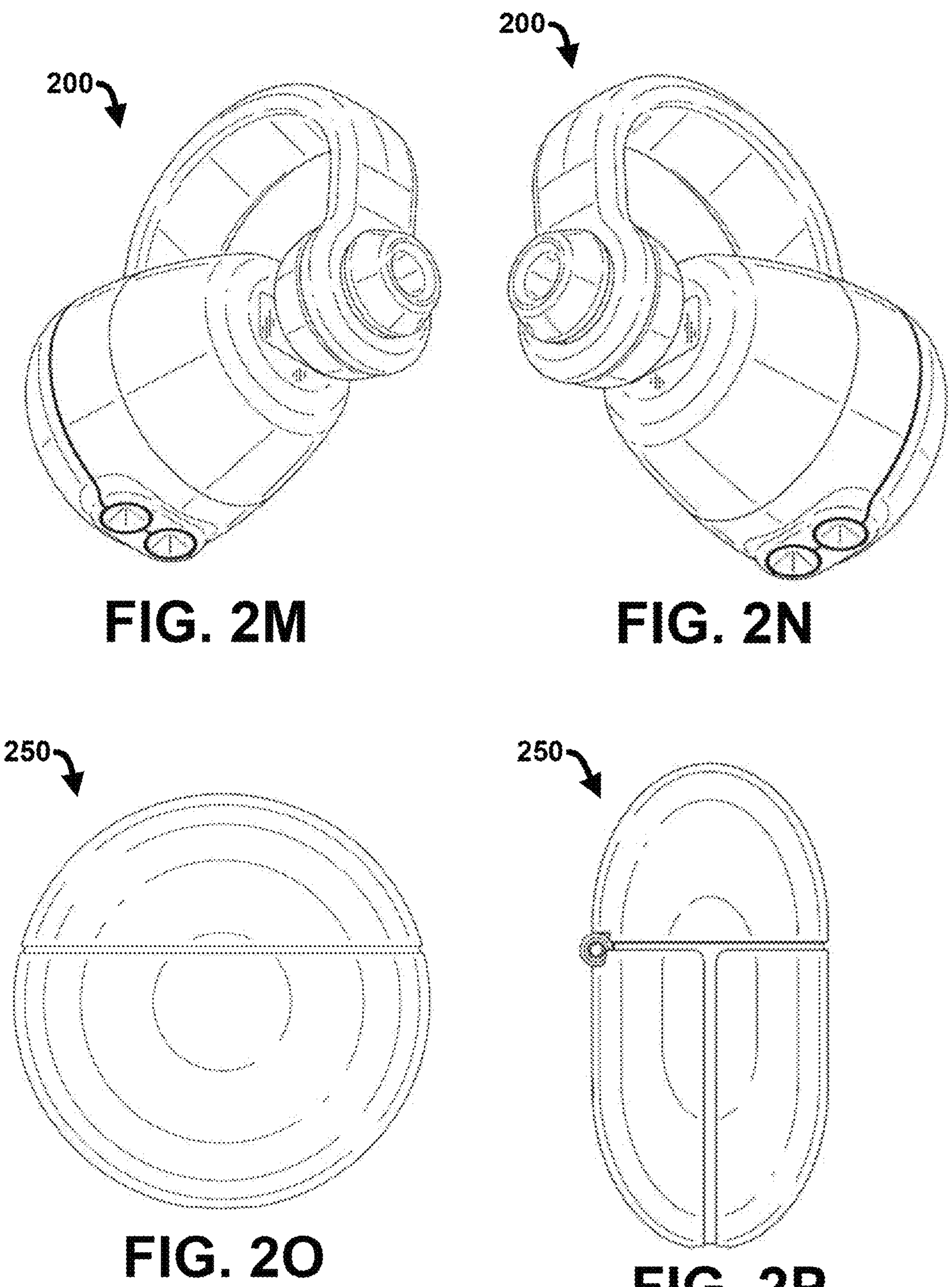
Figures 2U, 2V, 2W, 2X:
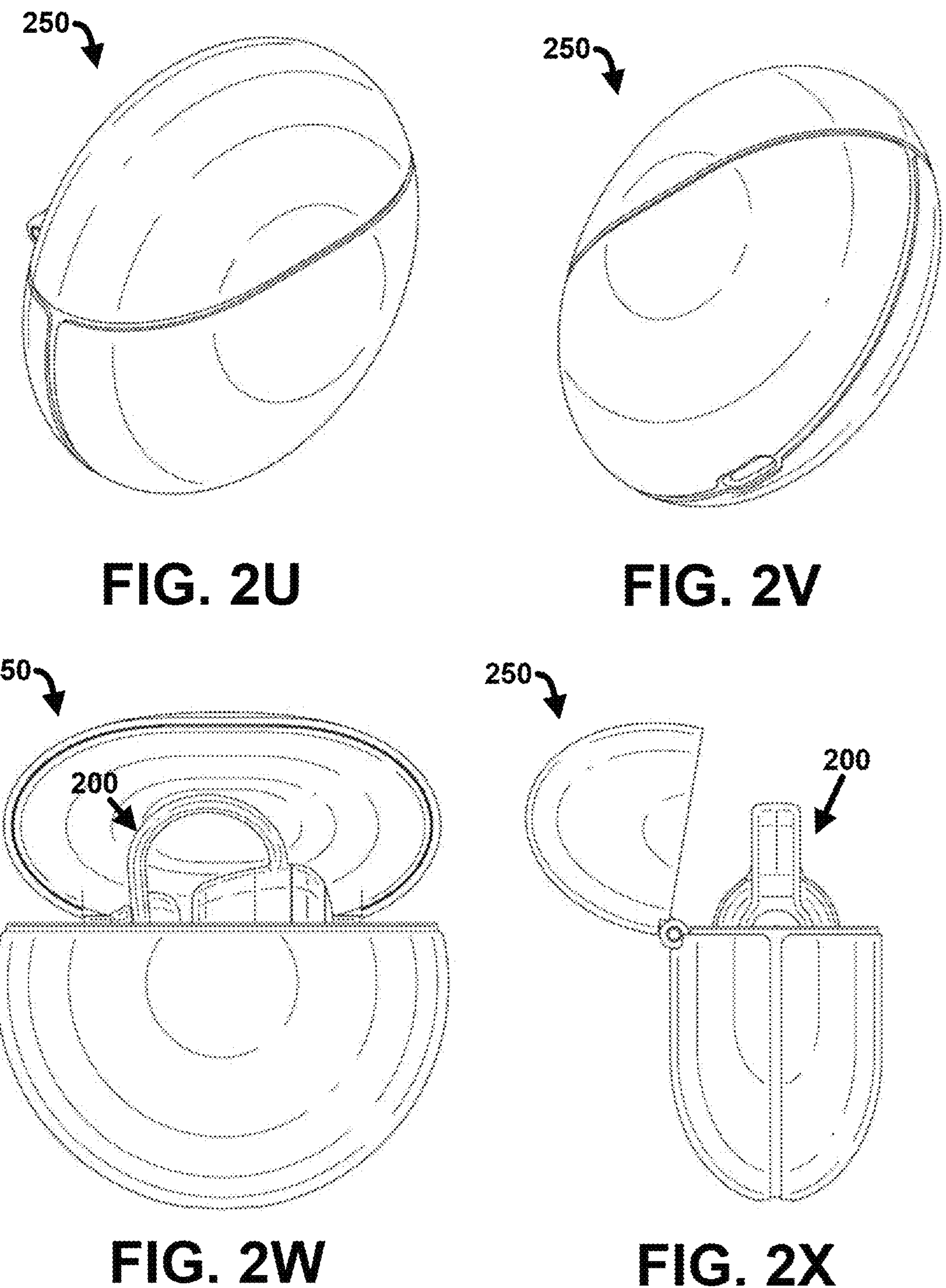
Figure 2A:
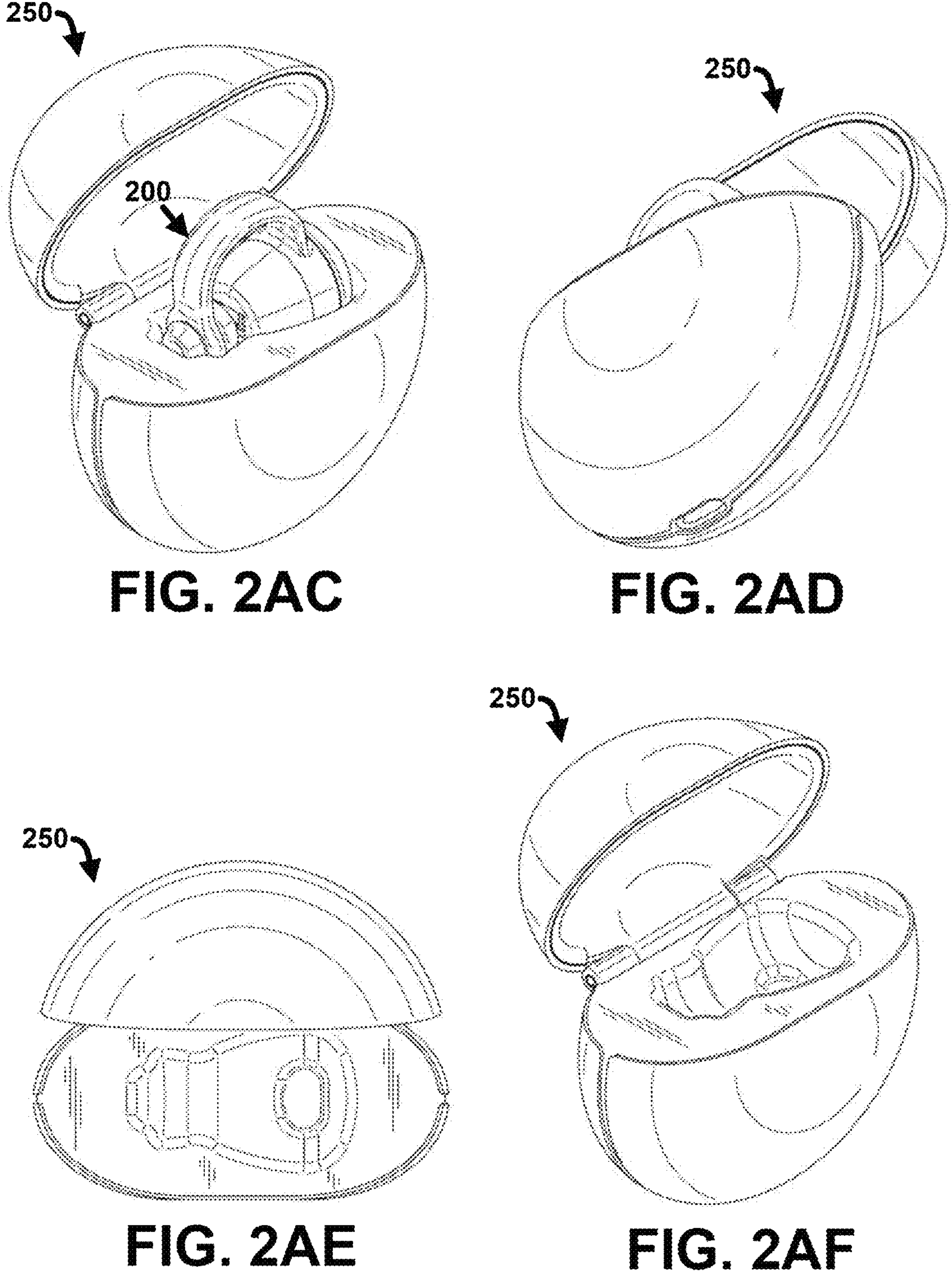
Figure 2A:
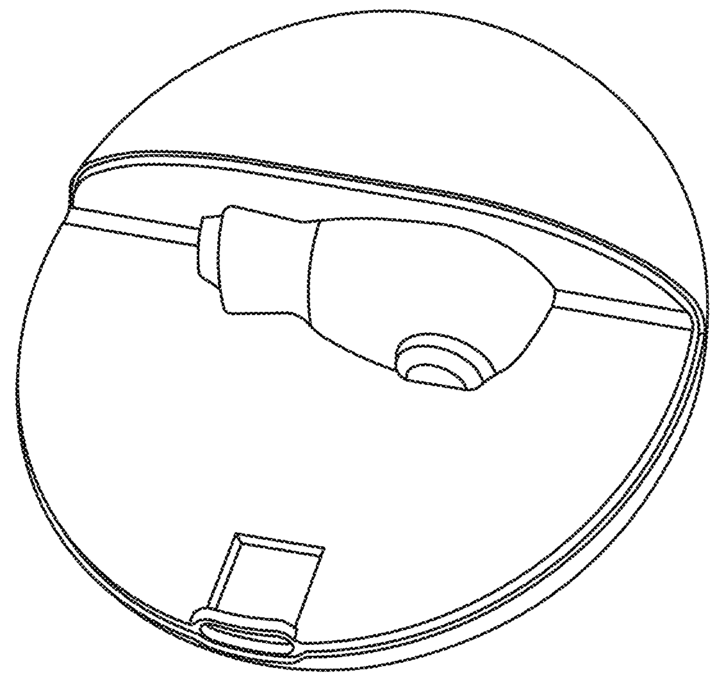

FIGS. 2A-2N are drawings of a wearable oxygen monitor 200, configured to be worn about a portion of an ear of a user, according to some embodiments. FIGS. 2O-2V are drawings of a charger case in a closed configuration, the charger case configured to contain, and to supply power to, the wearable oxygen monitor of FIGS. 2A-2N, according to some embodiments. FIGS. 2W-2AD are drawings of the charger case of FIGS. 2O-2V in an open configuration, the charger case containing the wearable oxygen monitor of FIGS. 2A-2N. FIGS. 2AE-2AF are drawings of the charger case of FIGS. 2O-2V in an open configuration and not containing a wearable oxygen monitor. FIG. 2AG is a rendering of a charger case with a panel removed to show an underlying shape of a recess/pocket configured to receive a wearable oxygen monitor, according to some embodiments.

Figure 3:
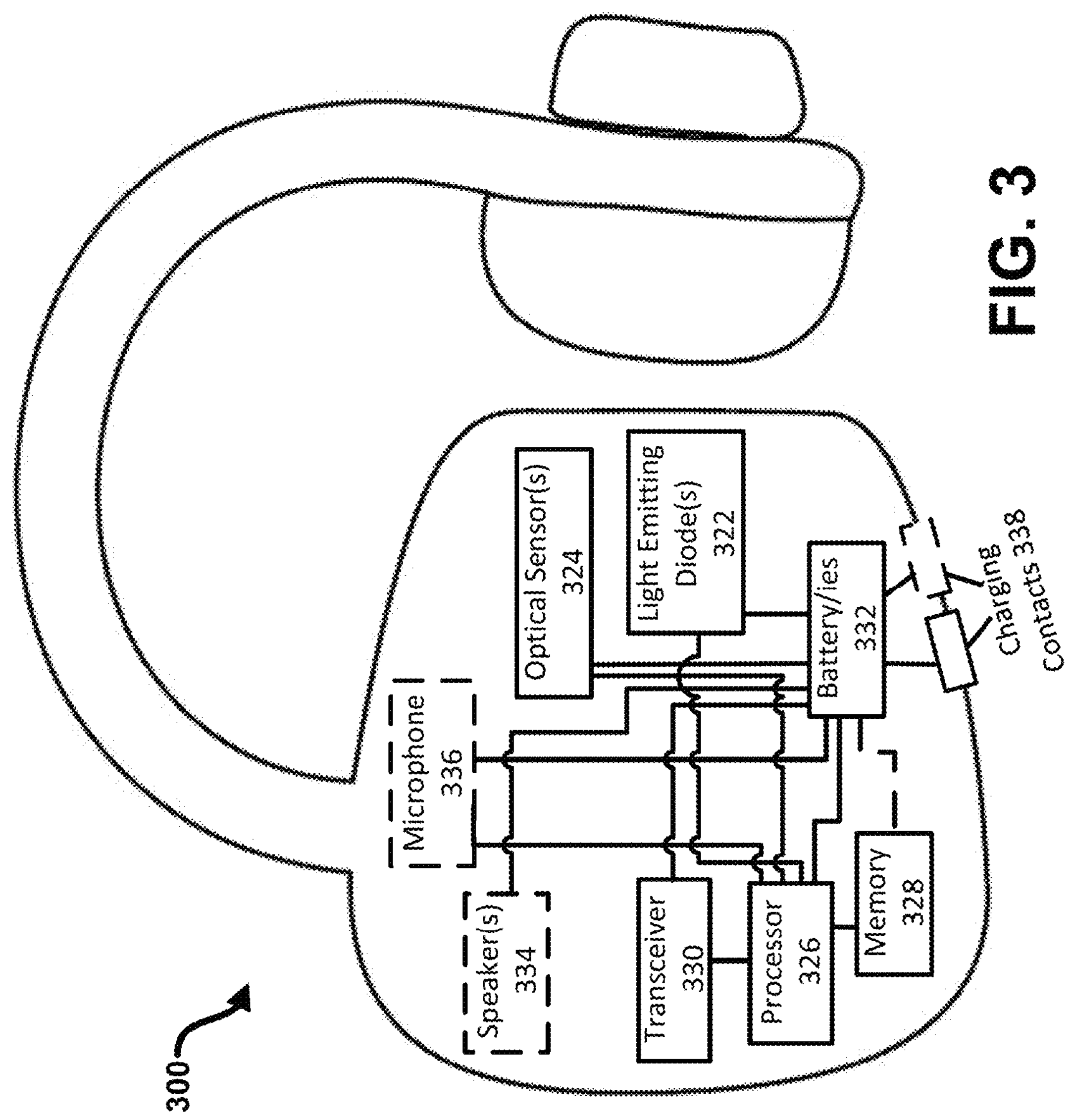
FIG. 3 is a schematic drawing showing components of a wearable oxygen monitor, according to some embodiments.

FIG. 3 is a schematic drawing showing components of a wearable oxygen monitor 300, according to some embodiments. As shown in FIG. 3, the wearable oxygen monitor 300 includes a memory 328, a processor 326, a transceiver 330, one or more batteries or other power sources 332, one or more LEDs 322 (optionally in a row or array), one or more optical sensors 324, and optionally one or more speaker(s) 334 and/or a microphone 336. The one or more batteries 332 are electrically coupled to, and configured to supply power to, each of the processor 326, the transceiver 330, the LED(s) 322, the optical sensor(s) 324, the optional speaker(s) 334, the optional microphone 336, and optionally the memory 328. The processor 326 is operably coupled to each of the memory 328, the LED(s) 322, the optical sensor(s) 324, the transceiver 330, and the optional microphone 336.

The wearable oxygen monitor 300 optionally includes an alert mechanism (e.g., an actuatable button) that is electrically connected to the one or more batteries 332 and is operably coupled to at least one of the processor 326 and the transceiver 330. The transceiver 330 can be configured to send and/or receive communications (e.g., to/from a remote compute device such as a mobile device of a wearer/user of the wearable oxygen monitor 300 or other authorized person), for example including data gathered/detected by the one or more optical sensor(s) 324 and/or the processor 326, and/or stored in the memory 328. The processor 326 can be configured to control (e.g., based on processor-executable instructions stored in the memory 328 and/or received via the transceiver 330) at least one of the one or more LEDs 322, the microphone 336, the speaker 334, or the one or more batteries 332, via an electrical conduit (not shown). During operation, and when worn about a portion of an ear of the wearer/user, the one or more LEDs 322 emit light such that the emitted light is reflected by a portion (e.g., a surface or surface layer) of the ear in a direction toward the one or more optical sensors 324. The one or more optical sensors 324 detect a signal in response to the reflected light. In some implementations, the processor 326 determines an oxygen level of the wearer based on the detected signal and, optionally, stores the determined oxygen level in the memory 328, optionally with date information, time information, and/or other sensor data detected based on one or more other sensors (not shown) onboard the wearable oxygen monitor 300. Alternatively or in addition, raw data including the detected signal (optionally with data detected using the one or more other sensors) can be sent, via the processor 326 and using the transceiver 330, to a remote compute device such as a cloud-based server, a remote mobile device, etc., for determination of an oxygen level based on the raw data.

Figure 4:
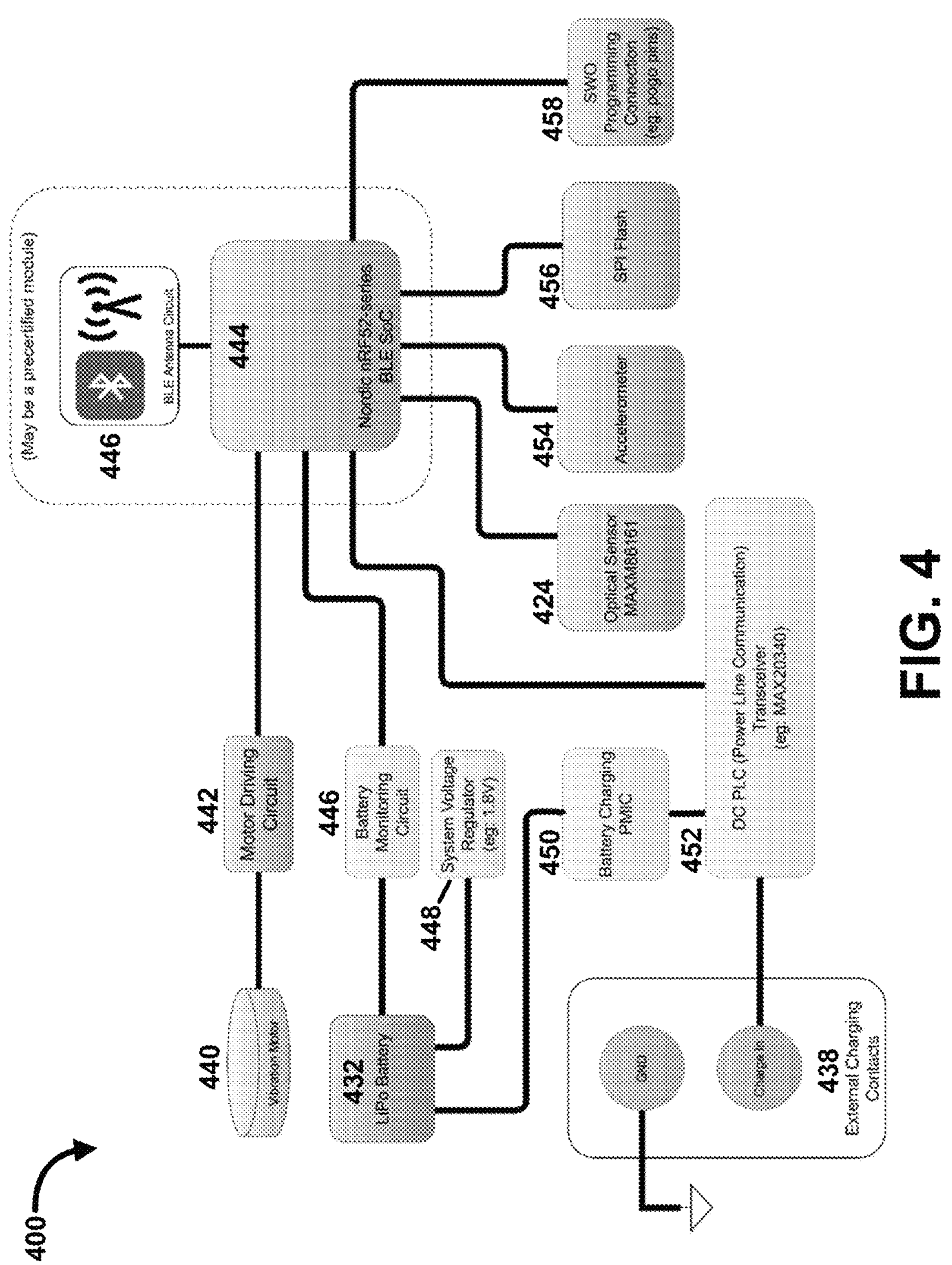
FIG. 4 is a block diagram showing components of a wearable oxygen monitor, according to some embodiments.

FIG. 4 is a block diagram showing components of a wearable oxygen monitor 400 (such as the wearable oxygen monitor shown in FIGS. 1A-1E and/or 2A-2N), according to some embodiments. As shown in FIG. 4, the wearable oxygen monitor 400 includes a vibration motor 440 operatively coupled to a motor driving circuit 442, a battery (e.g., lithium polymer ("LiPo")) 432 operatively coupled to a battery monitoring circuit 446, a system voltage regulator (e.g., 1.8V) 448, and a battery charging power management integrated circuit ("PMIC") 450. The battery charging PMIC 450 is operatively coupled to a direct current ("DC") power line communication ("PLC") transceiver (e.g., a MAX20340) 452. Each of the DC PLC transceiver 452, the battery monitoring circuit 446, and the motor driving circuit 442 is operatively coupled to a system-on-a-chip ("SoC") (e.g., a Nordic nRF52-series) 444, which in turn is operatively coupled to an antenna 446 (e.g., a Bluetooth® ("BLE") antenna circuit). The DC PLC transceiver 452 is also operatively coupled to a "charge in" external charging contact from a pair of external charging contacts 438 which also includes a ground contact. The SOC 444 is operatively coupled to one or more optical sensors 424, an accelerometer 454, a serial peripheral interface ("SPI") flash memory 456, and a serial wire output ("SWO") programming connection (e.g., pogo pins) 458.

Figure 5:
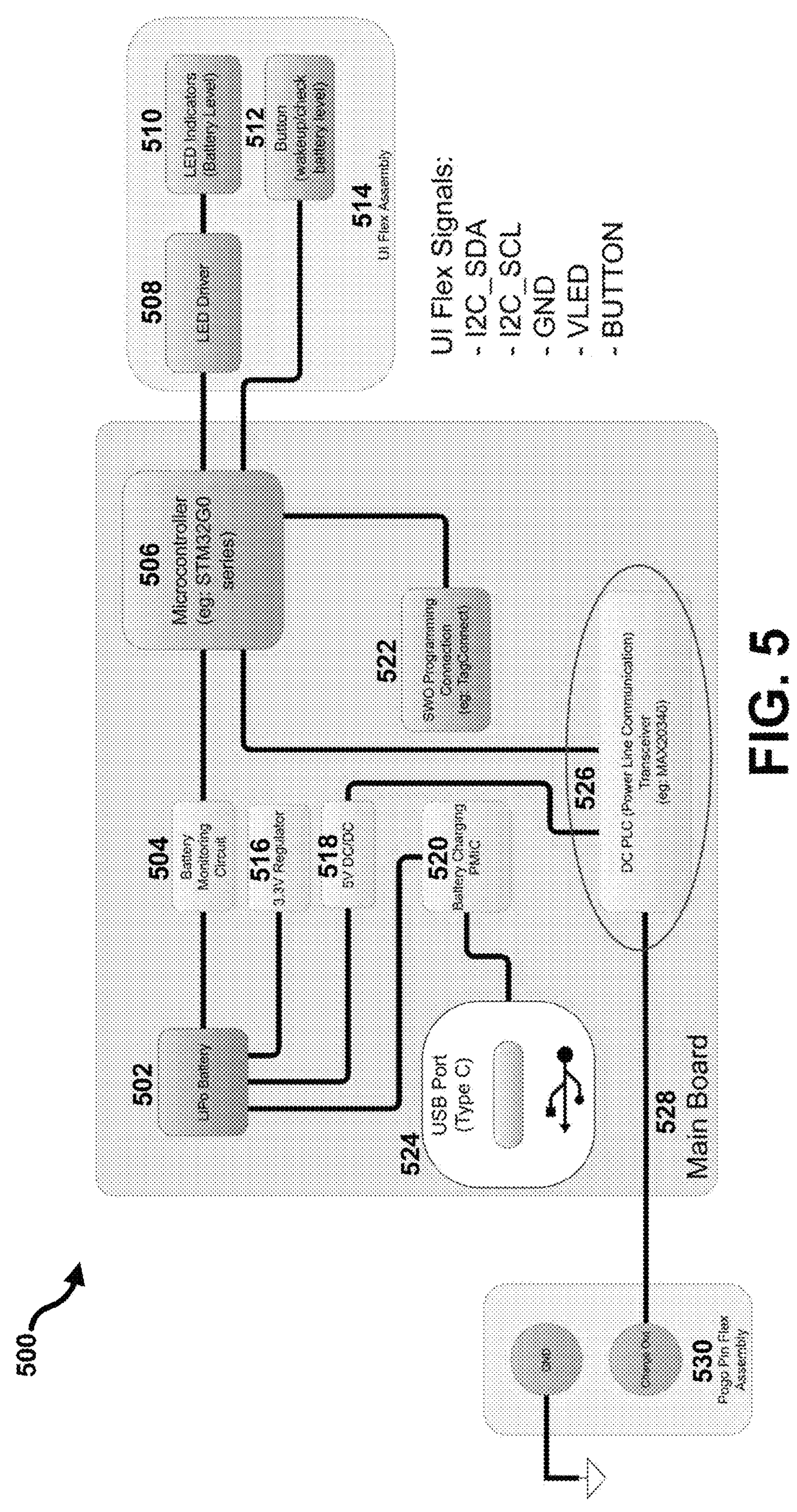
FIG. 5 is a block diagram showing components of a charger case, according to some embodiments.

FIG. 5 is a block diagram showing components of a charger case 500 (such as the charger case shown in FIGS. 2O-2AF), according to some embodiments. As shown in FIG. 5, the charger case 500 includes a battery 502 (e.g., a LiPo battery), which is operatively coupled to each of a battery monitoring circuit 504, a regulator 516 (e.g., 3.3V), a DC-to-DC converter 518, and a battery charging PMIC 520. The battery monitoring circuit 504 is operatively coupled to a microcontroller 506 (e.g., a STM32G0 series microcontroller), which in turn is operatively coupled to each of a DC PLC transceiver 526 (e.g., a MAX20340), a SWO programming connection 522 (e.g., TagConnect), a LED driver 508, and a button 512 or other actuator 512 (e.g., to trigger "wakeup" of the charger case and/or to check a battery power level). The LED driver 508 is operatively coupled to one or more LED indicators 510 (e.g., to indicate battery level, for example based on color of illumination and/or illumination status). The battery charging PMIC 520 is operatively coupled to a universal serial bus (USB) 524 (e.g., type C), and the DC PLC 526 is operatively coupled to a "charge out" contact from a pair of contacts 530, which also includes a ground contact. The pair of contacts 530 may be configured to mechanically mate with, and electrically couple to, the external charging contacts 438 of the wearable oxygen monitor 400 of FIG. 4.

Figure 6:
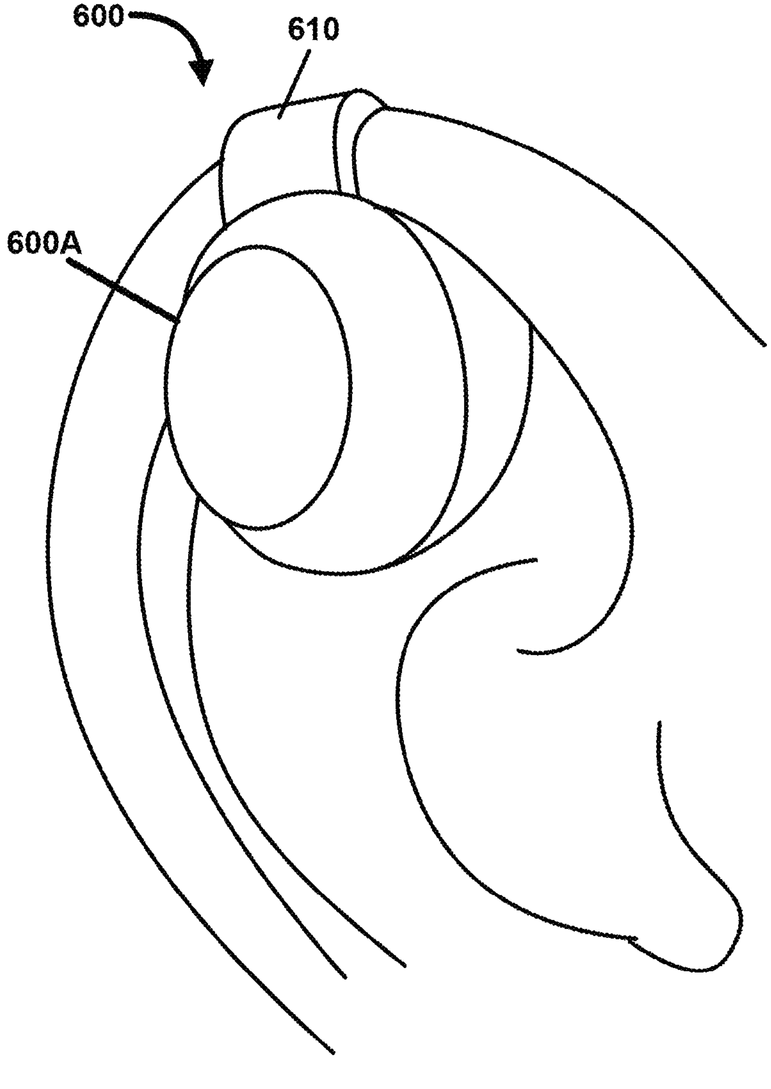
FIG. 6 is a drawing of a wearable oxygen monitor when worn about an upper portion of an ear of a user/wearer, according to an embodiment.

FIG. 6 is a drawing of a wearable oxygen monitor 600 when worn about an upper portion of an ear of a user/wearer, with a first body portion 600A and connection member 610 visible, according to an embodiment. The connection member 610 can be made of nylon, plastic, or any other suitable material. Although shown in FIG. 6 as being positioned about the upper portion of the ear, the wearable oxygen monitor 610 may alternatively be positioned on the ear lobe or on any other portion of the ear. For example, the wearable oxygen monitor 600 can be positioned about the helix, scapha, pinna, or earlobe of the ear. During placement or "donning" of the wearable oxygen monitor 600, a gap between the first body portion 600A and a second body portion of the wearable oxygen monitor 600 can be expanded by, e.g., by moving the first body portion and the second body portion away from one another, expanding the radius of curvature of the connecting member 610, and/or deforming the connecting member 610. Once positioned on the portion of the ear of the user (a "second configuration"), and external force(s) are removed from the wearable oxygen monitor 600, the first body portion 600A and the second body portion may naturally move a distance, equal to a portion of the gap, toward one another, e.g., by virtue of a shape memory or an inherent spring force (or bias force) of the connecting member 610, such that the wearable oxygen monitor 600 remains securely positioned on the portion of the ear of the user during use (e.g., during movement of the user).

Figure 7A:
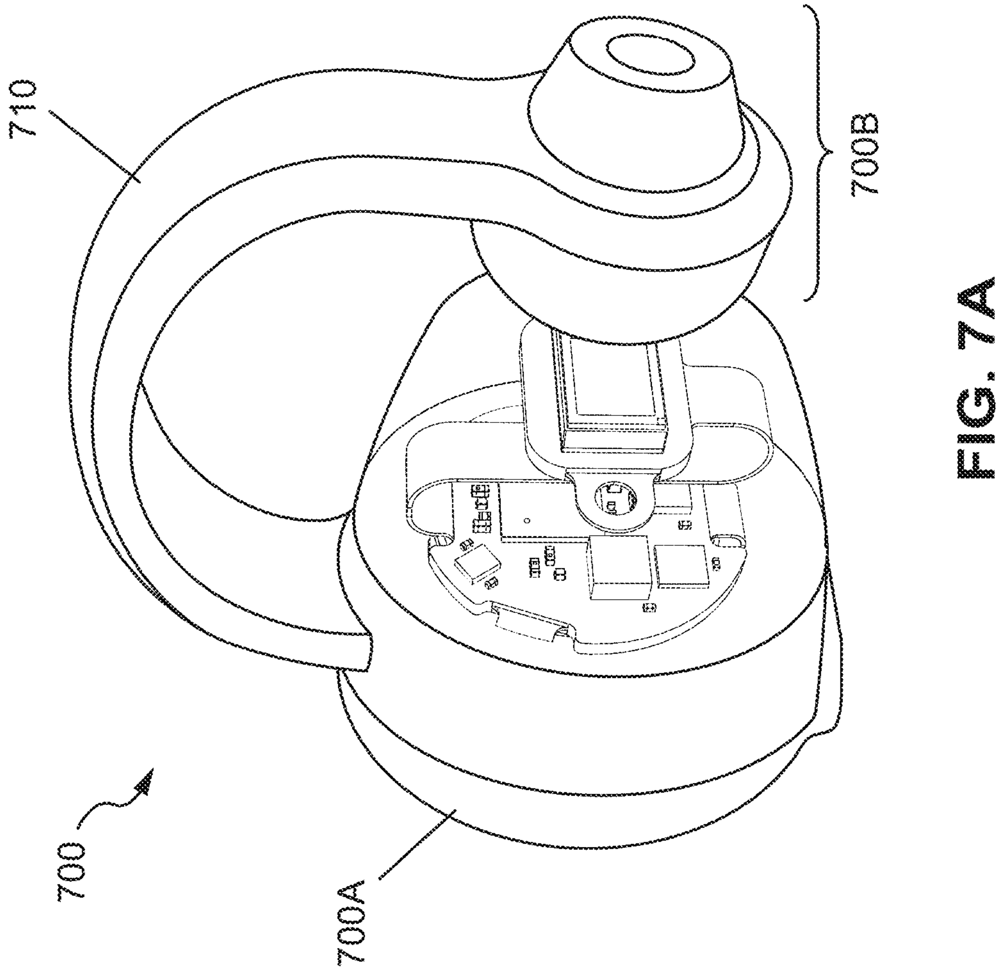
FIGS. 7A-7C are renderings of a wearable oxygen monitor, configured to be worn about a portion of an ear of a user, at various stages of assembly and showing components thereof, according to some embodiments.
Figure 7B:
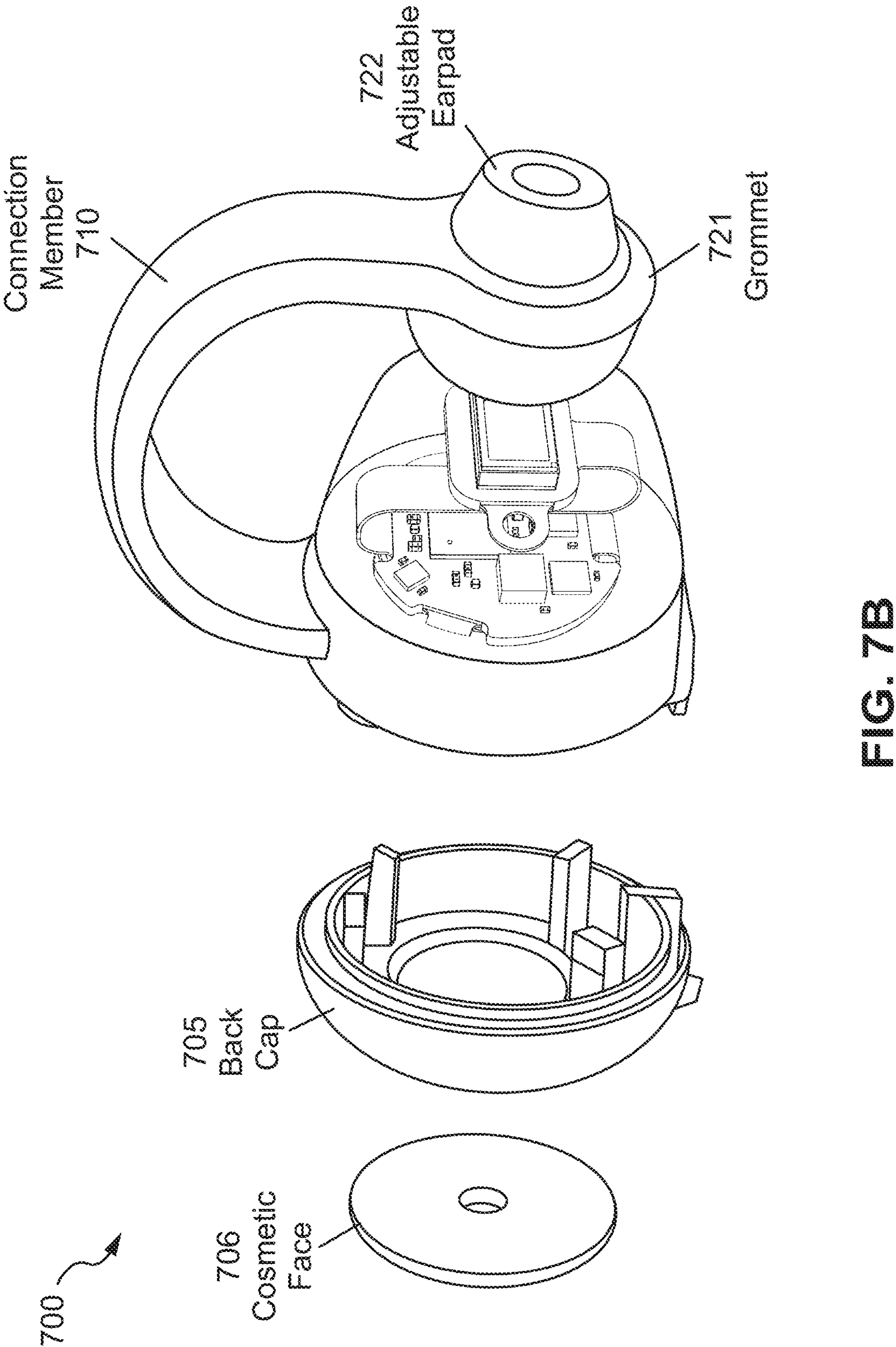
Figure 7C:
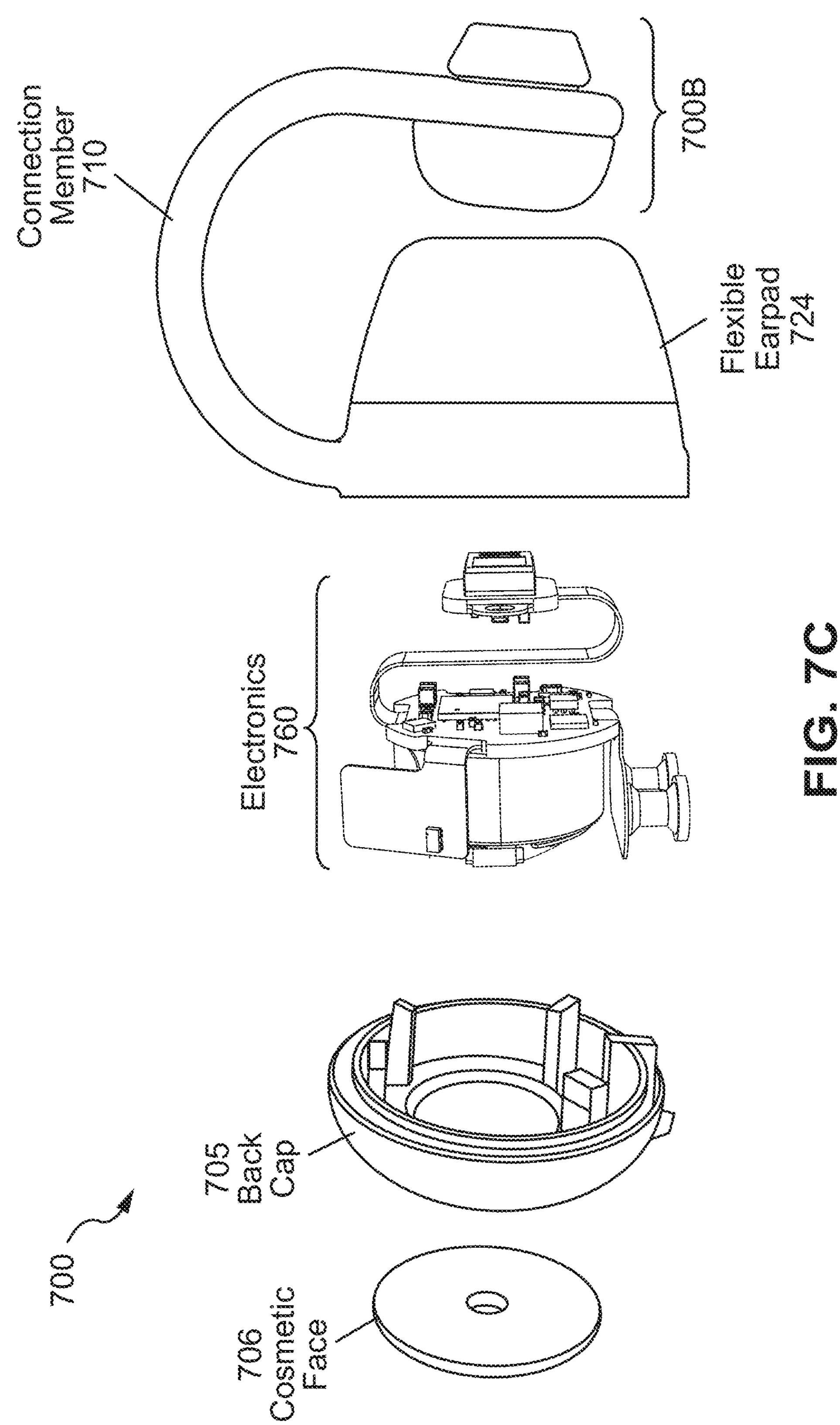

FIGS. 7A-7C are renderings of a wearable oxygen monitor 700, configured to be worn about a portion of an ear of a user, at various stages of assembly and showing components thereof, according to some embodiments. As shown in FIG. 7A, the wearable oxygen monitor 700 includes a first body portion 700A and a second body portion 700B, the first body portion 700A and the second body portion 700B mechanically coupled by a connection member 710. FIGS. 7B-7C show that the wearable oxygen monitor 700 includes a cosmetic face 706, a back cap 705, a connection member 710 connecting the first body portion and the second body portion 700B, electronics 760 (e.g., including some or all of the electronic components shown in FIGS. 3-4), a flexible earpad 724, a grommet 721, and an adjustable earpad 722.

Figure 8B:
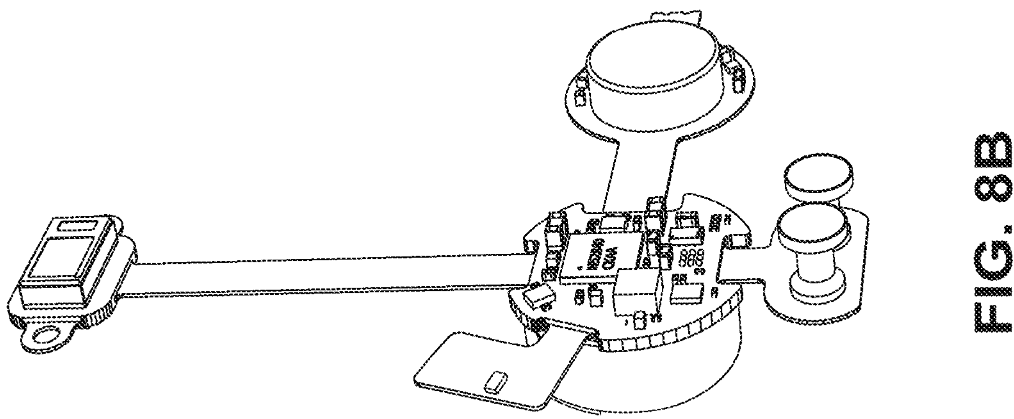
FIGS. 8A-8U are renderings of a flexible electronics assembly for a wearable oxygen monitor, according to some embodiments.
Figure 8A:
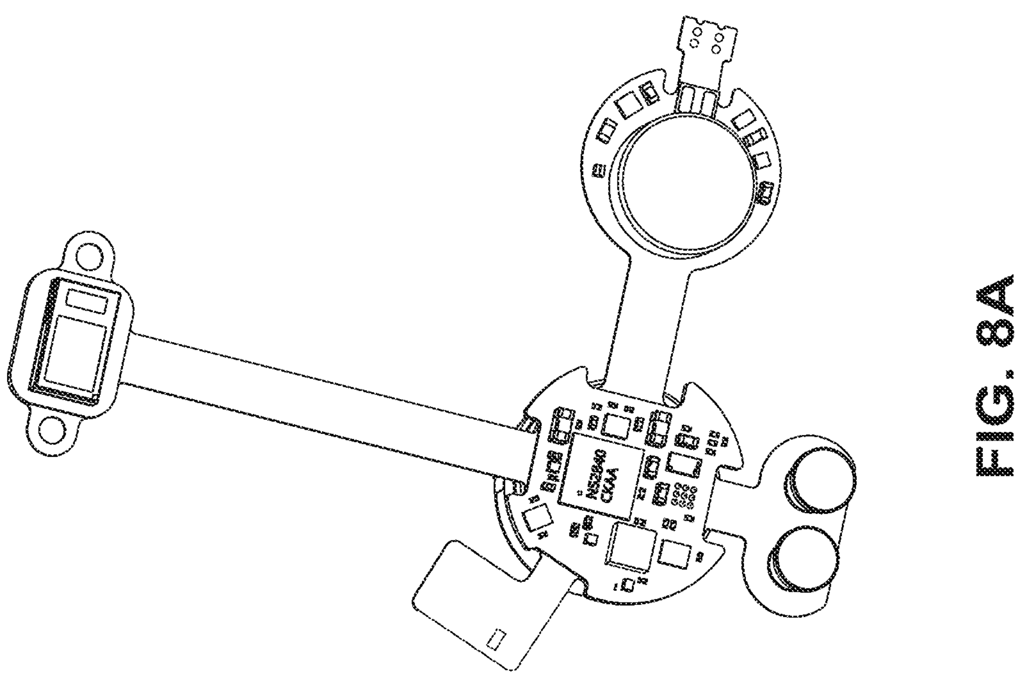
Figure 8D:
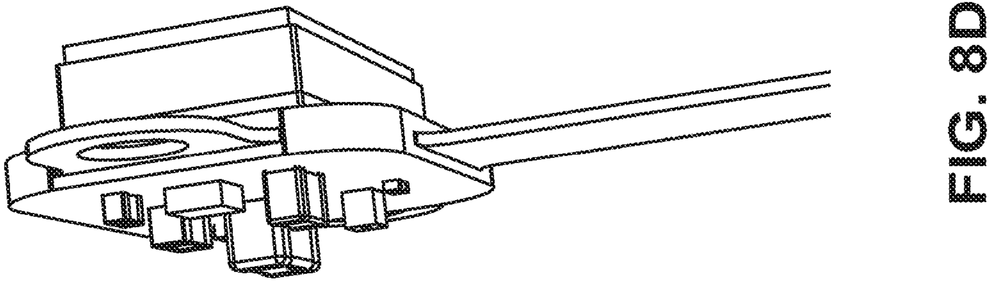
Figure 8C:
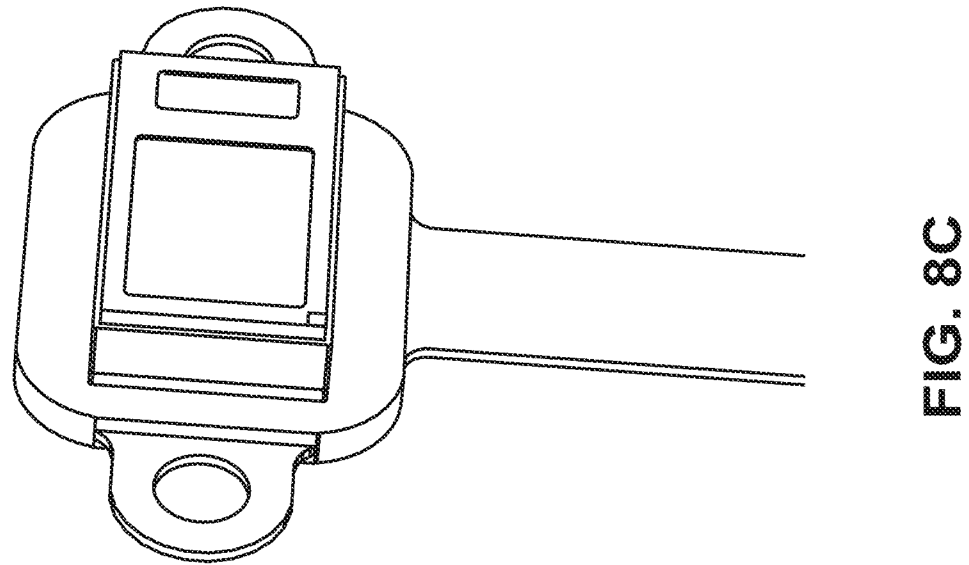
Figure 8F:
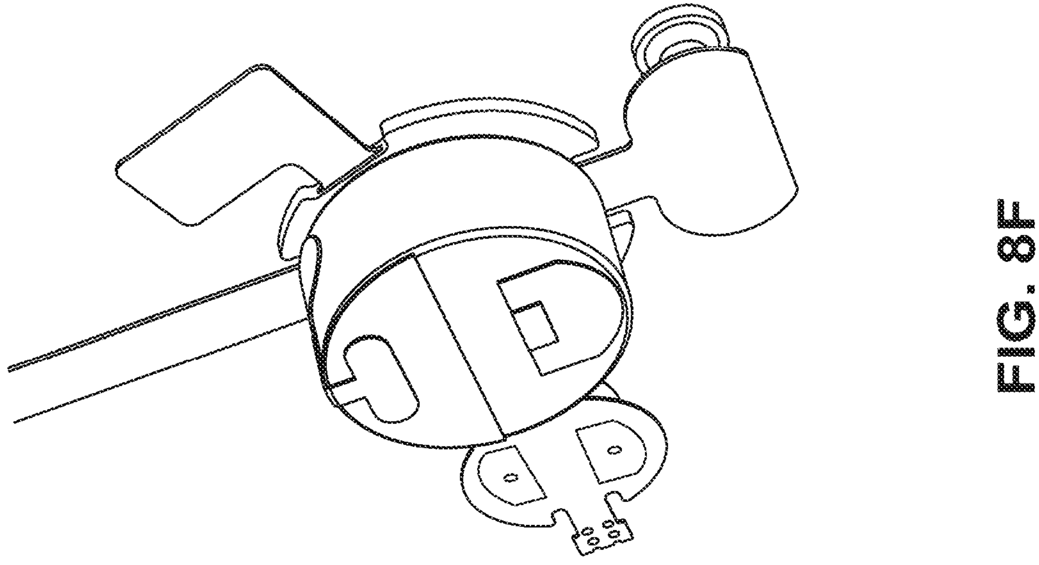
Figure 8E:
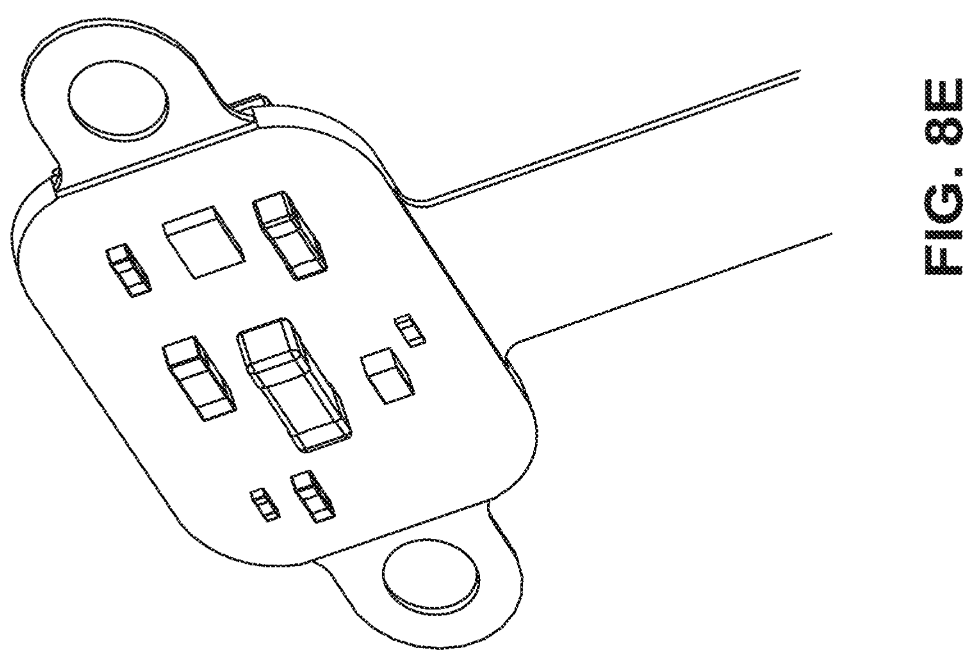
Figures 8G, 8H:
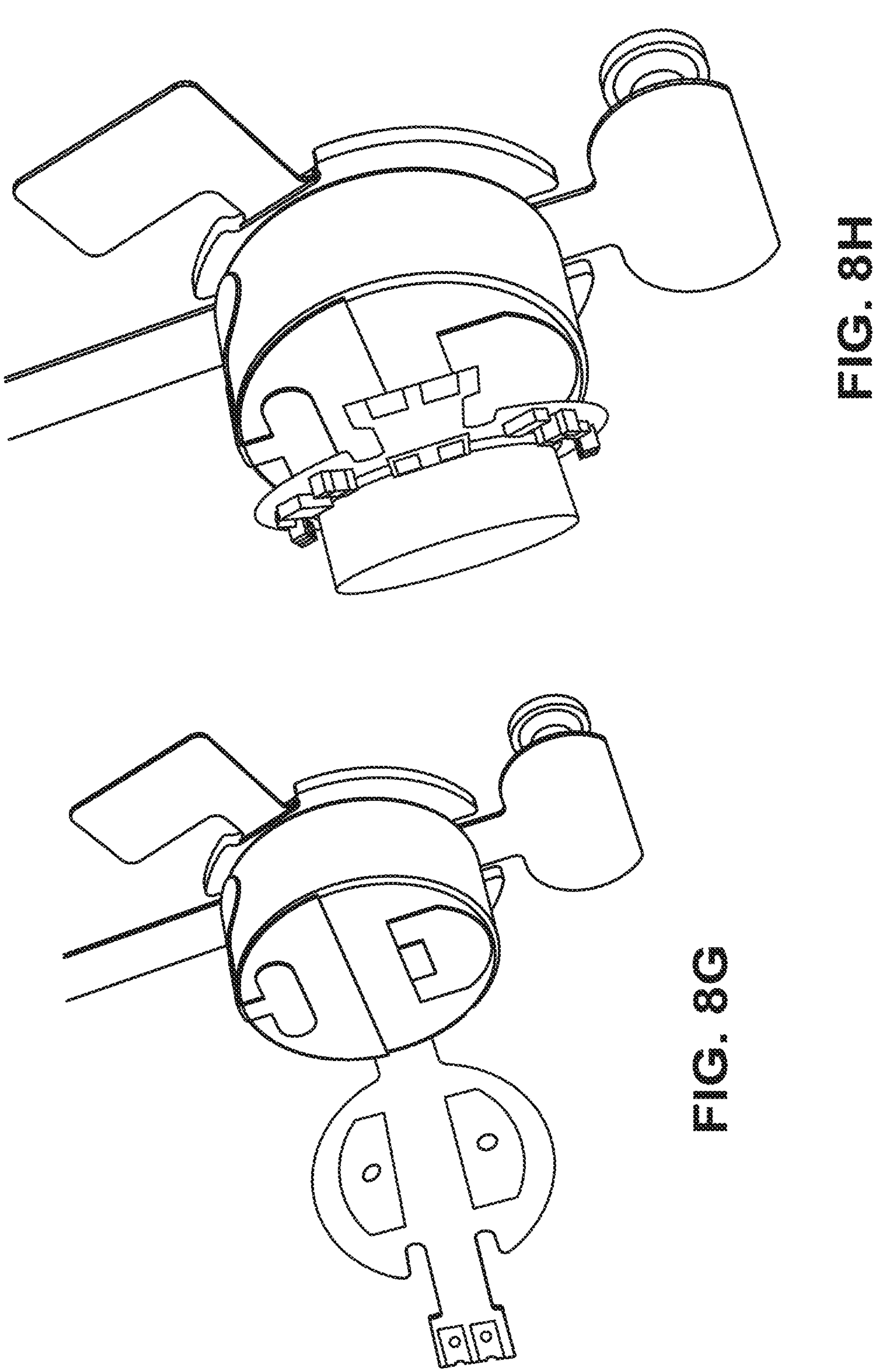
Figures 8I, 8J:
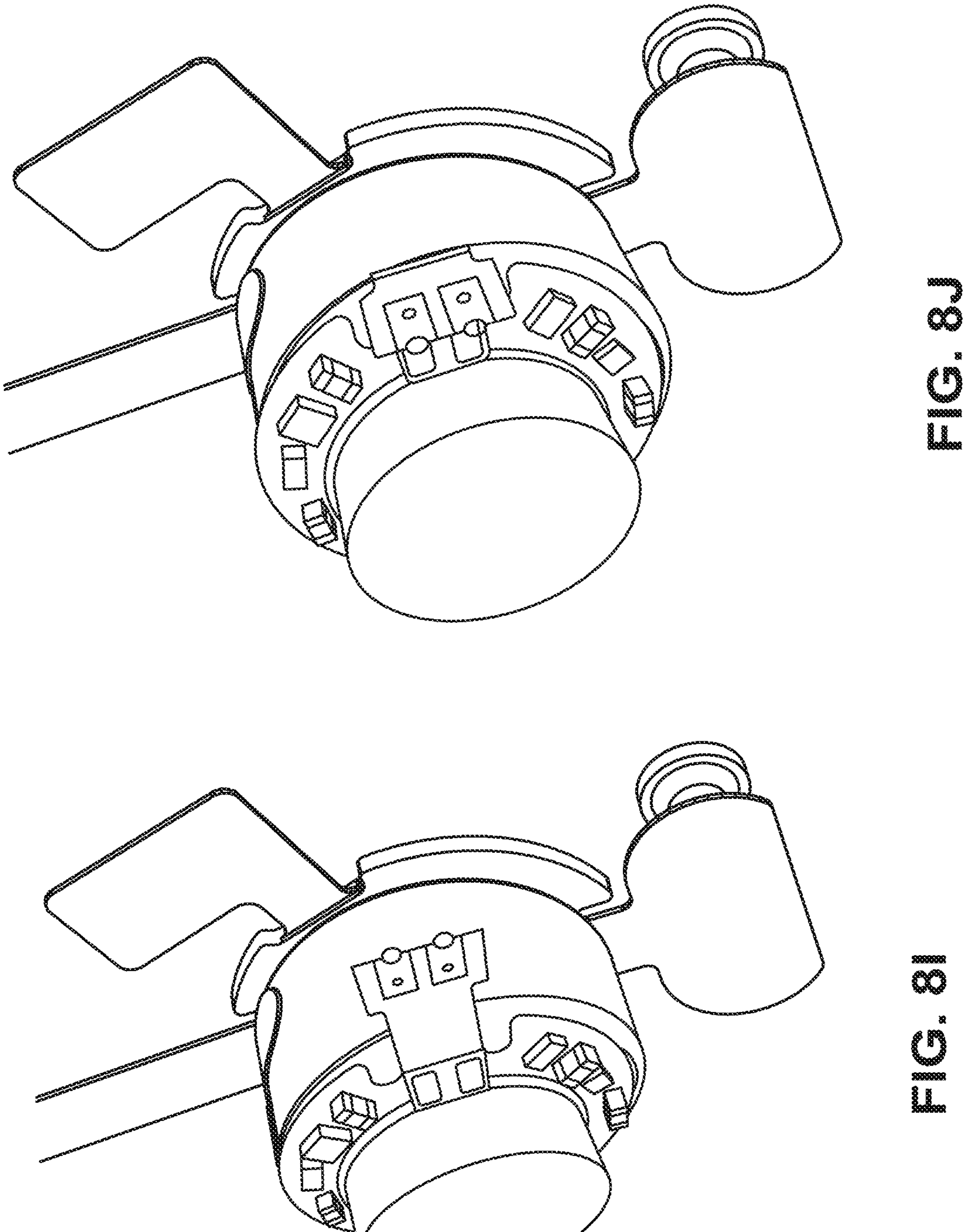
Figure 8L:
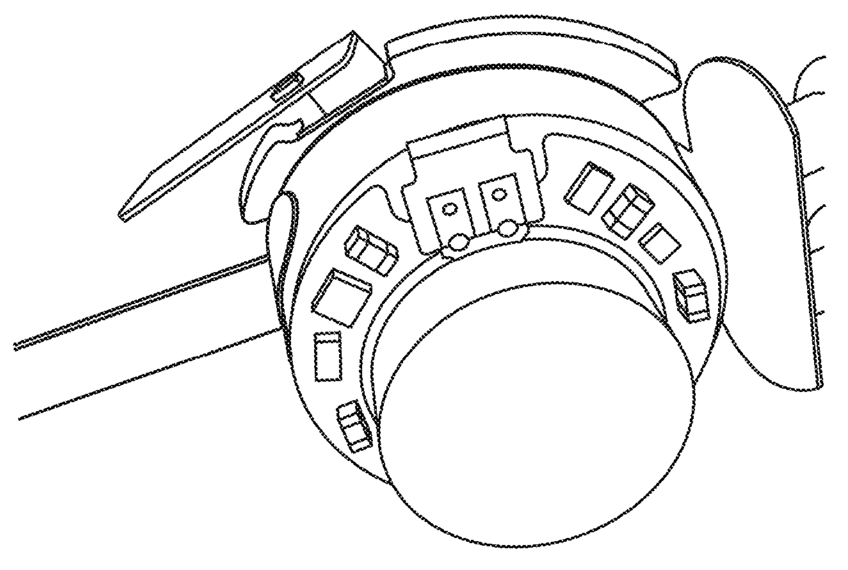
Figure 8K:
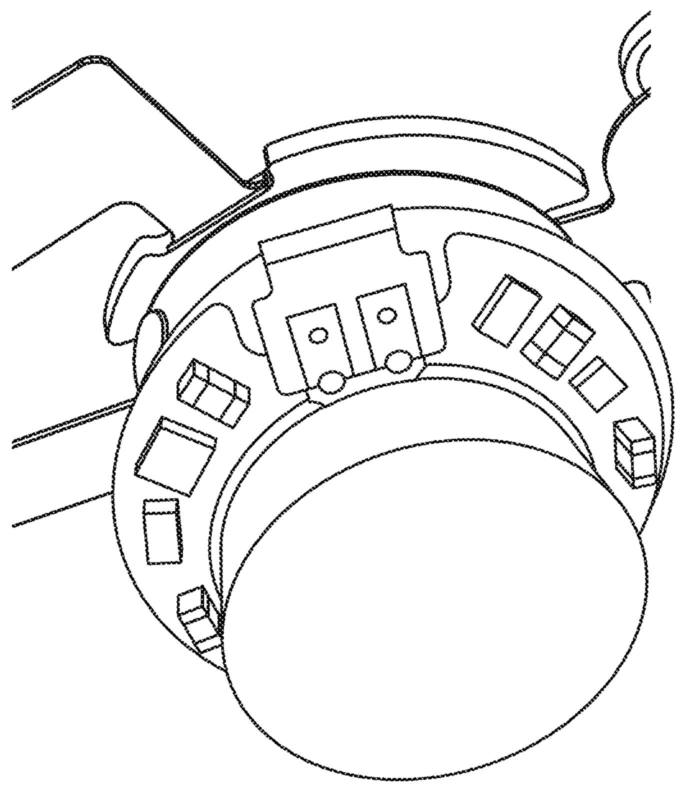
Figures 8M, 8N:
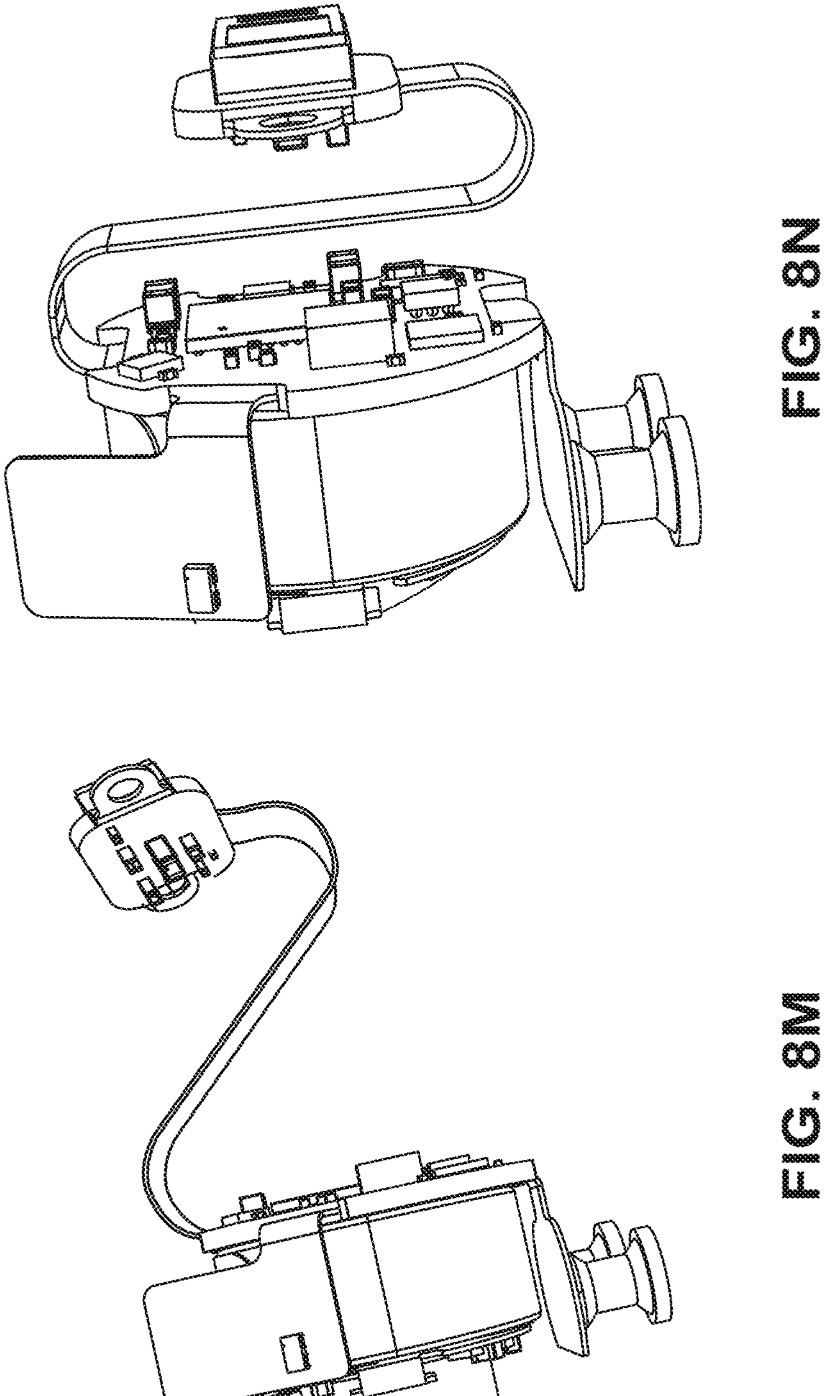
Figures 8O, 8P:
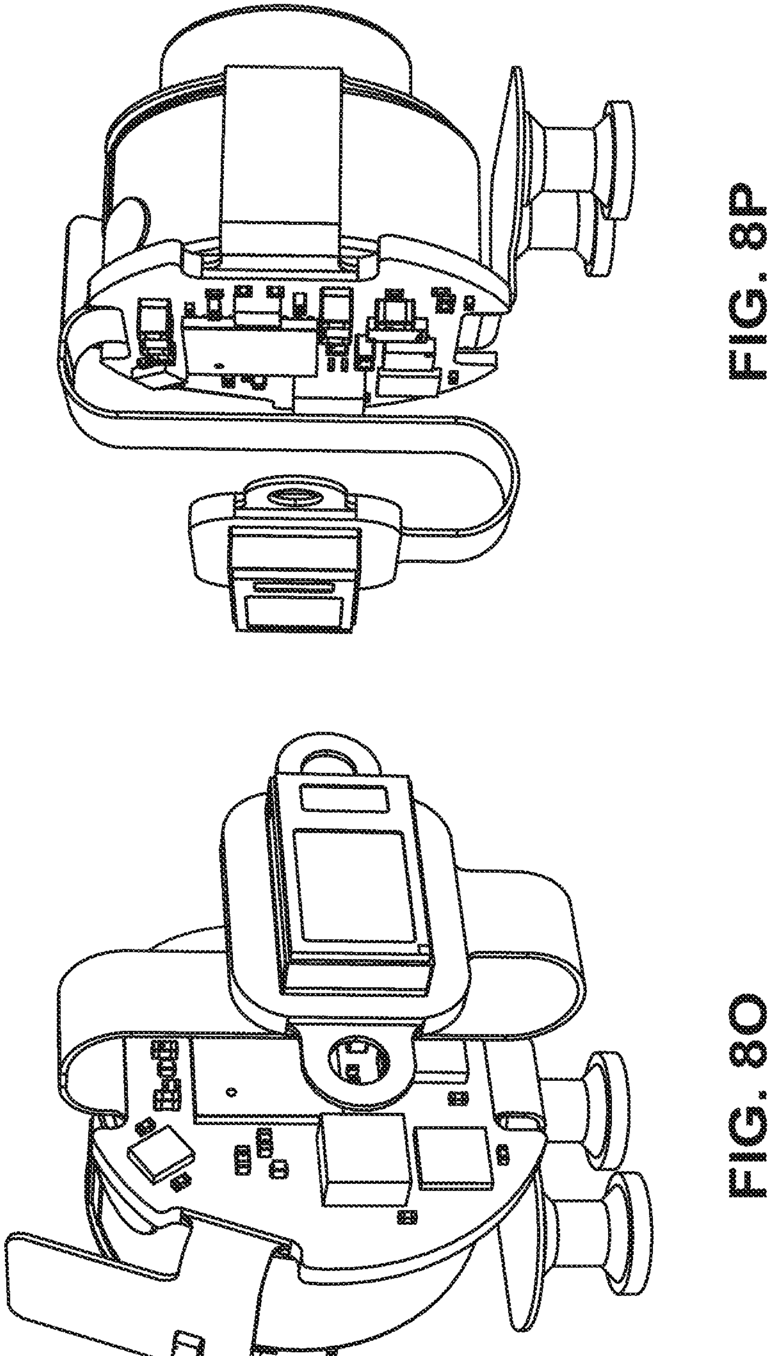
Figure 8R:
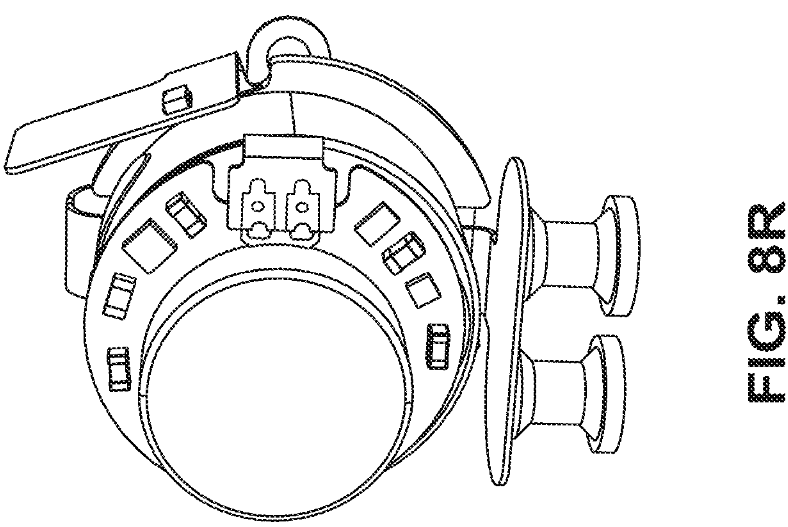
Figure 8Q:
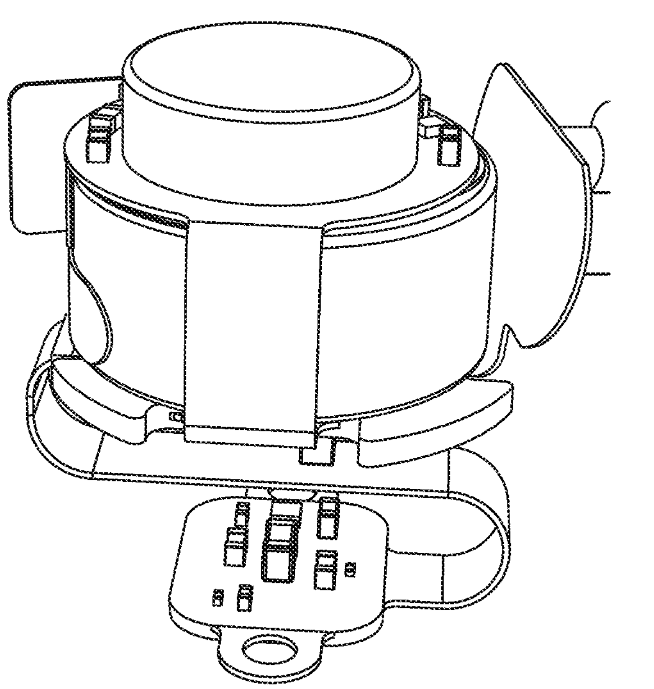
Figure 8T:
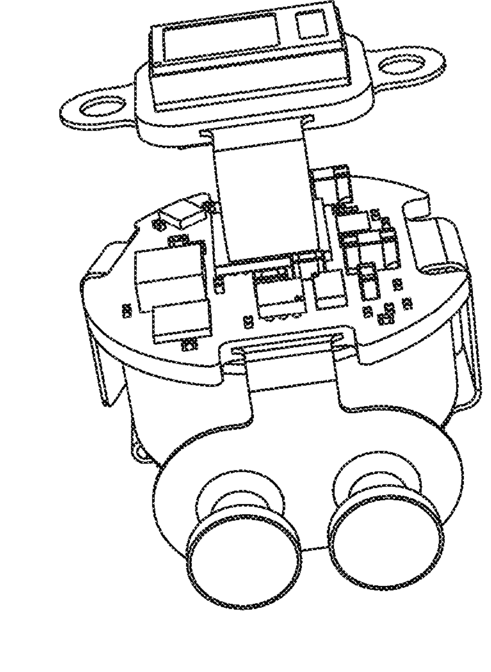
Figure 8S:
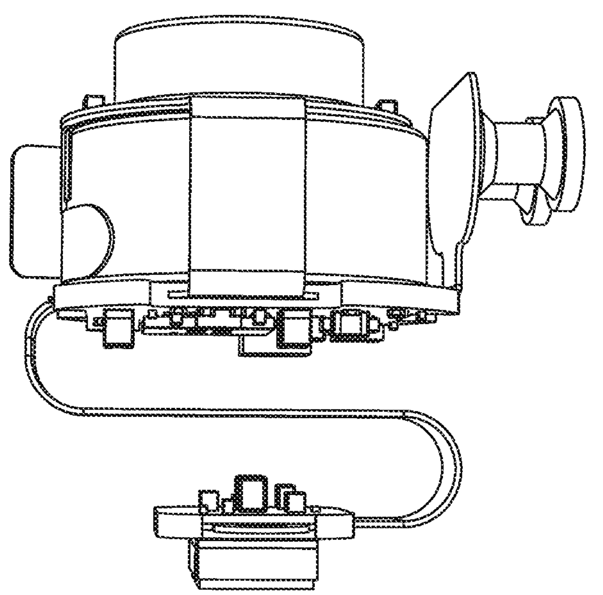
Figure 8U:
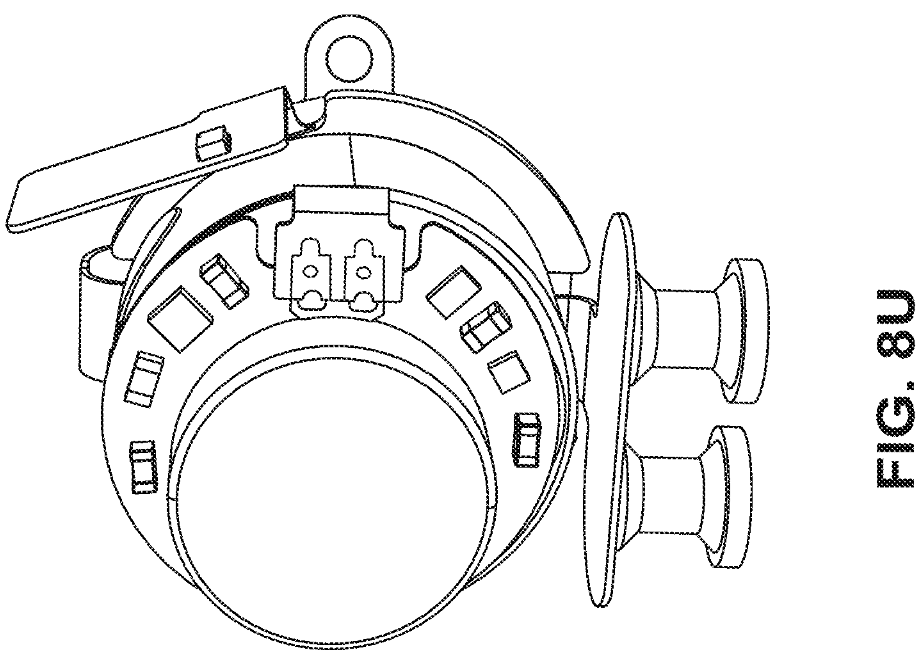
Figure 9B:
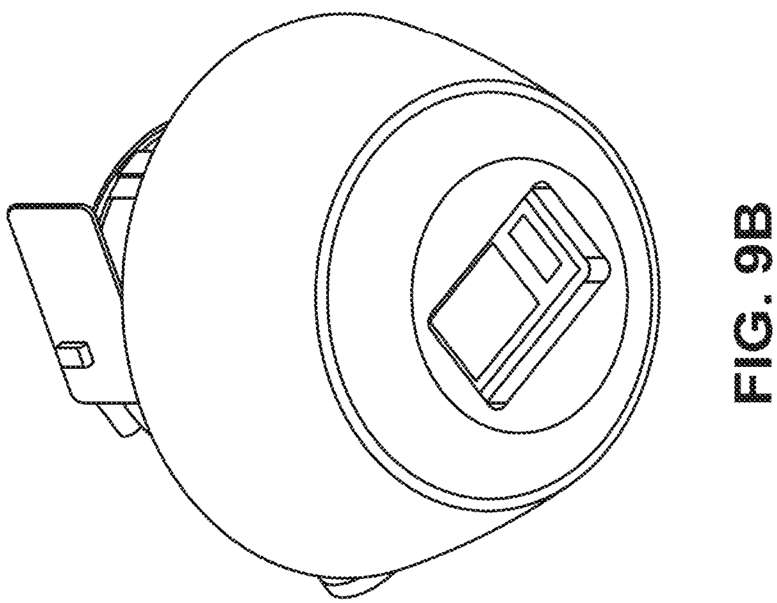
FIGS. 9A-9B are renderings of an earpad with optical sensor circuitry positioned within a recess of the earpad, according to some embodiments.
Figure 9A:
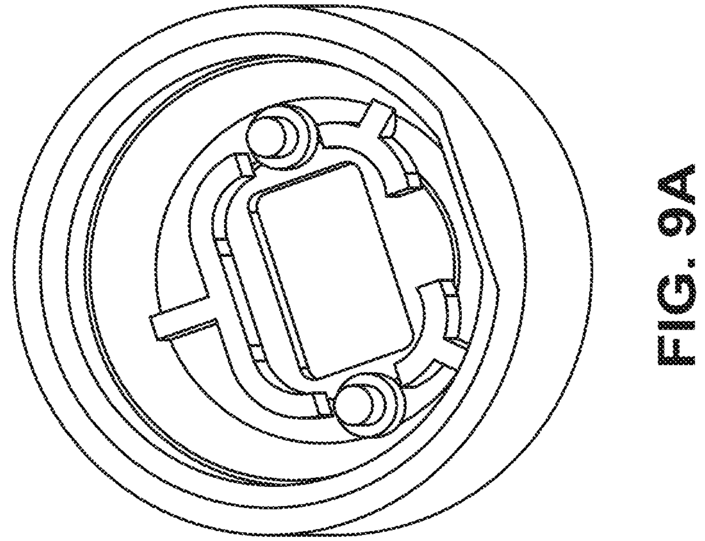
Figure 9C:
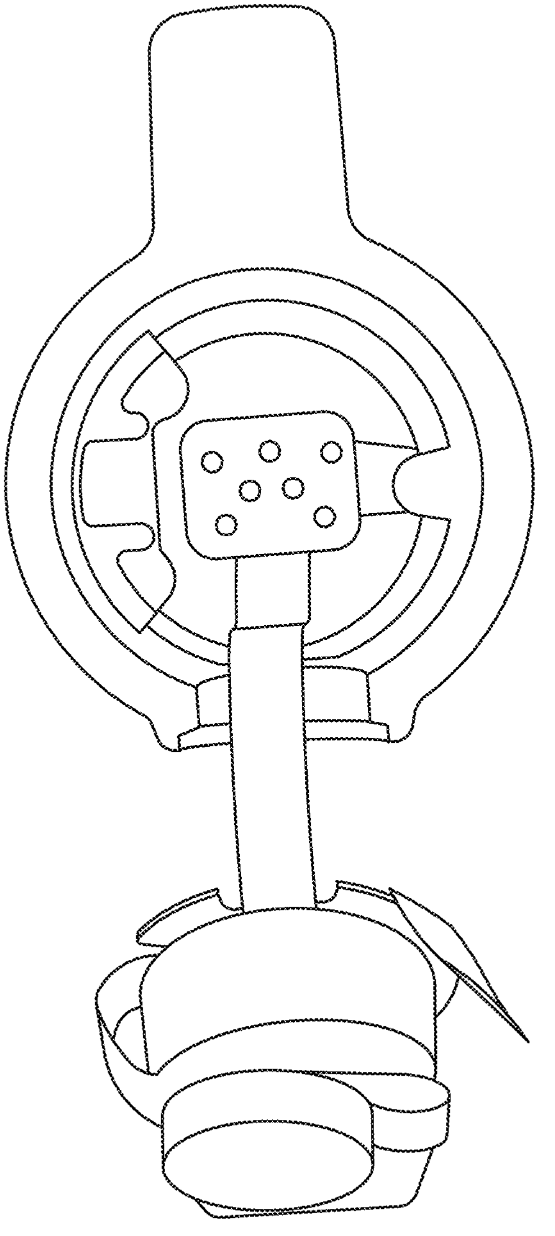
FIG. 9C is a photographic image showing an underside view of an assembled earpad with optical sensor circuitry, according to an embodiment.
Figures 10A, 10B, 10C:
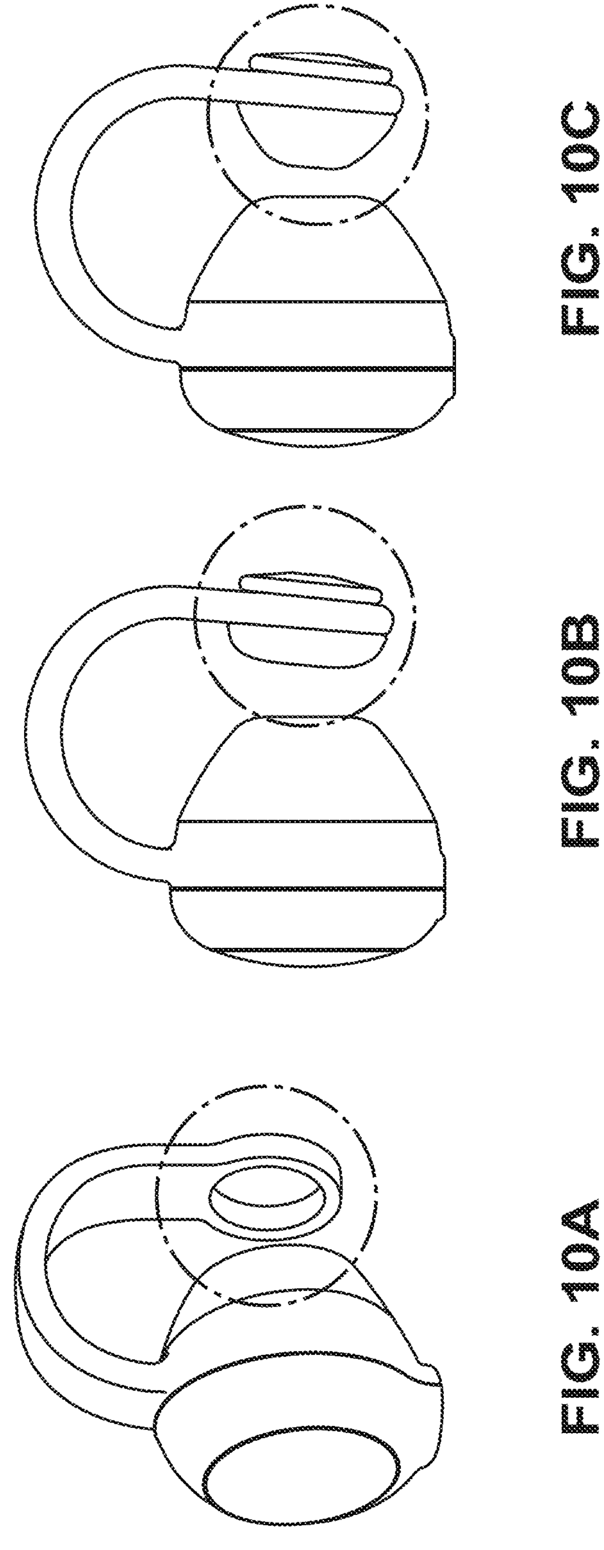
FIGS. 10A-10C are drawings of a wearable oxygen monitor, showing a grommet without an earpad, with a thin earpad, and with a thick earpad, respectively, according to some embodiments.

FIGS. 8A-8U are renderings of a flexible electronics assembly (e.g., electronics 760 of FIG. 7A-7C) for a wearable oxygen monitor, according to some embodiments. FIGS. 9A-9B are renderings of an earpad (e.g., an earpad of a first body portion) with optical sensor circuitry positioned within a recess of the earpad, according to some embodiments. FIG. 9C is a photographic image showing an underside view of an assembled earpad with optical sensor circuitry, according to an embodiment. FIGS. 10A-10C are drawings of a wearable oxygen monitor, showing a grommet without an earpad, with a thin earpad, and with a thick earpad, respectively, according to some embodiments.

Figure 11:
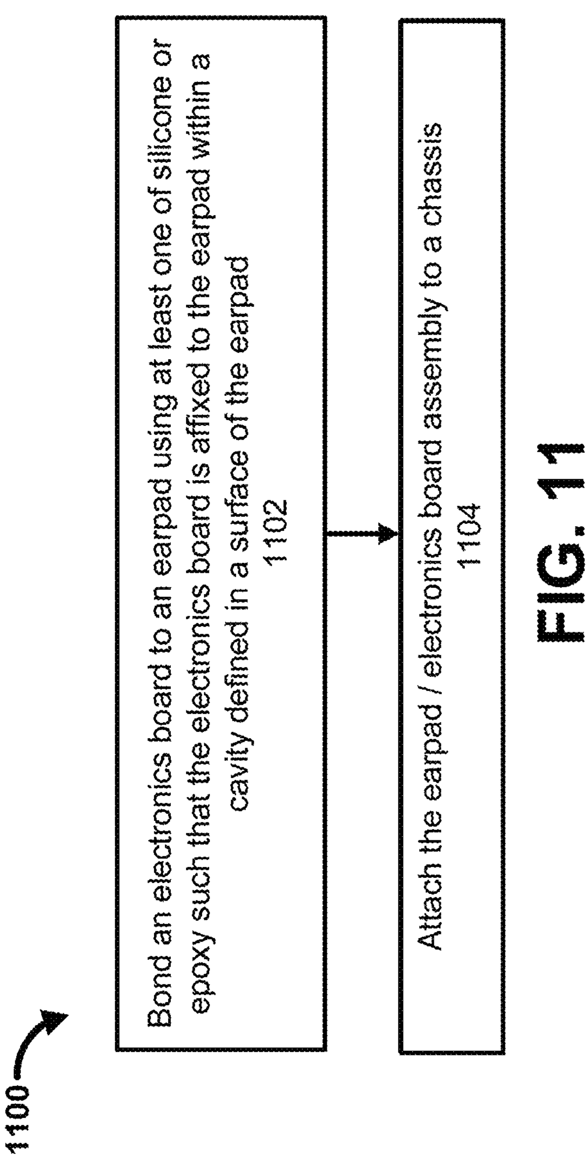
FIG. 11 is a flow diagram showing a method of manufacturing a wearable oxygen monitor, according to some embodiments.

FIG. 11 is a flow diagram showing a method of manufacturing a wearable oxygen monitor, according to some embodiments. As shown in FIG. 11, the method 1100 includes at 1102 bonding an electronics board to an earpad (e.g., flexible earpad 724 of FIG. 7C) using at least one of silicone or epoxy such that the electronics board is affixed to the earpad within a cavity defined in a surface of the earpad, and at 1104 attaching the earpad to a chassis.

In some embodiments, an apparatus for monitoring an oxygen saturation level of a wearer of the apparatus includes a first body portion, a second body portion, and a connection member. The first body portion includes a processor, a memory operably coupled to the processor, at least one light-emitting diode, and at least one optical sensor configured to detect, during operation, a reflected portion of light emitted from the at least one light-emitting diode. The second body portion includes a grommet, and the connection member is mechanically coupled to each of the first body portion and the second body portion. The memory stores instructions to cause the processor to cause light to be emitted from the at least one light-emitting diode when the apparatus is positioned on an ear of a wearer and during operation of the apparatus, and to calculate a blood oxygen saturation level of the wearer based on the reflected portion of light.

In some implementations, the second body portion further includes a flexible earpad. Alternatively or in addition, the first body portion can include a flexible earpad. Alternatively or in addition, the apparatus further comprises a vibration motor, the memory further storing instructions to operate the vibration motor in response to detecting an event. The event can include at least one of: detecting an alarm condition, detecting a low battery condition, or detecting a successful positioning of the apparatus on the ear of the wearer.

In some embodiments, the connection member can include nylon. Alternatively or in addition, the first body portion can include a flexible earpad, and the at least one optical sensor can be positioned (e.g., potted) within a cavity defined in the flexible earpad. For example, the at least one optical sensor can be secured within the cavity by an epoxy.

The processor and the memory can be positioned on a circuit board, and the at least one optical sensor can be electrically coupled to the circuit board via a flexible conductor. The flexible conductor can be substantially S-shaped.

In some embodiments, the apparatus also includes at least one of a microphone or a speaker operatively coupled to the processor, and the memory further stores instructions to cause the processor to activate the at least one of the microphone or the speaker in response to detecting an alarm condition.

In some embodiments, the apparatus also includes a wireless transceiver, operatively coupled to the processor and configured to communicate with a mobile software application, the memory further storing instructions to cause the processor to send signals representing measurement data to the mobile software application via the wireless transceiver.

In some embodiments, the memory further stores instructions to cause the processor to send signals, according to a predetermined schedule, to a mobile software application, the signals representing measurement data.

In some embodiments, the apparatus also includes at least one sensor operatively coupled to the processor, the at least one sensor including at least one of: a body temperature sensor, an air quality sensor, a humidity sensor, an altimeter, or a barometric pressure sensor, the memory further storing instructions to cause the processor to store, in the memory, data collected by the at least one sensor.

In some embodiments, the apparatus also includes at least one sensor operatively coupled to the processor, the at least one sensor including at least one of: a body temperature sensor, an air quality sensor, a humidity sensor, an altimeter, or a barometric pressure sensor, the memory further storing instructions to cause the processor to send signals, according to a predetermined schedule, to a mobile software application, the signals representing data collected by the at least one sensor.

In some embodiments, the reflected portion of light is a first reflected portion of light and the instructions to cause the processor to calculate the blood oxygen saturation level of the wearer include instructions to cause the processor to calculate the blood oxygen saturation level of the wearer based on the first reflected portion of light and a second reflected portion of light.

In some embodiments, the apparatus also includes an alert mechanism (e.g., a button) operatively coupled to the processor, the memory further storing instructions to cause the processor to generate and send a signal representing an alert in response to detecting a user interaction with the alert mechanism. In some embodiments, the apparatus is waterproof. In some embodiments, the second body portion does not include any electronic components.

In some embodiments, a kit includes an ear-wearable apparatus, a charger case, and a plurality of flexible earpads. The ear-wearable apparatus is configured to be positioned on an ear of a wearer, and the apparatus includes a first body portion, a second body portion, and a connection member mechanically coupled to each of the first body portion and the second body portion. The first body portion has a processor, a memory operably coupled to the processor, at least one light-emitting diode, and at least one optical sensor configured to detect, during operation, a reflected portion of light emitted from the at least one light-emitting diode, the reflected portion of light being reflected from a surface of the ear of the wearer. The memory stores instructions to cause the processor to calculate a blood oxygen saturation level of the wearer based on the reflected portion of light. The charger case is configured to contain and supply power to the apparatus. The plurality of flexible earpads, each flexible earpad from the plurality of flexible earpads configured to be mechanically coupled to the second body portion. The second body portion can include an annular opening, and each flexible earpad from the plurality of flexible earpads can be configured to be mechanically coupled to the second body portion via the annular opening. Alternatively or in addition, the apparatus and the charger case can be configured such that data can be exchanged between the apparatus and the charger case (e.g., via a pair of electrical contacts).

Wearable oxygen monitors of the present disclosure, according to some embodiments, can include one or more (e.g., any combination) of the following capabilities:

Continuous oxygen monitoring;
Heart rate monitoring;
Generating and sending alerts;
Activation of a pre-defined emergency plan;
Interaction with a mobile software application; and/or
Predictive analytics.

In some embodiments, a wearable monitoring system includes a wearable oxygen monitor and a mobile software application ("mobile app") running on a compute device of a user or wearer of the wearable oxygen monitor. During operation of the wearable oxygen monitor (i.e., when the wearable oxygen monitor is powered on and being worn by the wearer), the wearable oxygen monitor can continuously monitor the oxygen level of the wearer, for example by comparing a measured oxygen level to a pre-defined oxygen level threshold. Based on the monitoring, and in response to detecting that a measured oxygen level is less than the pre-defined oxygen level threshold, the wearable oxygen monitor can generate an alert, the alert including a representation of the low oxygen condition, and send a signal representing the alert to the mobile app to cause an alert (including one or more of text, graphics, video indications, and audio indications) to be displayed and/or played by the mobile app and the compute device (e.g., via a graphical user interface (GUI) of the compute device and/or one or more speakers thereof).

In some embodiments, during operation, the wearable oxygen monitor detects data associated with one or more physiological conditions of the wearer (collectively referred to herein as "vital signs"), including, but not limited to, oxygen level, heart rate, etc., for example at multiple instances over time. The wearable oxygen monitor can, in response to detecting the vital signs, store the vital signs in a memory of the wearable oxygen monitor. Alternatively or in combination, the wearable oxygen monitor can send a signal representing the vital signs to one or more remote compute devices (e.g., a mobile compute device of a user or the wearer, optionally running the mobile app) for storage and/or display (e.g., via a GUI). The vital signs can subsequently be accessible and retrievable by the wearer or user. In addition, the wearer can provide access to the vital signs to a medical practitioner, for example by providing the medical practitioner with access credentials (for the wearable oxygen monitor and/or the mobile app) and/or by generating and sending (via the mobile app) an email or other message, including a representation of the vital signs, to the medical practitioner.

In some embodiments, a wearable monitoring system includes a wearable oxygen monitor and a mobile app running on a compute device of a user or wearer of the wearable oxygen monitor. The wearable monitoring system is configured to generate and send one or more alerts when a vital sign is determined not to comply with a predetermined condition (optionally customizable by the wearer/user). For example, the wearable monitoring system (e.g., the wearable oxygen monitor and/or the mobile app) can be configured to generate and send one or more alerts when an oxygen level, measured by the wearable oxygen monitor, drops below a pre-defined (optionally customizable) level (also referred to herein as a "trigger" or "threshold value"). In addition, the wearable monitoring system can be configured to generate and send one or more alerts in response to when the user/wearer presses an alert mechanism (e.g., an actuatable button) on the wearable oxygen monitor, or otherwise interacts with the wearable oxygen monitor (examples of which include, but are not limited to, voice command, rotation of a component of the wearable oxygen monitor, sliding of a component of the wearable oxygen monitor, pressing or squeezing a component of the wearable oxygen monitor (e.g., for a predefined duration, with a predefined amount of force, a predetermined number of times in succession (e.g., 3 times), in a predefined pattern, etc.), removal of a component of the wearable oxygen monitor, removal of the entirety of the wearable oxygen monitor from the ear of the wearer, etc.).

The one or more alerts can include a representation of a "low oxygen" condition and/or an associated instruction to execute one or more commands, such as initiating a telephone call (e.g., via the mobile device running the mobile app) to, or otherwise contacting, emergency services (e.g., 911), sending an SMS, email or other message to one or more emergency contacts, emitting a sound from a sound emitter of the wearable oxygen monitor (e.g., an electronic beep sound effect emitted via a speaker), causing a vibration to be generated by a haptic feedback element of the wearable oxygen monitor (e.g., a piezoelectric transducer), transmitting (e.g., via a transceiver onboard the wearable oxygen monitor) a signal to a mobile device to cause an alert such as a sound effect and/or a vibration, etc. The user or wearer can, via the mobile app, define customized values for one or more of the following: threshold oxygen level(s), detection intervals (e.g., for oxygen levels, blood oxygen saturation levels, or other vital signs), frequency of calculation of vital signs (e.g., to calculate oxygen concentration at 1-30 second time intervals), threshold values for other vital signs and/or biometrics, emergency contact information (e.g., phone numbers, email addresses, names, etc.), emergency plan data, priority order of vital signs, priority order of emergency contacts, access permissions for healthcare providers, etc.

In some embodiments, the wearable monitoring system includes a predictive analytics capability and/or interacts with a predictive analytics system, to provide advance warnings ("pre-warnings") to the wearer or user before an acute health episode occurs, for example by identifying/detecting patterns based on previous acute health episodes of the wearer/user. The predictive analytics capability can be implemented using software (e.g., artificial intelligence (AI), machine learning, or other algorithms) and/or hardware. The identifying/detecting the patterns can be performed by analyzing biometric data (including vital signs and/or other data detected and/or gathered by the wearable monitoring system), optionally in combination with geometric data and/or barometric data collected using the wearable monitoring system. For example, collected geometric data and/or barometric data can be compared with historical data pertaining to occurrences of low oxygen alerts/warnings and/or invocations of emergency services (e.g., 911 calls) to identify one or more patterns or correlations that can be used to predict a next alert for a wearer, to predict sets of conditions under which a wearer is likely to experience an alert event, to generate one or more advance warnings for display via a GUI of the wearer's mobile compute device, etc.

In some embodiments, a wearable monitoring system includes a wearable, hardware-based earpiece, and a mobile app that is compatible with Windows®, iOS®, and Android® compute devices. The earpiece is configured to communicate with a compute device running the mobile app, for example using a power-efficient, lightweight wireless protocol, such as Bluetooth®, BLE®, ZigBee®, Z-Wave®, 6LoWPAN®, Thread®, WiFi-ah® (HaLow®), 2G® (GSM), 3G®, 4G®, LTE® Cat 0®, Cat 1®, Cat 3®, LTE-MI®, Narrowband IoT® (NB-IoT®), 5G®, NFC®, RFID, SigFox®, LoRaWAN®, Ingenu®, Weightless-N®, Weightless-PR, Weightless-W®, ANT®, ANT+®, DigiMesh®, MiWi®, EnOccan®, Dash7®, or WirelessHART®. The earpiece includes one or more of the following components: one or more light-emitting diodes (LEDs), one or more photosensors/photodetectors, one or more lightweight power-efficient wireless sensors, a speaker, a microphone, one or more air quality monitoring sensors, and one or more body temperature sensors. During operation of the earpiece, the one or more LEDs can transmit light, generated by the one or more LEDS, through a portion of an ear of a wearer of the earpiece, such that the transmitted light is detected by the one or more photosensors/photodetectors, the one or more photosensors/photodetectors disposed on an opposite side of the portion of the ear, as compared with the one or more LEDs. An amount of the light that is absorbed by the ear can be determined/calculated based on the amount of transmitted light detected by the one or more photosensors/photodetectors. A blood oxygen saturation (SpO2) level can then be calculated, based on the amount of light absorbed by the ear, for example using the Beer-Lambert Law ("Beer's Law"). The calculation of the amount of the light absorbed by the ear and/or the calculation of the SpO2 level can be performed by a processor of the earpiece, the mobile app, and/or via a processor of a remote compute device in communication with the earpiece.

In some embodiments, a wearable monitoring system includes a wearable, hardware-based earpiece (wearable oxygen monitor), a charger (e.g., a charging "pod," as shown in FIGS. 1F-1J), and a mobile app. The wearable oxygen monitor can be in continuous communication via the mobile app, e.g., using one or more wireless antennas or sensors. The charger can be a wireless charger, configured to wirelessly charge the earpiece when the earpiece is at least partially physically received within the charger (and, optionally, when a cover or lid of the charger is closed). The earpiece can be configured to generate and/or send an alarm in response to detecting that an oxygen level of a wearer is lower than a pre-defined threshold value. In addition, the earpiece can be configured to generate and/or send multiple alarms, in response to multiple detections, over time, of an oxygen level of the wearer being lower than the pre-defined threshold value. A frequency of generating and/or sending the alarms can increase in response to detecting that differences between measured/detected/calculated oxygen levels of the wearer and the pre-defined threshold value are getting larger over time (i.e., the measured/detected/calculated oxygen levels of the wearer are decreasing over time, and are all lower than the pre-defined threshold value). Similarly, a frequency of generating and/or sending the alarms can decrease in response to detecting that differences between measured/detected/calculated oxygen levels of the wearer and the pre-defined threshold value are getting smaller over time (i.e., the measured/detected/calculated oxygen levels of the wearer are increasing over time, and are all lower than the pre-defined value). In addition, an intensity or severity of the alarms can increase over time, and/or a type of alarm generated/sent can change over time, in response to detecting that differences between measured/detected/calculated oxygen levels of the wearer and the pre-defined threshold value are getting larger over time. For example, an emitted sound (from the wearable oxygen monitor and/or from the compute device running the mobile app) can get louder, a rate of a flashing light (on the wearable oxygen monitor and/or of the compute device running the mobile app) can increase, a text description of the alarms (e.g., presented to a wearer/user via a GUI of the mobile device running the mobile app) can change from "low" to "moderate," or from "moderate" to high," etc. Similarly, an intensity of the alarms can decrease over time, and/or a type of alarm generated/sent can change over time, in response to detecting that differences between measured/detected/calculated oxygen levels of the wearer and the pre-defined threshold value are getting smaller over time. For example, an emitted sound (from the wearable oxygen monitor and/or from the compute device running the mobile app) can get quieter/softer, a rate of a flashing light (on the wearable oxygen monitor and/or of the compute device running the mobile app) can decrease, a text description of the alarms (e.g., presented to a wearer/user via a GUI of the mobile device running the mobile app) can change from "high" to "moderate," or from "moderate" to low," etc. The alarms can terminate when a most recently measured/detected/calculated oxygen level of the wearer reaches a "normal" level (e.g., at or above the pre-defined threshold value).

Embodiments set forth herein can be used to monitor symptoms of, predict the progression of, and/or as part of a treatment plan for one or more conditions such as pulmonary hypertension (PH), pulmonary arterial hypertension (PAH), idiopathic PAH (IPAH), pulmonary fibrosis, sceloderma, cystic fibrosis, lupus, sickle cell anemia, asthma, chronic obstructive pulmonary disease (COPD), heart disease, and Eisenmenger's Syndrome.

In some embodiments, a wearable oxygen monitor is configured to continuously or intermittently monitor vital signs such as oxygen levels and heart rates, and send data associated with the vital signs (e.g., via the mobile app) for storage in records of a memory or other storage repository, via a mobile app (e.g., implemented using a cloud-based server). In some such instances, when storing the vital signs, the mobile app can also cause the storage of some or all of the following additional information: GPS location of the wearer, altitude of the wearer (e.g., retrieved using a Google application programming interface (API)), an indication of room air quality (e.g., detected by an onboard sensor of the wearable oxygen monitor), environmental temperature, and environmental humidity level.

A wearer or user of the wearable oxygen monitor can subsequently retrieve/download the records (e.g., based on a specified date or date range), for example to show their physician for purposes of diagnosis and/or investigation of causes behind undesirable fluctuations. Alternatively or in addition, the records can automatically be downloaded, for example according to a pre-defined, customizable schedule (e.g., daily, weekly, monthly), and emailed to the wearer and/or other users, medical providers, etc.

In some embodiments, a wearable oxygen monitor is configured to initiate a telephone call to emergency services (e.g., 911) in response to a wearer or user pressing an alert mechanism (e.g., an actuatable button of), or otherwise interacting with an interface of, the wearable oxygen monitor. The button press (or other interaction) can also trigger the activation of an onboard speaker and microphone, to facilitate the telephone call, such that the wearer or user can speak into the microphone and hear the other party on the telephone call via the speaker. This allows the wearer/user to communicate the situation to emergency services and request appropriate help. Optionally, the button press (or other interaction) can also trigger (e.g., concurrently) the generation and wireless sending of an alert via SMS text message to one or more user-defined emergency contact phone numbers (e.g., as defined in the mobile app).

Alternatively or in addition, in some embodiments, a wearable oxygen monitor is configured to generate and send SMS text messages to one or multiple (e.g., 3) emergency contacts pre-defined by a wearer (e.g., as part of a pre-defined emergency plan), in response to the wearer or a user (e.g., a bystander) pressing a button of (or otherwise interacting with an interface of) the wearable oxygen monitor. The SMS text messages can include one or more of the following: an alert message, vital sign data of the wearer, a current GPS location of the wearer, and an indication as to whether emergency services (e.g., 911) have already been called.

In some embodiments, during operation, a wearable oxygen monitor is positioned on a portion of an ear of a wearer, and is in continuous communication (e.g., via one or more wireless antennas, such as Bluetooth®, 4G®, or 5G® antennas) with a mobile app that is concurrently running on a mobile compute device of the wearer. The wearable oxygen monitor. continuously or intermittently over time, detects oxygen levels and heart rates of the wearer, and sends signals to cause display of the detected oxygen levels and heart rates of the wearer via a GUI of the mobile compute device of the wearer. The display of the detected oxygen levels and heart rates can be, for example, in the form of a graph, plot, or chart. The display can be dynamically updated, in real time or substantially in real time, in response to new measurements of oxygen levels and heart rates. As used herein, "substantially in real-time" can refer to an event that occurs immediately following a predicate event, adjusted for processing-related delays (e.g., computation delay, transmission delay, etc.). When triggered, an alert can be displayed within the GUI, together with or instead of the displayed data.

In some embodiments, the wearable oxygen monitor is an internet-of-things (IoT) device and includes an onboard Long-Term Evolution (LTE) module/chip, for 5G connectivity to other compute devices within the IoT.

In some embodiments, a first housing portion of a wearable oxygen monitor includes one or more air quality sensors, a speaker, an alert mechanism (e.g., an actuatable button), and a microphone. In some such embodiments, two or more of the microphone, the speaker and the one or more air quality sensors "share" (i.e., are open to external air via) a common opening in an outer shell/wall of the first housing portion, while a remainder of the outer shell/wall of the first housing portion, as well as an entirety of an outer shell/wall of the second housing portion are sealed and waterproof. The one or more air quality sensors can be configured to detect one or more of: biogenic volatile compounds (BVOC), temperature, humidity, carbon monoxide, carbon dioxide, sulfur dioxide, nitrous oxide, particulate matter, ozone and/or other gases. For example, in some embodiments, the one or more air quality sensors are configured to detect temperature, humidity, and one or more BVOCs, and to output a relative "score" of ambient air quality. Alternatively or in addition, the first housing portion can include a Bluetooth® 5.1 Direction Finding capability, for example to identify relative locations of multiple users (e.g., patients within a hospital). Batteries described herein can be rechargeable or non-rechargeable. Body temperature sensor(s) described herein can include one or more thermally conductive probes and/or one or more non-contact temperature sensors, such as thermopile infrared (IR) sensors.

In some embodiments, a first housing portion of a wearable oxygen monitor includes analog processing circuitry and/or one or more internal measurement sensors. The one or more internal measurement sensors can include one or more of, for example: an altimeter, gyroscope, accelerometer, GPS sensor, magnetometer, galvanic skin response (GSR) sensor, or a humidity sensor. The processor of the wearable oxygen monitor can be operably coupled to each of the analog processing circuitry and the one or more internal measurement sensors.

Alternatively or in addition, in some embodiments, a memory of a wearable oxygen monitor stores instructions to cause the processor to detect that an alert mechanism of the wearable oxygen monitor has been interacted with (e.g., pressed) by a wearer (i.e., a manual alert), and, in response to detecting that the alert mechanism has been interacted with, generate and send (via the wireless transceiver) a message to one or multiple emergency contacts stored in the memory (e.g., as part of an emergency plan stored therein). The memory can also store instructions to cause the processor, in response to detecting that the alert mechanism has been interacted with, to: initiate a telephone call to emergency services (911), activate a speaker, activate a microphone, emit a sound to indicate an alarm, emit a light to indicate an alarm, generate and send (via the wireless transceiver) an alert message to the mobile app for presentation to a user via a GUI of the user's compute device, and cause storage to memory of an alert record including a date stamp, a time stamp, and measurement data collected from components of the wearable oxygen monitor (e.g., the air quality sensor, photodetectors, the body temperature sensor(s), the internal measurement sensor(s), etc.) at the time of the alert.

Alternatively or in addition, the memory can store instructions to cause the processor to compare a predetermined threshold stored in the memory with one or more measurements collected by one or more components of the wearable oxygen monitor. When the processor determines that the one or more measurements are undesirably below or undesirably above the predetermined threshold, the processor can detect that an alarm condition is present. The memory can also store instructions to cause the processor, in response to detecting the alarm condition, generate and send (via the wireless transceiver) a message to one or multiple emergency contacts stored in the memory (e.g., as part of an emergency plan stored therein). The memory can also store instructions to cause the processor, in response to detecting the alarm condition, to: initiate a telephone call to emergency services (911), activate the speaker, activate the microphone, emit a sound to indicate an alarm, emit a light to indicate an alarm, generate and send (via the wireless transceiver) an alert message to the mobile app for presentation to a user via a GUI of the user's compute device, and cause storage to memory of an alert record including a date stamp, a time stamp, and measurement data collected from components of the wearable oxygen monitor (e.g., the air quality sensor, the photodetectors, the body temperature sensor(s), the internal measurement sensor(s)) at the time of the alert.

In some embodiments, to commence use of a wearable oxygen monitor, a wearer positions the wearable oxygen monitor about a portion of the wearer's ear (e.g., the upper ear, such as the helix, scapha, or pinna of the ear), in a wear configuration. In a first example wear configuration, the first housing portion of the wearable oxygen monitor is in contact with or adjacent to an anterior or front surface of the ear, and the second housing portion of the wearable oxygen monitor is in contact with or adjacent to a posterior or back/rear surface of the ear. In a second example wear configuration, the second housing portion of the wearable oxygen monitor is in contact with or adjacent to an anterior or front surface of the ear, and the first housing portion of the wearable oxygen monitor is in contact with or adjacent to a posterior or back/rear surface of the ear. Stated another way, when the wearable oxygen monitor is worn, the first housing portion and the second housing portion are positioned on opposite sides of the wearer's ear.

In some embodiments, a first light-emitting diode of a wearable oxygen monitor can be configured to emit light having a first wavelength, and a second light-emitting diode of the wearable oxygen monitor can be configured to emit light having a second wavelength different from the first wavelength.

Figure 12:
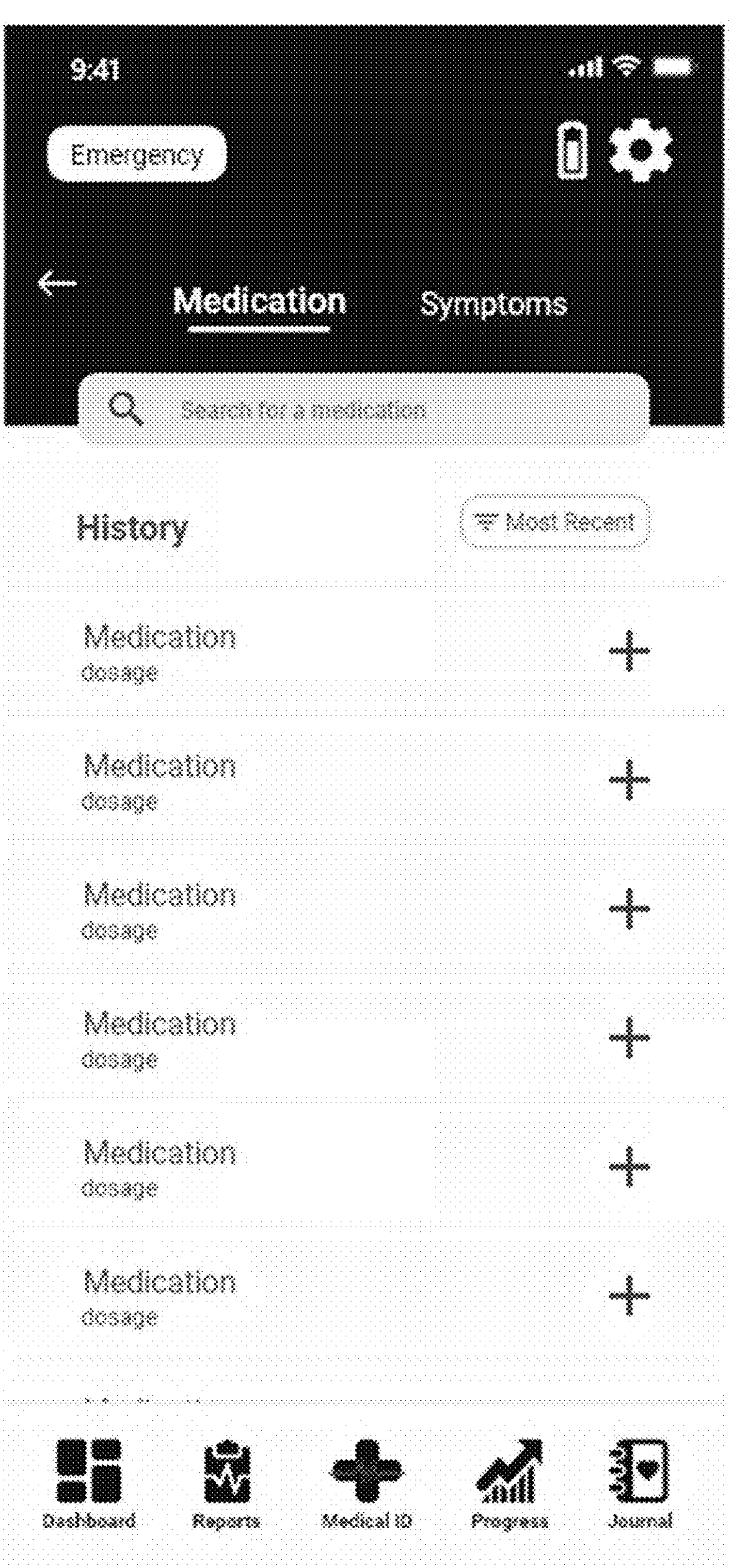

FIGS. 12-48 are wireframes of user interface screens (for GUI display) of a mobile app (e.g., running on a mobile compute device) that interacts with a wearable oxygen monitor (e.g., with any wearable oxygen monitor described herein), according to some embodiments. As shown in FIG. 12, a user of the mobile app (optionally also a wearer of an associated wearable oxygen monitor, as shown and described herein) can create a user profile in the mobile app. The creation of a user profile can include specifying one or more medications that the user is currently taking or has taken in the past. The user interface can include a search bar in which the user can enter search criteria pertaining to one or more medications, and by pressing ENTER, can cause a search to be executed for matches to the search criteria. The results identified via the search can then be displayed for selection via the user interface. The user can "add" medications to their user profile by clicking on the "+" symbol next to the relevant medication(s). Also shown in FIG. 12 are the available/navigable screens: "Dashboard," "Reports," "Medical ID," "Progress" and "Journal."

Figure 13:
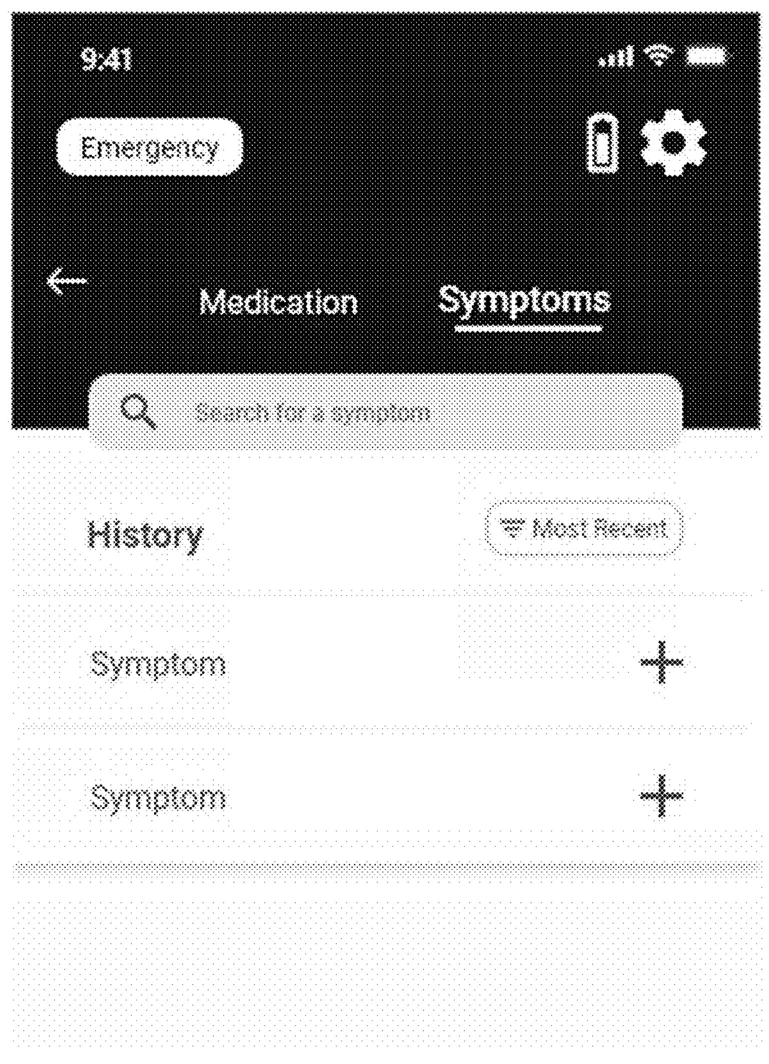
Figure 13:
Figure 14:
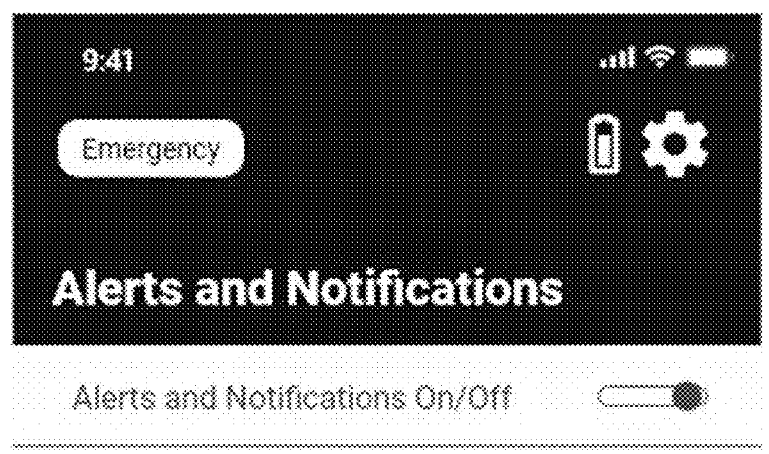
Figure 14:
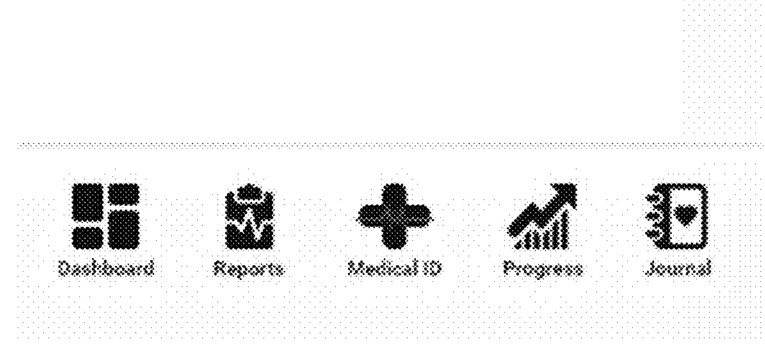
Figure 15:
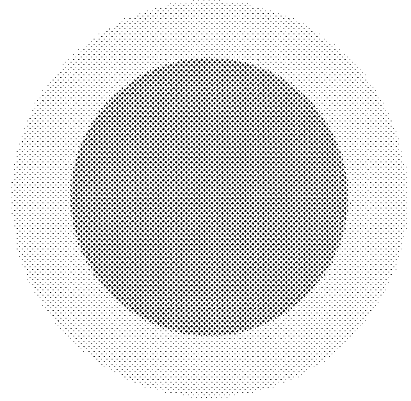
Figure 15:
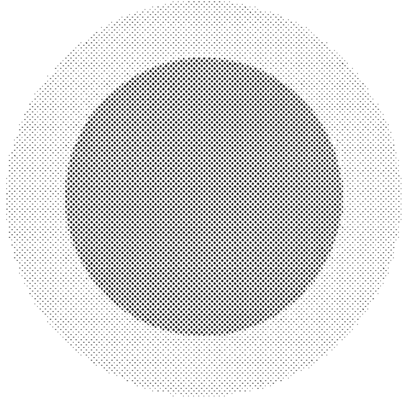
Figure 15:
Figure 17:
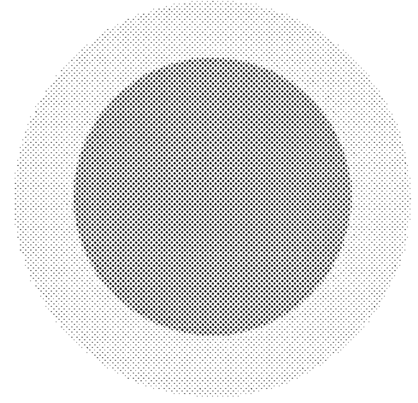
Figure 17:
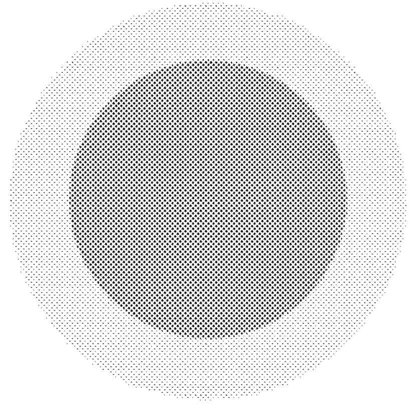
Figure 17:
Figure 18:
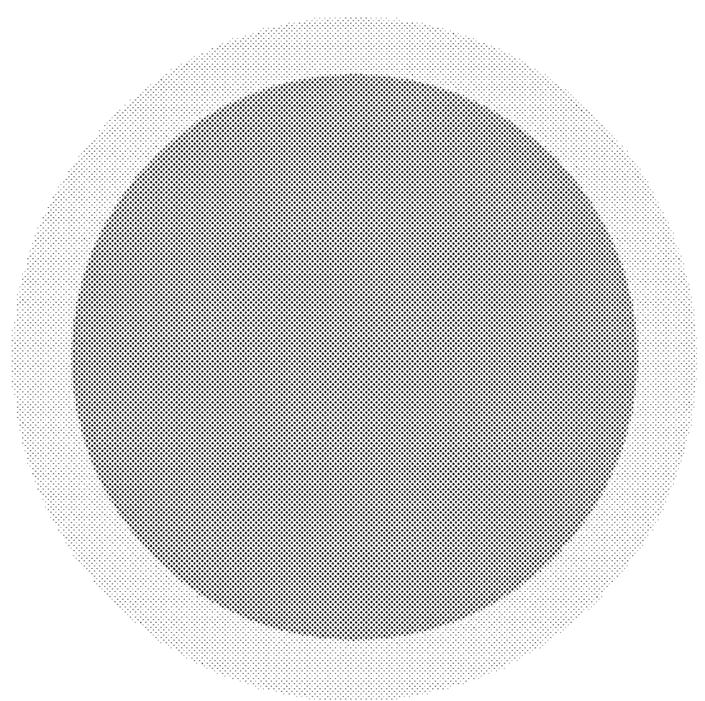
Figure 18:
Figure 19:
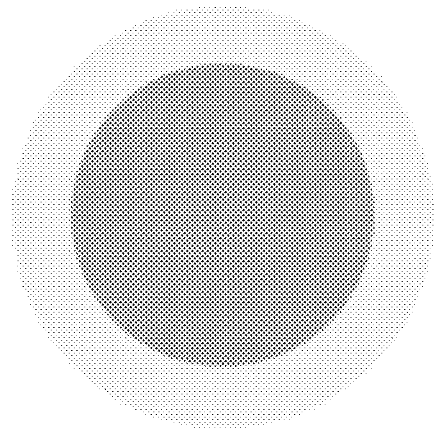

FIG. 13 shows that the creation of a user profile can also include specifying one or more symptoms that the user is currently experiencing or has experienced in the past. The use interface can include a search bar in which the user can enter search criteria pertaining to one or more symptoms, and by pressing ENTER, can cause a search to be executed for matches to the search criteria. The results identified via the search can then be displayed for selection via the user interface. The user can "add" symptoms to their user profile by clicking on the "+" symbol next to the relevant symptom(s). The user interface also includes an "Emergency" button that the user can select to trigger one or more alerts to be generated and/or sent. For example, selecting the "Emergency" button, similar to pressing the alert mechanism of the wearable oxygen monitor described herein, can trigger one or more of the following: generating and sending a message to one or multiple emergency contacts (e.g., stored as part of an emergency plan), initiating a telephone call to emergency services (911), activating speakerphone on the mobile compute device, emitting a sound to indicate an alarm, emitting a light (e.g., of a predetermined color and/or in a predetermined pattern) to indicate an alarm, displaying an alert message via the user interface, and causing storage, in memory, of an alert record including a date stamp, a time stamp, and measurement data collected from components of the wearable oxygen monitor. FIG. 14 shows an Alerts and Notifications user interface, via which the user can turn alerts and notifications on or off, using a slider.

Figure 20:
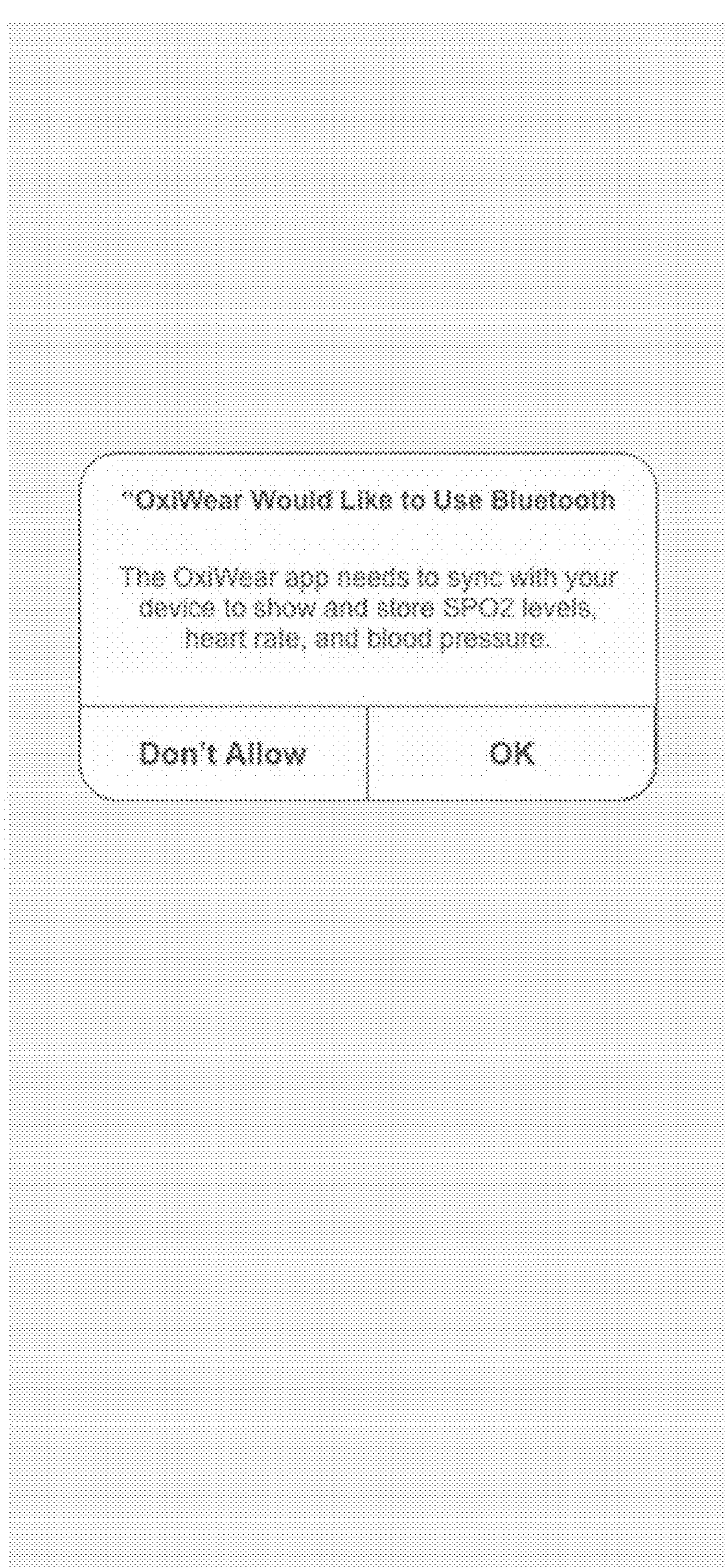
Figure 21:
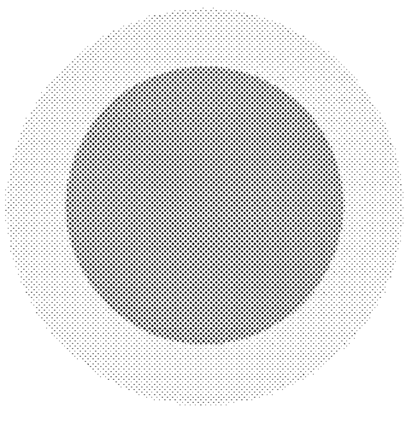
Figure 22:
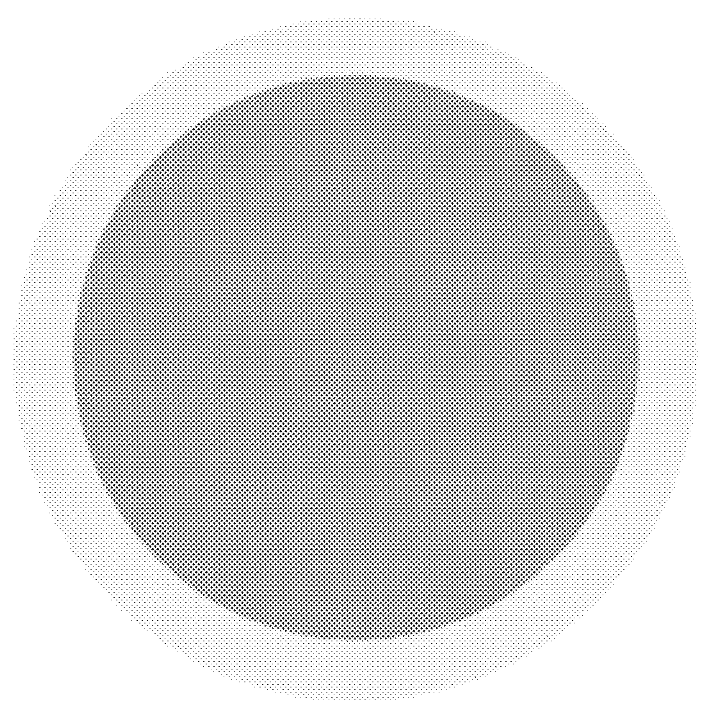
Figure 22:
Figure 23:
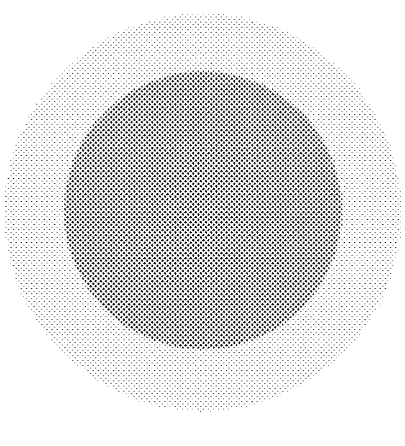
Figure 25:
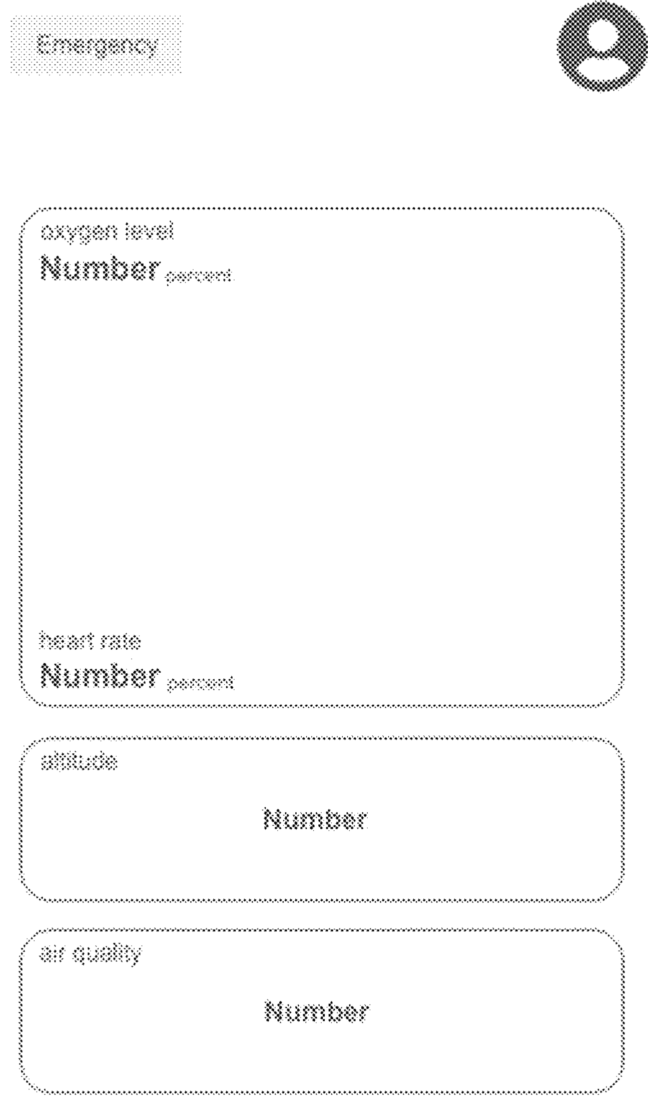
Figure 25:
Figure 25:
Figure 25:
Figure 25:
Figure 26:
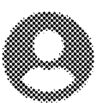
Figure 26:
Figure 26:
Figure 26:
Figure 26:
Figure 27:
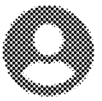
Figure 27:
Figure 27:
Figure 27:
Figure 27:
Figure 28:
Figure 28:
Figure 28:
Figure 28:
Figure 28:
Figure 29:
Figure 29:
Figure 29:
Figure 29:
Figure 29:
Figure 30:
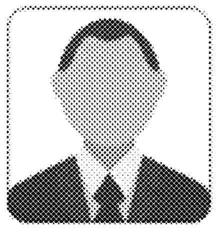
Figure 30:
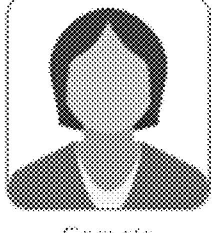
Figure 32:
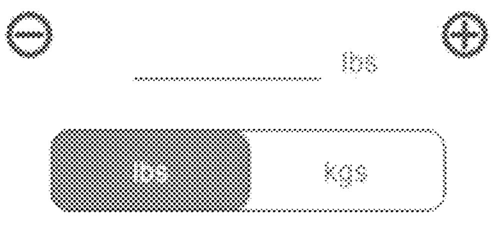

FIGS. 15-19 show welcome screens describing the mobile app's functionality, and via which a user can sign up for services (see FIG. 16), log in, set up, and personalize the mobile app. The mobile app can be personalized, for example, to include a representation of one or more safe blood oxygen saturation (SpO2) thresholds, such that a warning or alert is generated when the wearer's SpO2 is detected, by the wearable oxygen monitor, as being too low. FIG. 20 shows a synchronization request, in which the mobile app requests the user's input ("OK") to authorize the mobile app to establish a Bluetooth® connection and synchronize ("sync") the mobile app, via the Bluetooth® connection, with the wearable oxygen monitor. The user interface appearance, during synchronization, is shown in FIG. 21. FIG. 22 shows the login screen, and FIG. 23 shows an option for the user to "Get Started," for example after a first login event by the user. FIGS. 24-36 show user interfaces of a questionnaire requesting input from the user as to: whether they are from the U.S., what the emergency threshold values for oxygen level, heart rate, altitude and air quality should be, settings (alerts and notifications, location services, unit preferences, language preference, app sync, and other personalization), profile data (name, age, gender, weight, pulmonary hypertension (PH) class (e.g., pulmonary arterial hypertension (PAH), pulmonary hypertension owing to left heart disease, chronic obstructive pulmonary disease, chronic thromboembolic pulmonary hypertension (CTEPH), or pulmonary hypertension with unclear multifactorial mechanisms), safe threshold, medication(s), and allergies/reactions), journal personalization, emergency information (emergency contacts, doctor's notes, notes for EMS), gender, birth month and year, weight, whether or not they have a cardiovascular disease, and whether or not they have pulmonary hypertension (and, if so, what World Health Organization (WHO) classification). FIG. 34 shows a login screen, which may be completed by a user prior to accessing any of FIGS. 24-33 and FIGS. 35-36, or after setting up a user account or completing the "sign up" process referenced in FIG. 22 (e.g., by answering questionnaire questions shown in FIGS. 24-33 and FIGS. 35-36).

Figure 37:
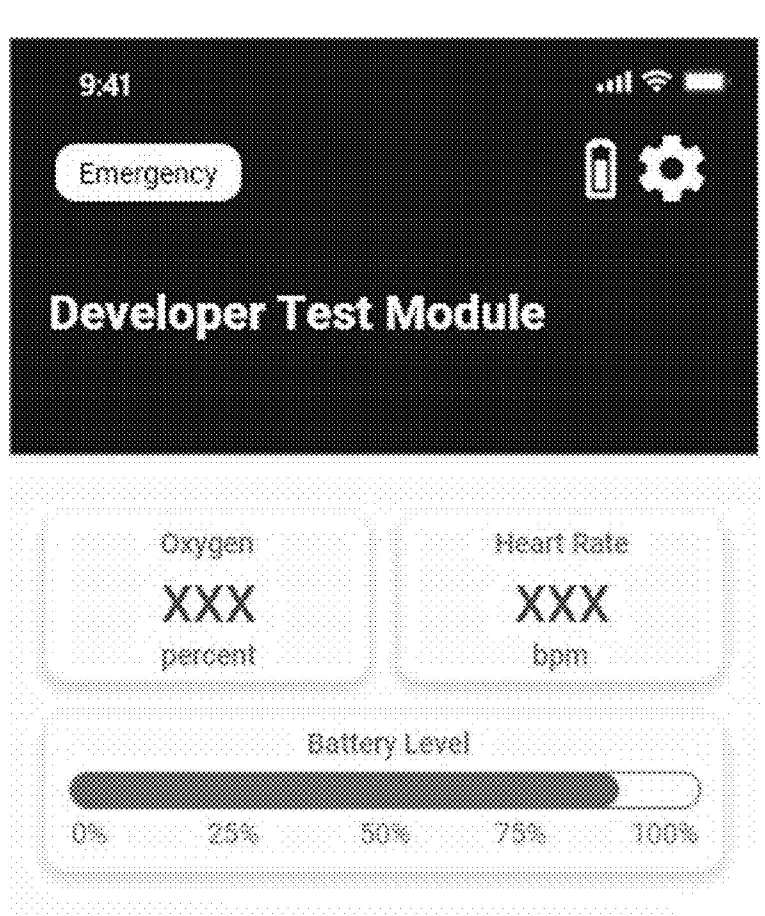
Figure 37:
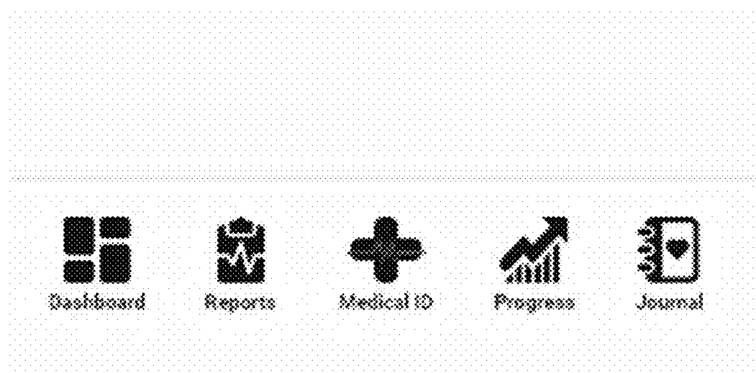
Figure 38:
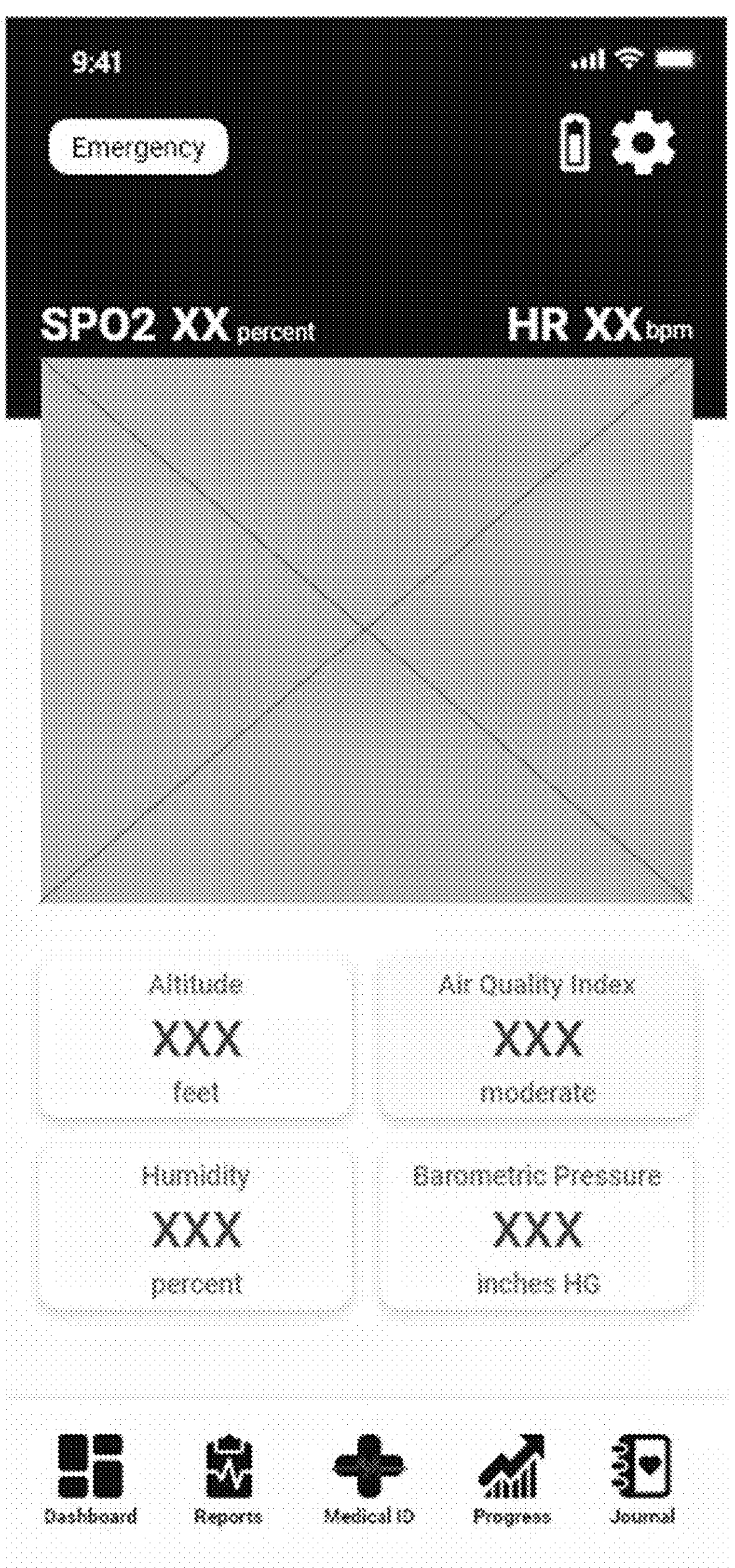
Figure 39:
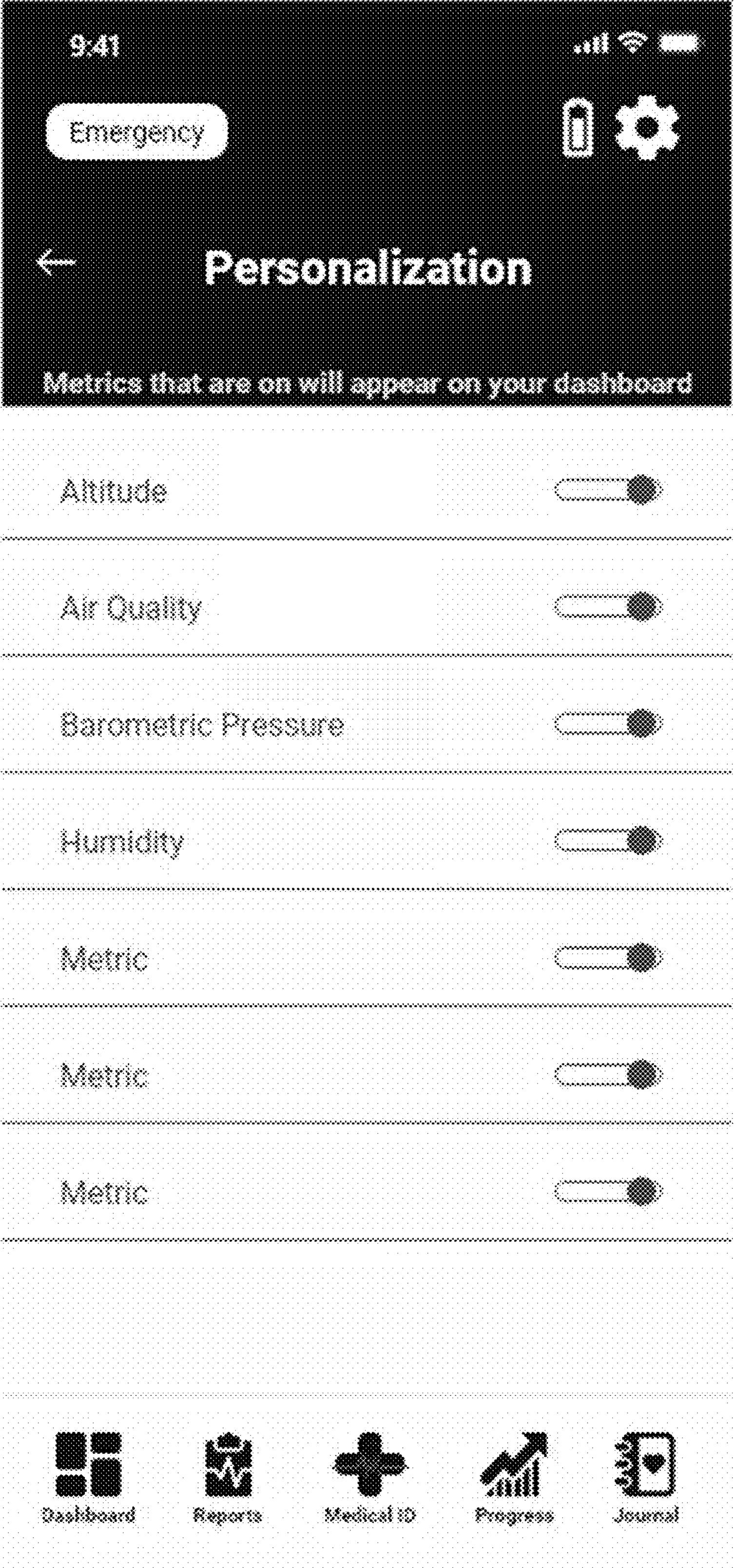
Figure 40:
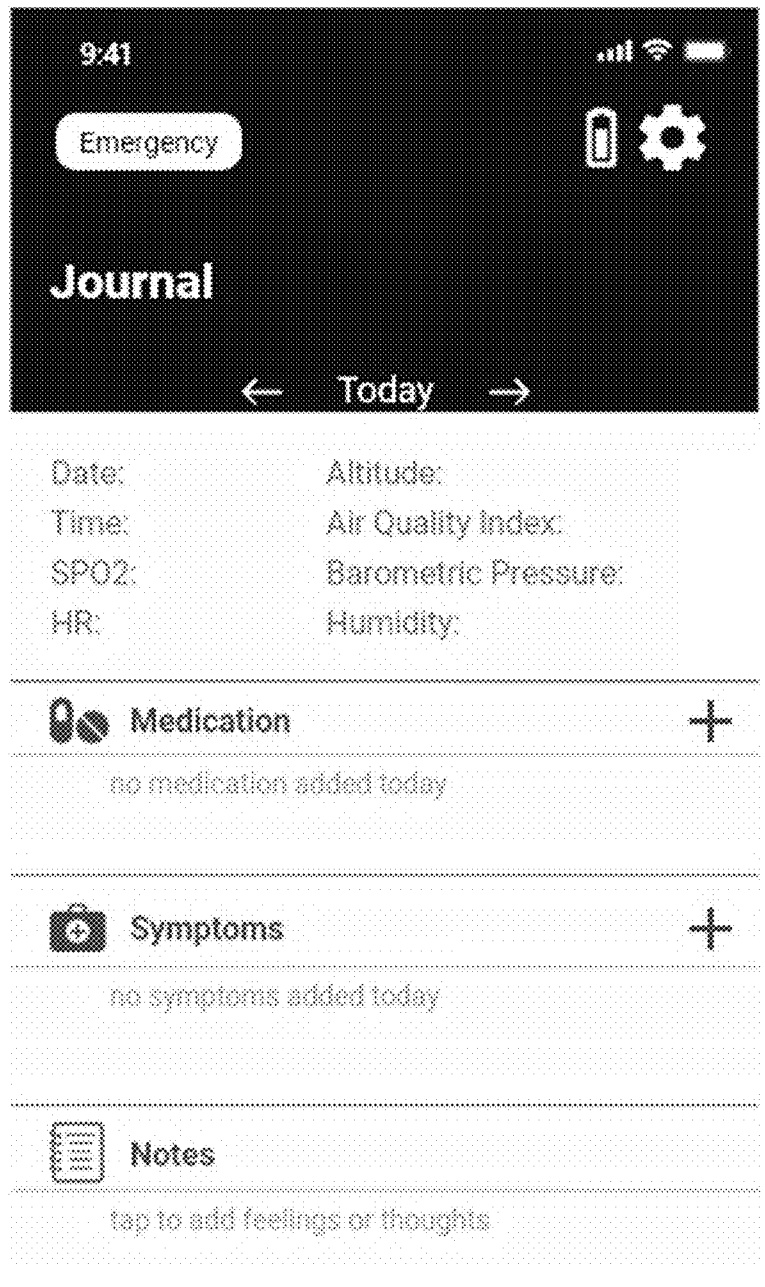
Figure 40:
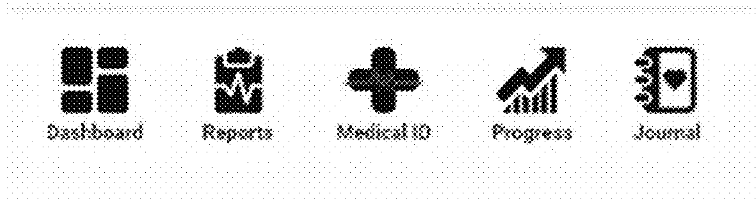
Figure 41:
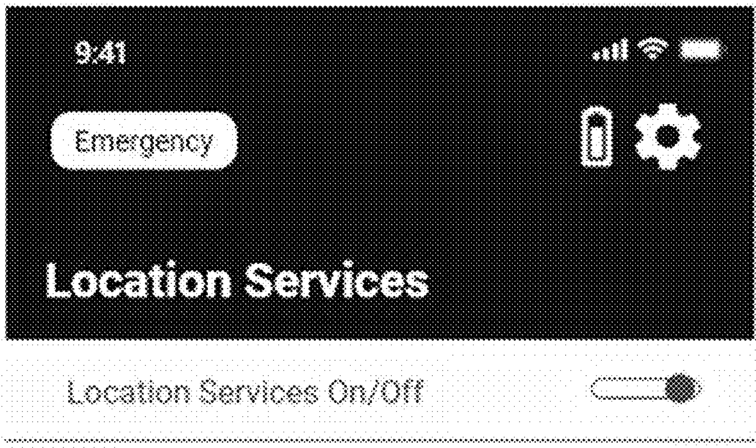
Figure 41:
Figure 42:
Figure 43:
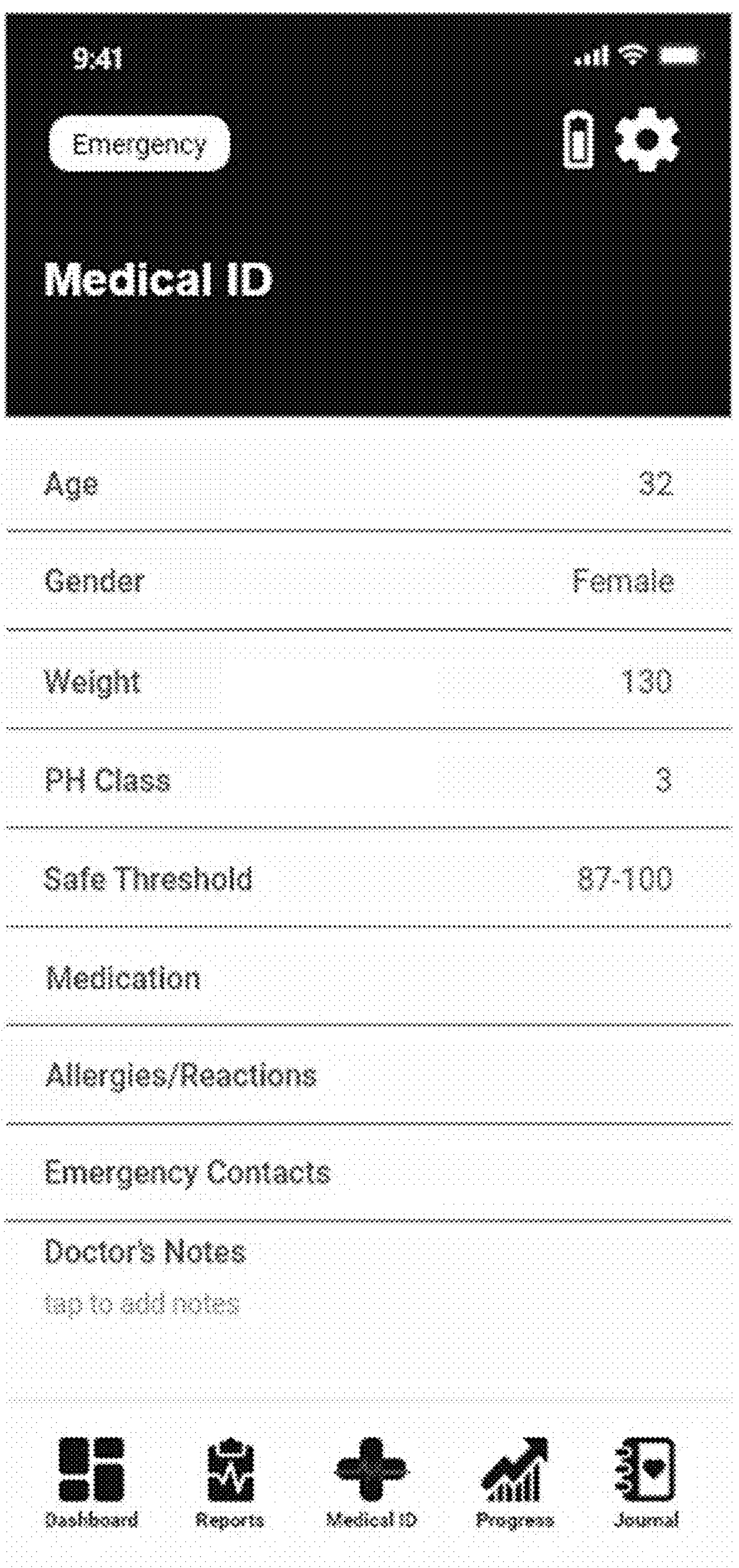
Figure 44:
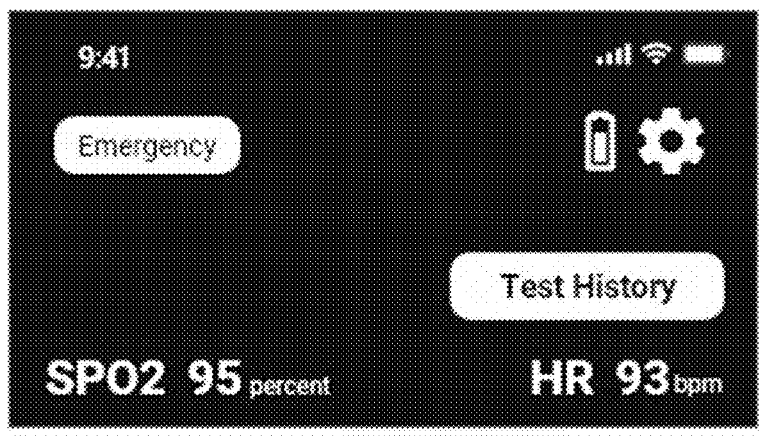
Figure 44:
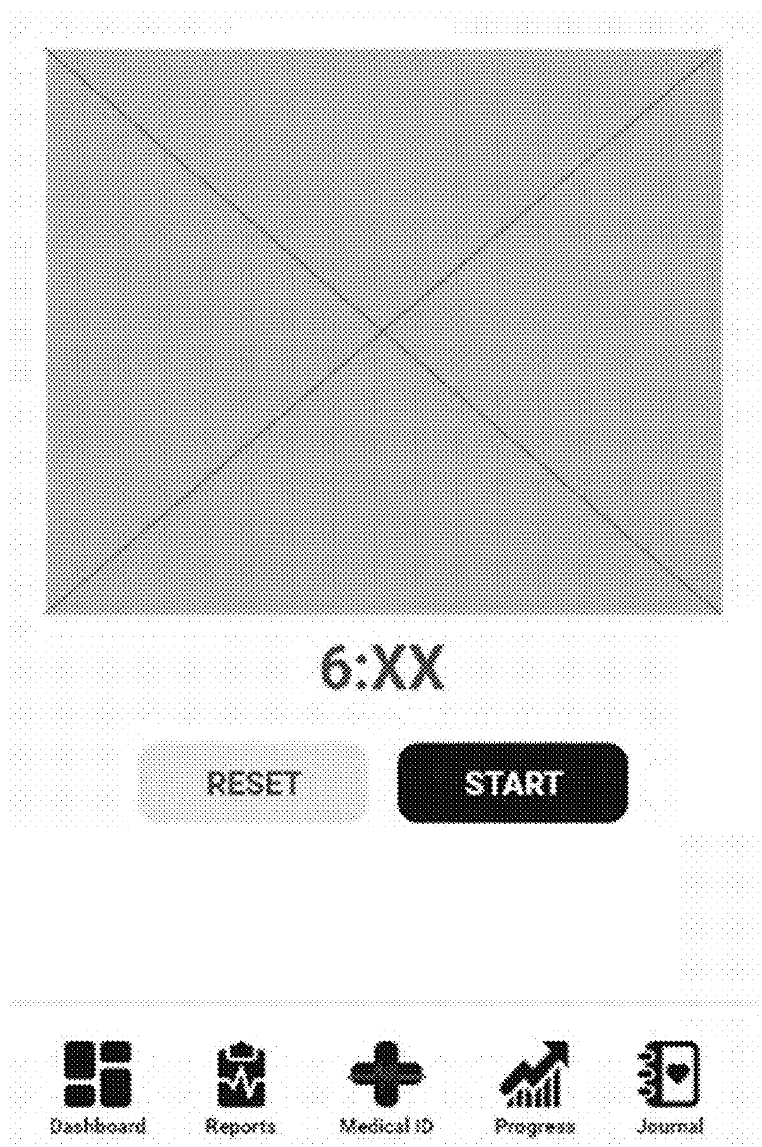
Figure 45:
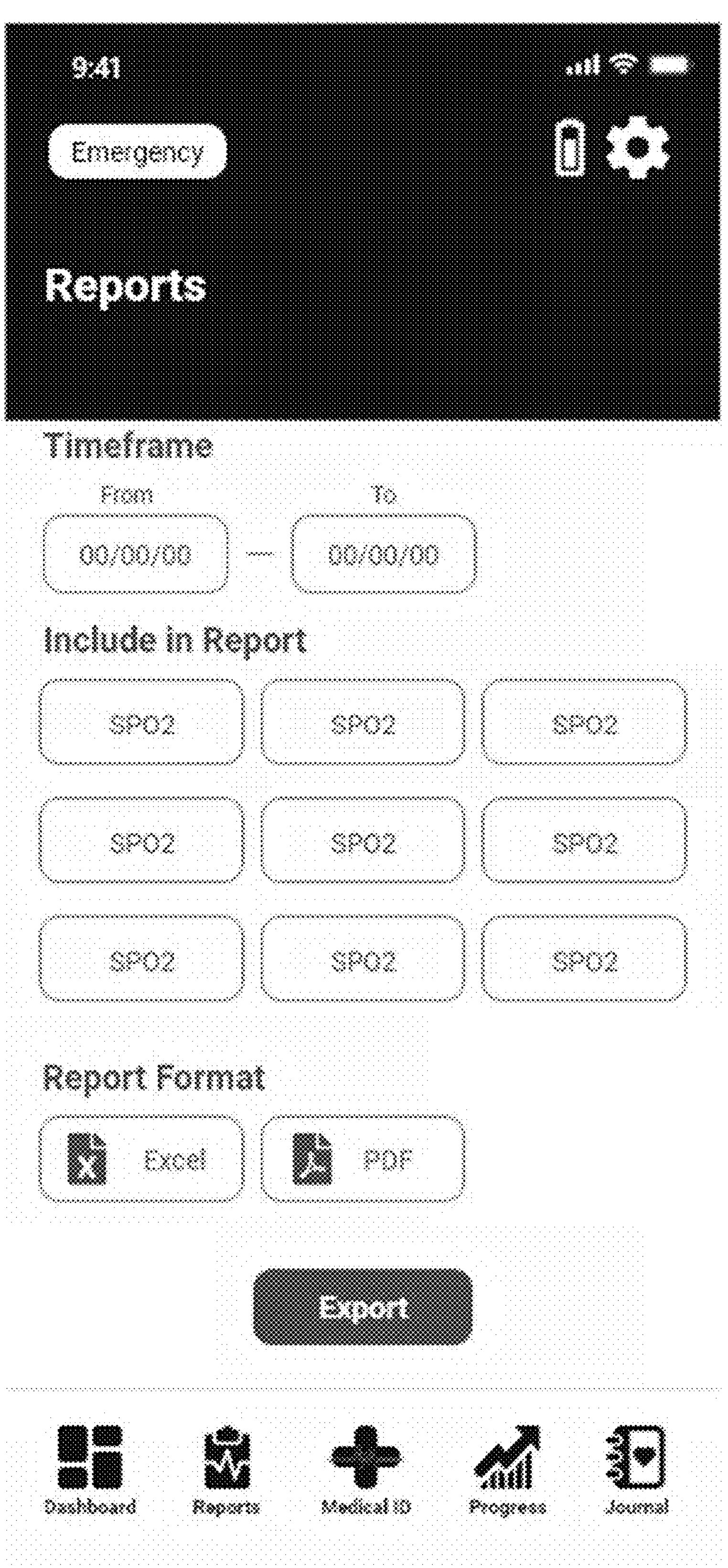
Figure 46:
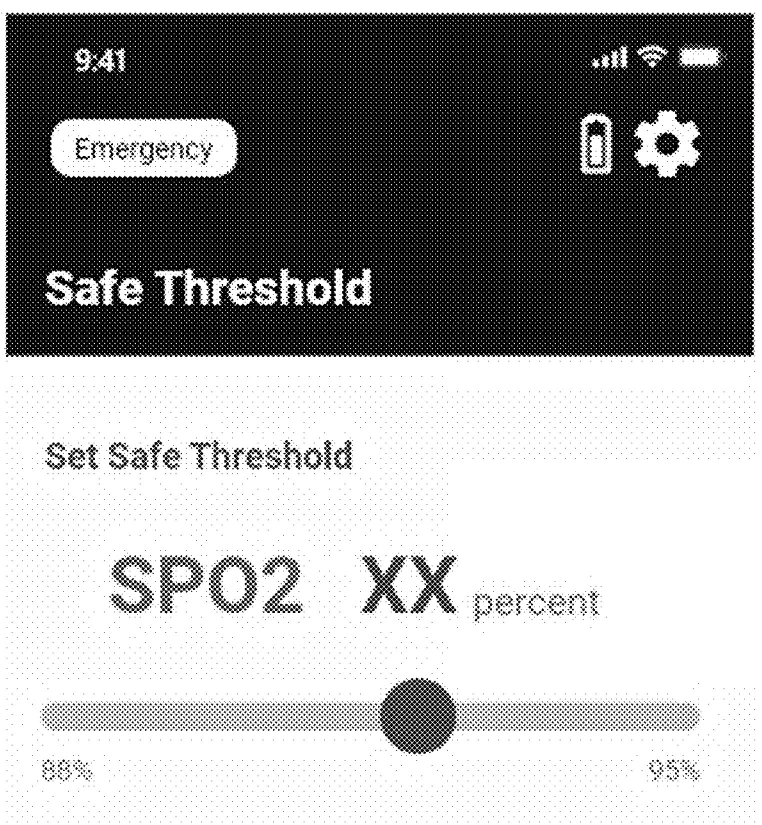
Figure 46:
Figure 47:
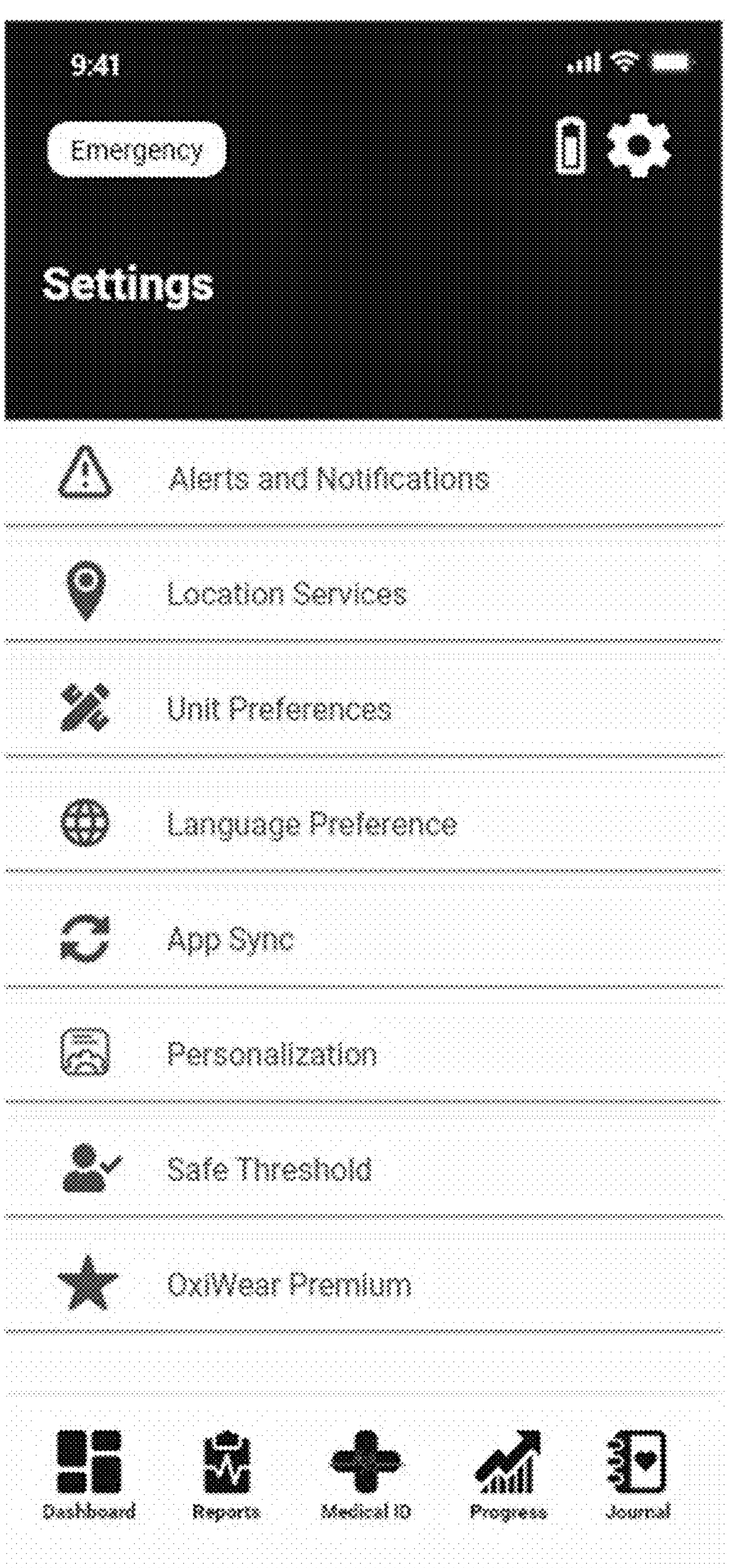
Figure 48:
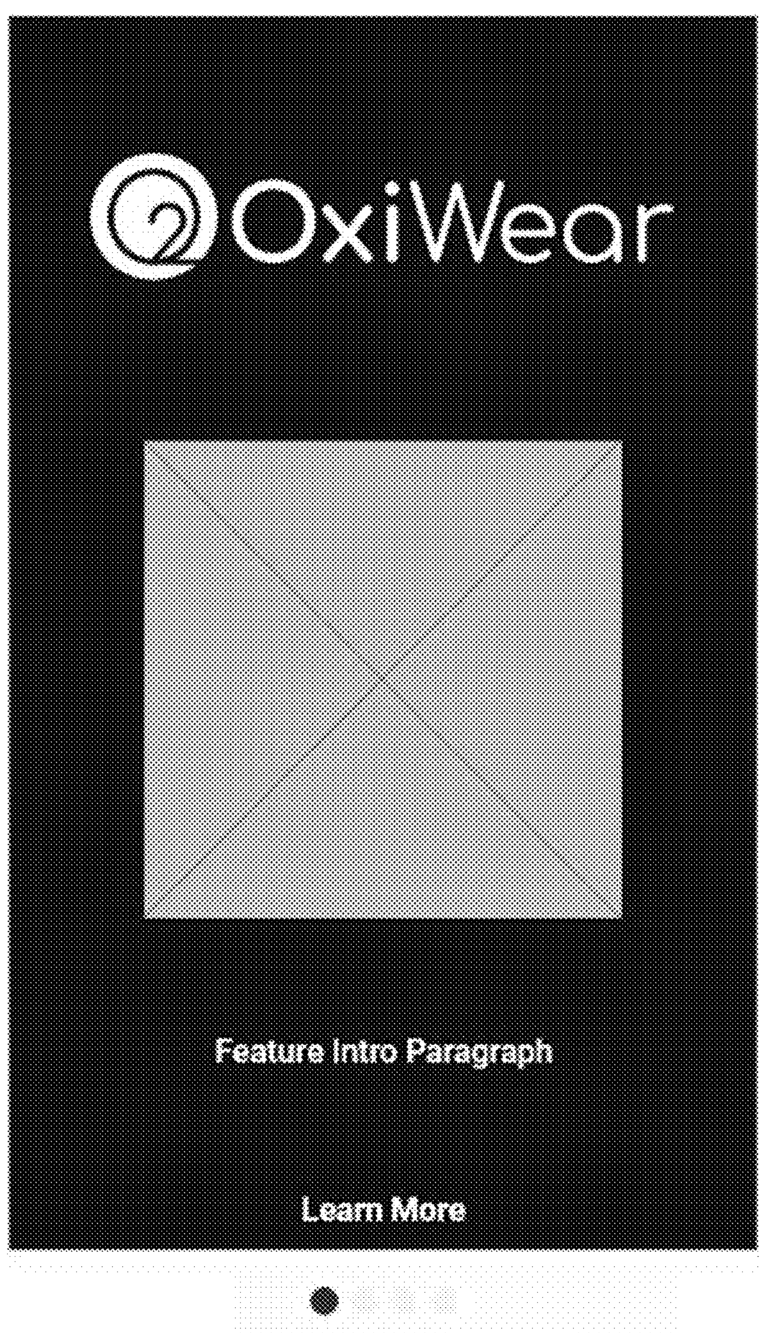
Figure 48:
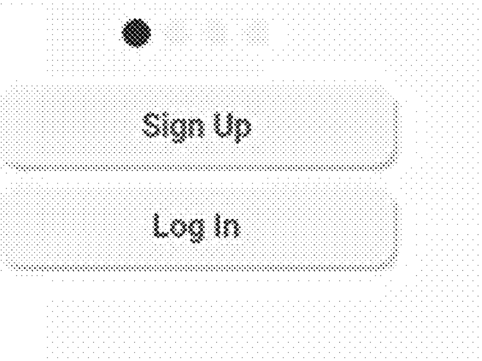

FIG. 37 shows a developer test module screen with a battery level indication and current oxygen level (percentage) and heart rate (beats per minute, BPM) readings. FIG. 38 shows current blood oxygen saturation level (percentage) and heart rate (beats per minute, BPM) readings, along with current altitude (feet), humidity (percent), air quality index (e.g., good, moderate, poor), and barometric pressure (inches mercury (Hg)). FIG. 39 shows a user interface via which the user can select which metrics they wish to have appear on their dashboard page. FIG. 40 shows an example journal entry for the current day, with date, time, SpO2, heart rate, altitude, air quality index, barometric pressure, and humidity values (e.g., average values, high values, etc.), together with medications taken on the current day (if any), symptoms experienced on the current day (if any), and notes entered by the user (if any). FIG. 41 shows a Location Services user interface, via which the user can turn location services (e.g., GPS location) on or off, using a slider. FIG. 42 shows a user interface accessible, for example, to users having a premium account, or providing the user with option to sign up for a premium account. The premium account can provide the user access to features such as predictive analysis, detailed report generation, and the presentation of weekly and monthly vital signs via the mobile app dashboard. FIG. 43 is a user interface showing a populated Medical ID tab. FIG. 44 is a user interface showing current oxygen level (percentage) and heart rate (BPM) readings, along with a resettable timer. FIG. 45 is a user interface showing user-selectable options for report generation, including timeframe, vital signs of interest, and report format (e.g., Microsoft® Excel® or Adobe® PDF®). FIG. 46 shows a Safe Threshold user interface, via which the user can set a threshold percentage SpO2 value, using a slider, and select "Done" when complete. FIG. 47 is a user interface showing Settings after Safe Thresholds have been set and a premium account has been established (as contrasted with the Settings shown in FIG. 26, which do not include a Safe Threshold or OxiWear Premium line item). FIG. 48 is a user interface showing an example landing screen that may display when the mobile app is first launched/opened (i.e., the first screen that a first-time user will see, and via which he/she can register for an account).

Figure 49:
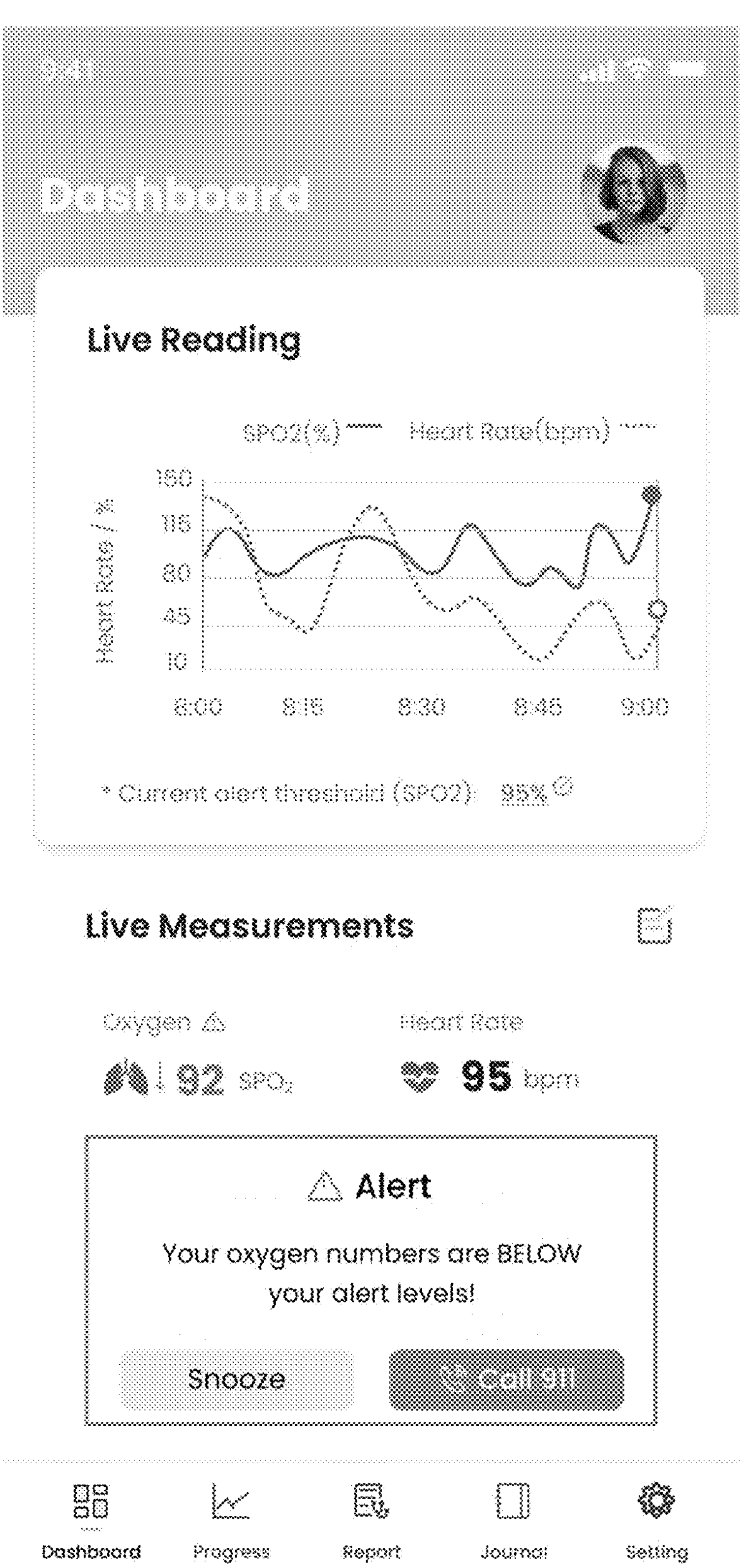
Figure 50:
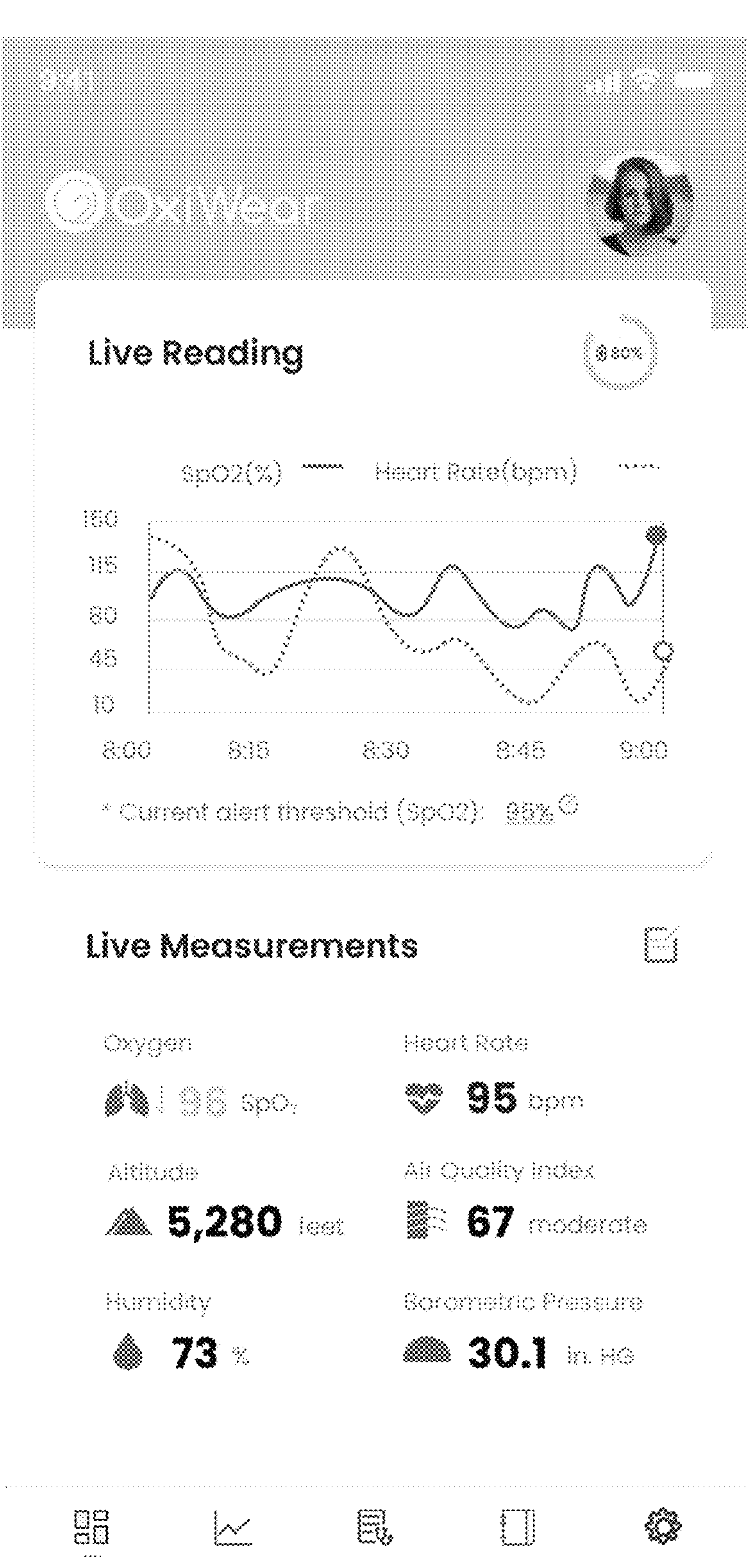
Figure 60:
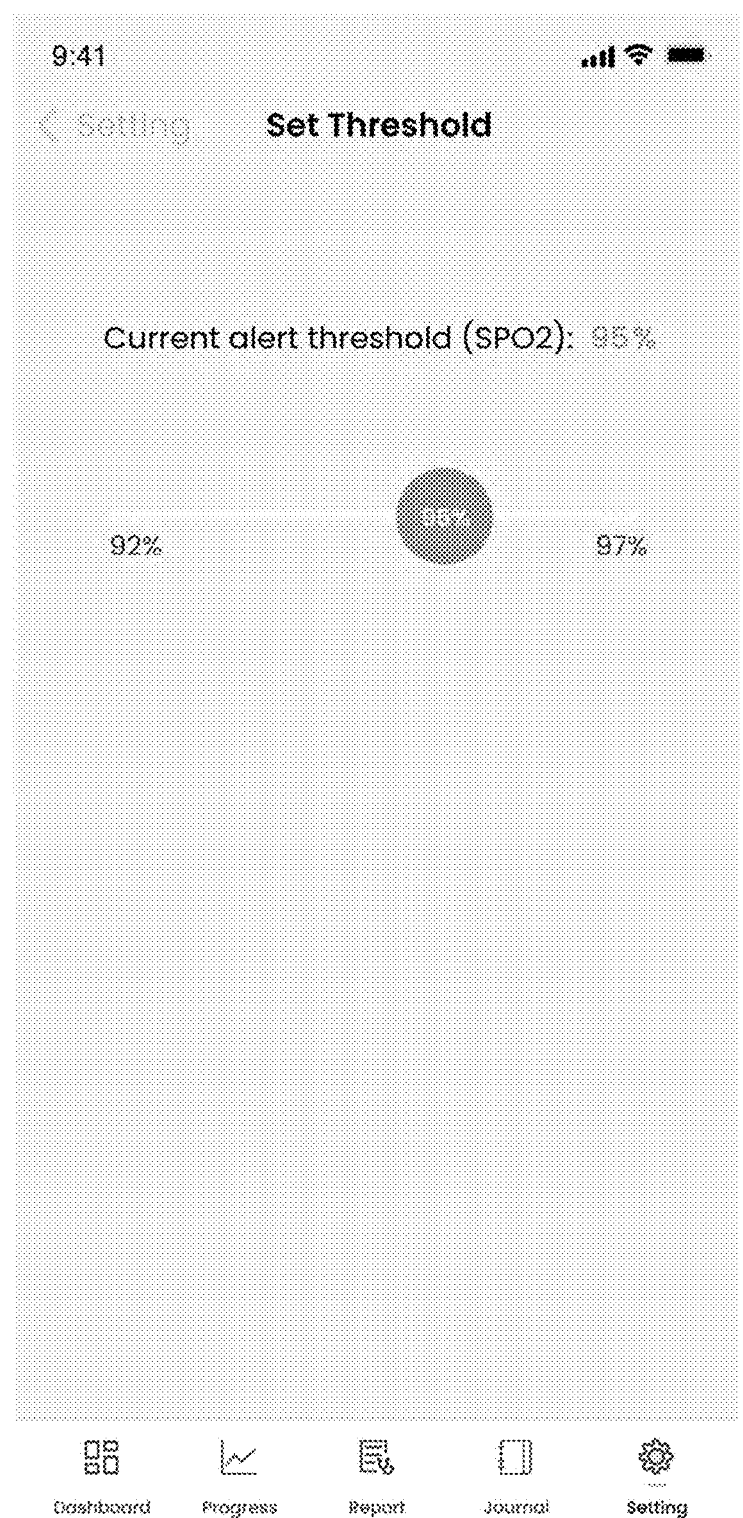

FIG. 49 shows a user interface including an alert sub-window disposed over a dashboard window, the alert sub-window being displayed in response to one or more $SpO_2$ indicators being below a pre-determined threshold. In at least some embodiments, said pre-determined threshold is specified by a user as shown in FIG. 60. The alert sub-window comprises a user interface comprising one or more buttons that a user can interact with. For example, a user can interact with a snooze button to suppress the alert sub-window (e.g., for a predefined period of time, such as 5 minutes, 10 minutes, 30 minutes, etc.). The user can further interact with a "call 911" button configured to initiate a telephone call to an emergency dispatch office. FIG. 50 shows a dashboard depicting a plurality of measurements including biometric measurements for a user as well as factors that relate to or contribute to a user's oxygen level. For example, said plurality of measurements can include one or more live biometric readings for $SpO_2$ blood oxygen level and/or heart rate. Said plurality of measurements can also comprise one or more environmental measurements for altitude, air quality index, humidity, and or barometric pressure. The dashboard can also depict a record of one or more previous measurements in graphical form. For example, a plurality of $SpO_2$ and heart rate measurements sampled within the previous hour (or any other desired preceding time period) can be plotted on a graph, and said graph can be updated, in real time or substantially in real time, in response to new measurements of oxygen levels and heart rates.

Figure 51:
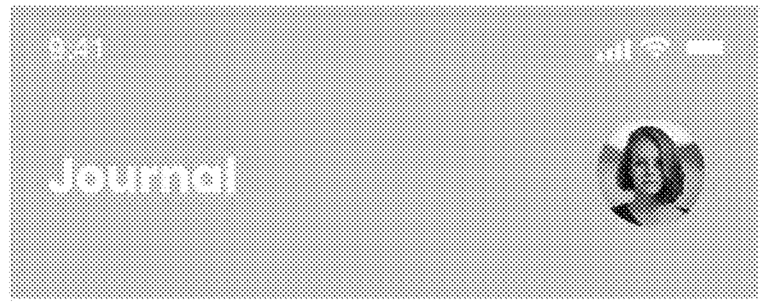
Figure 51:

FIG. 51 shows a user interface comprising a monthly/calendar view of a user's journal entries. A user can enter a journal entry for a particular day using, for example, the interface shown in FIG. 40. Said journal entry can comprise date, time, $SpO_2$, heart rate, altitude, air quality index, barometric pressure, and humidity values (e.g., average values, high values, etc.), together with medications taken on the current day (if any), symptoms experienced on the current day (if any), exercise and/or physical activity completed (if any), and notes entered by the user (if any). A user can interact with a calendar for a given month to view any journal entries entered for a day in the given month. A user can further use the calendar to select a day to enter a new journal entry for by interacting with a "+" icon or a similar interface/GUI element. A user can further use the calendar to search for a previous journal entry (e.g., using a keyword search, bu interacting with the magnifying glass icon or similar interface/GUI element).

Figure 52:
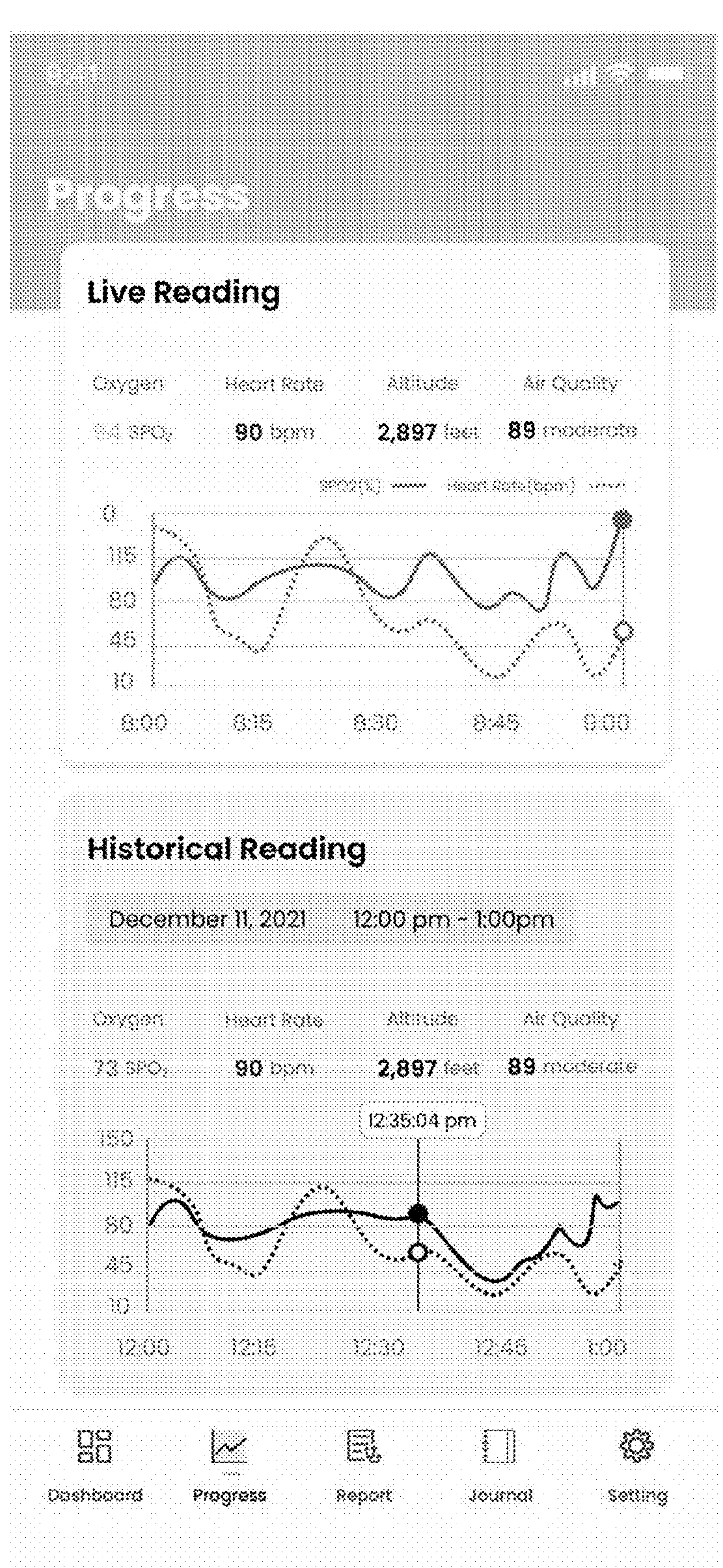

FIG. 52 shows a user interface comprising views of detected oxygen levels and heart rates. Said views can be, for example, in the form of a graph, plot, or chart. One view can depict a live reading that can be dynamically updated, in real time or substantially in real time, in response to new measurements of oxygen levels and heart rates. A second view can depict a plurality of detected oxygen levels, heart rates, and/or other measurements measured within a period defined by the user through a GUI. Said period can comprise a past time period and/or a past date/range (i.e., historical data/readings) for which the measurements were recorded.

Figure 53:
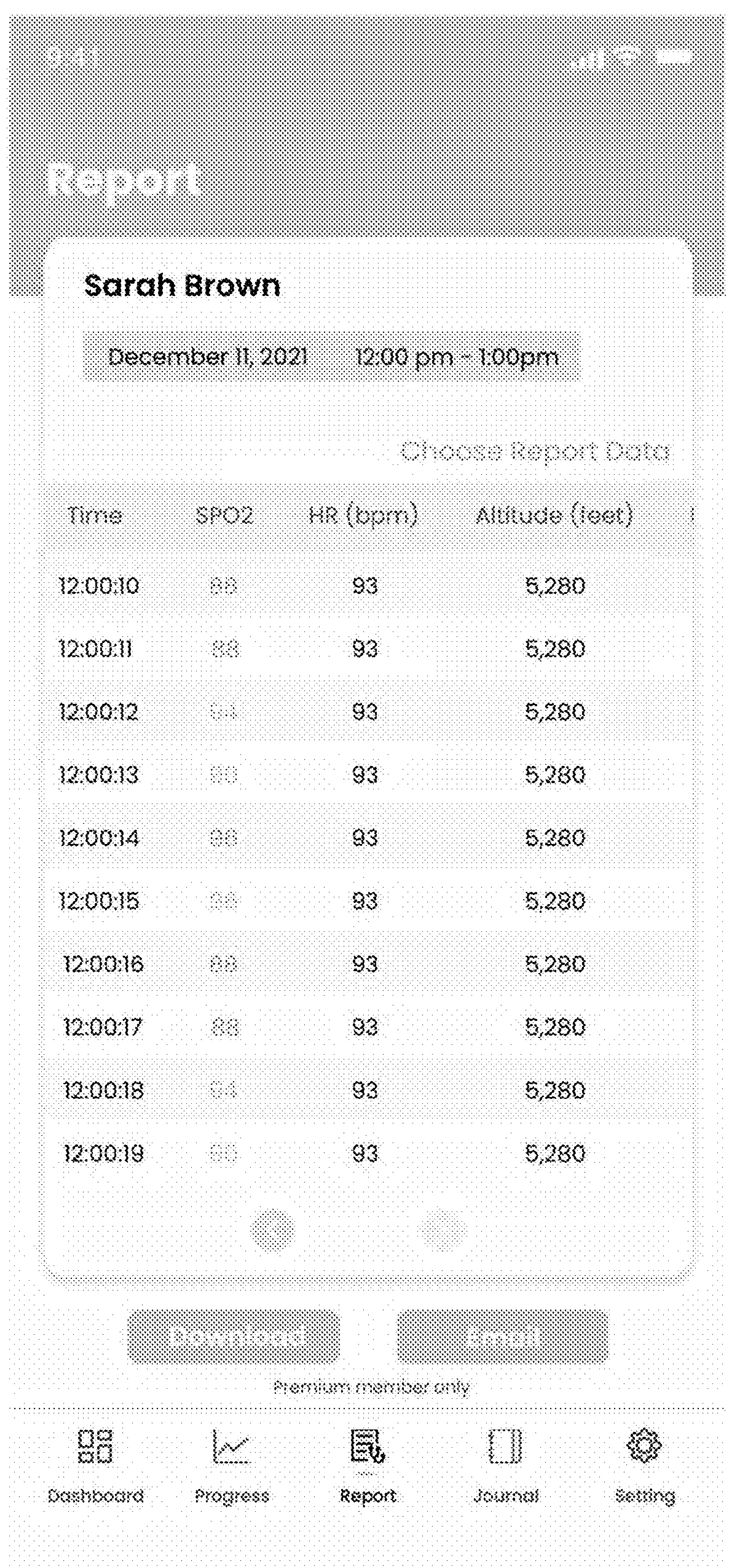

FIG. 53 shows a user interface for viewing and configuring a report. Said report can comprise measurements collected over a period defined by a user. Said report can comprise at least one of a plurality of vital/biometric measurements and/or a plurality of environmental measurements. For example, said report can comprise a plurality of $SpO_2$, heart rate, and altitude measurements recorded or otherwise captured within a given period. Said period can comprise a past date (or date range) and/or time (or time range) defined by a user through a GUI. A user can download the report (e.g., as a file for viewing and/or local storage) and/or can generate and send an email containing the report via the user interface.

Figure 54:
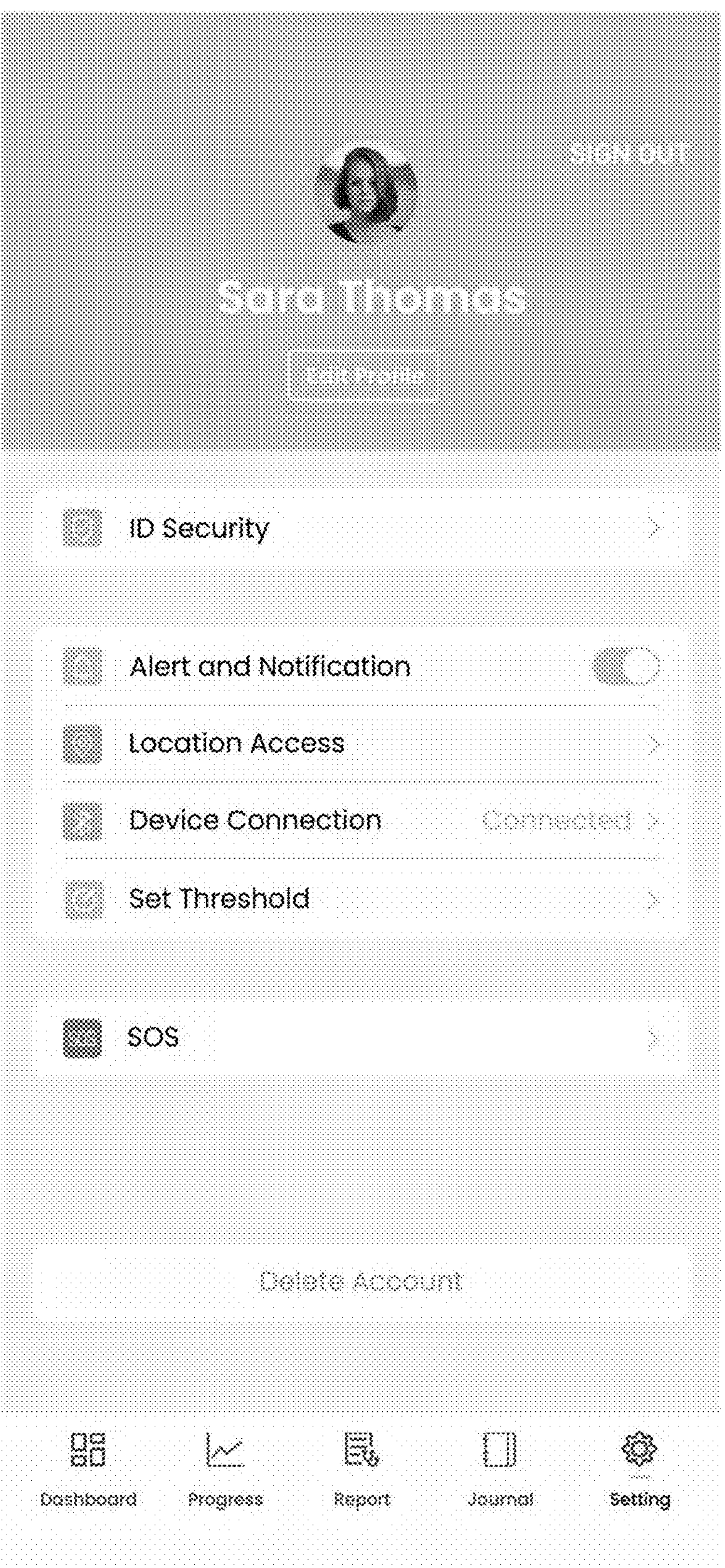
Figure 59:
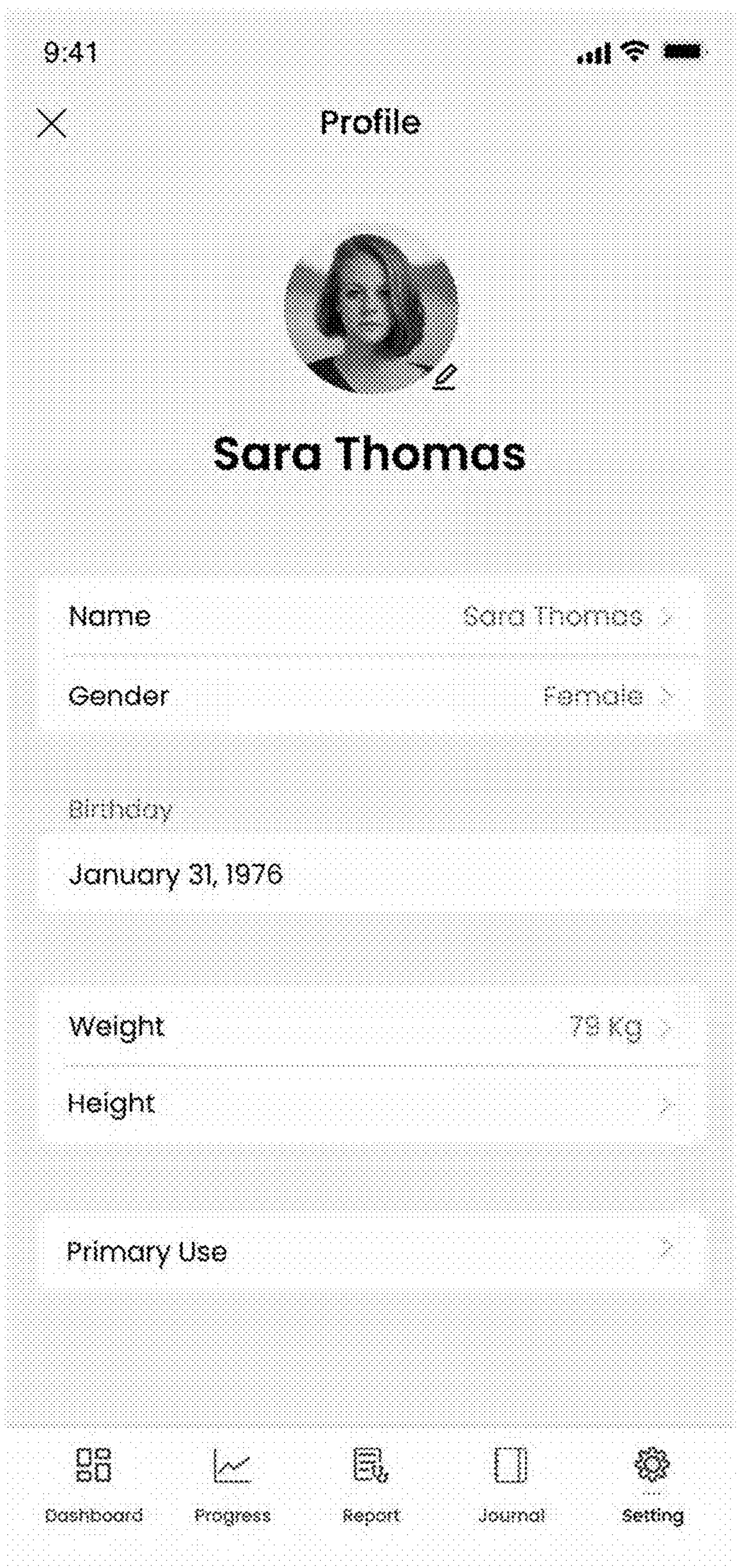

FIG. 54 shows a user interface through which a user can access a plurality of settings. The settings can include, for example, ID Security settings, an alert and notification toggle, location access settings, Bluetooth® and similar device connection settings related to a wireless communications protocol, threshold settings, and/or SOS/emergency notification settings. The user interface can be configured to provide users access to a GUI to edit the user's profile, as shown in FIG. 59. The user interface can also provide a button that a user can use to delete the user's account.

Figure 55:
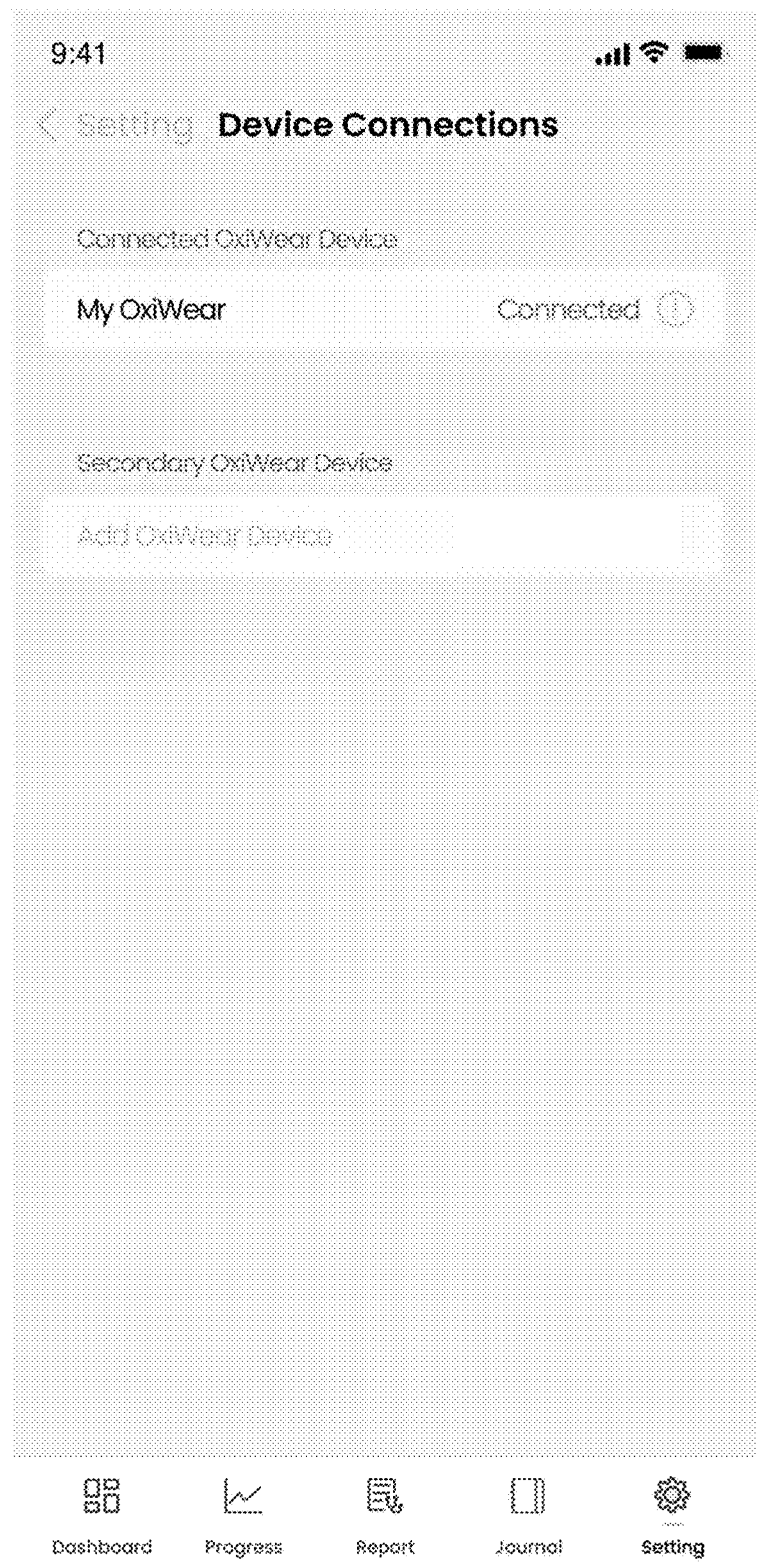

FIG. 55 shows a user interface through which a user can configure one or more connections between two or more devices. Said devices can comprise, for example, one or more wearable oxygen devices and a mobile device (e.g., a smartphone, tablet, laptop, smartwatch, or similar compute device). The mobile device can be the device on which the user interface of FIG. 55 is displayed. Said one or more connections can comprise, for example, one or more network connections using one or more wireless communications protocols (e.g., Bluetooth®, 4G®, 5G®, etc.). A user can access said user interface by interacting, for example, with the interface shown in FIG. 54.

Figure 56:
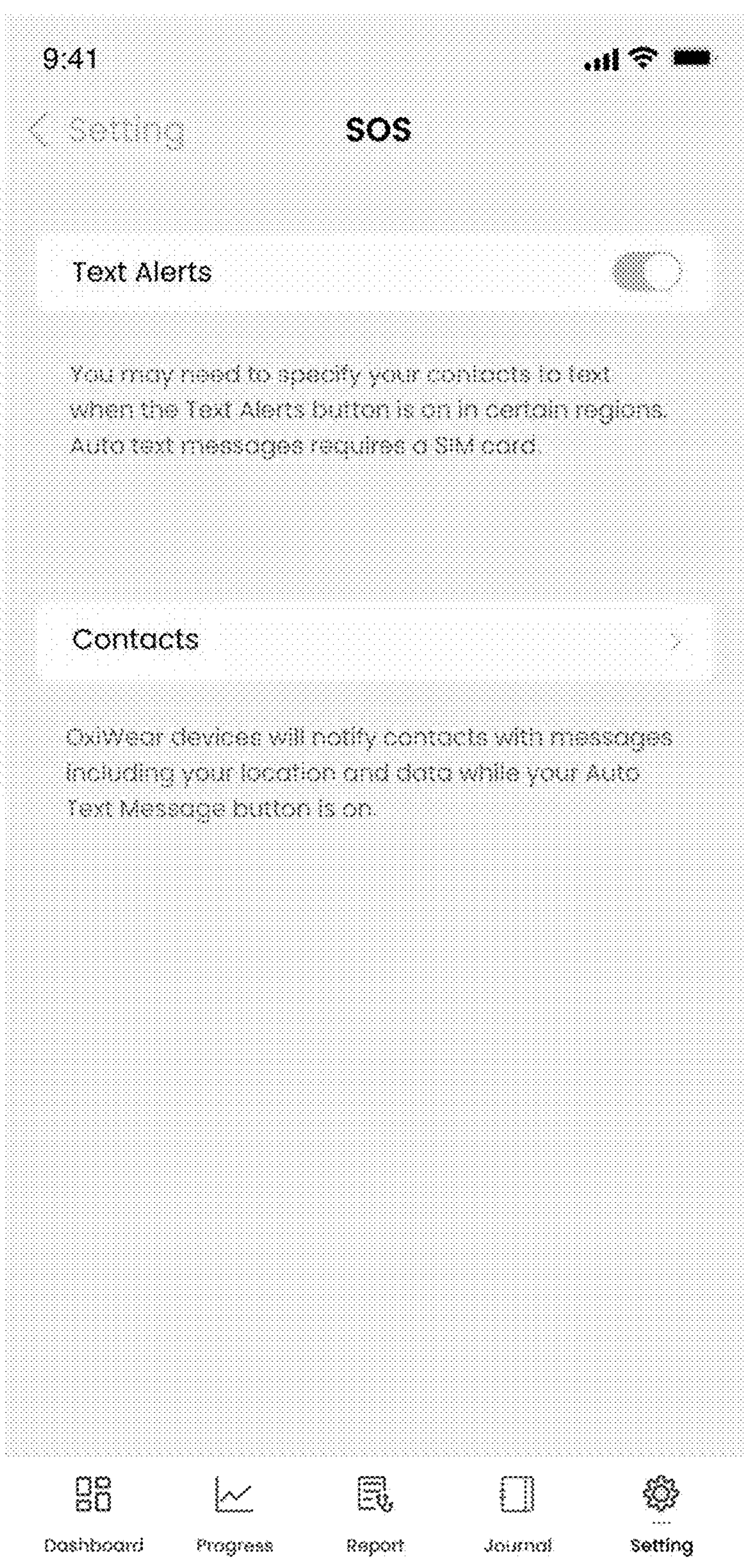

FIG. 56 shows a user interface for configuring SOS/emergency notification alerts. Said SOS alerts can comprise text alerts sent to one or more contacts defined by a user using said user interface. Said text alerts can comprise SMS text messages. A user can access said user interface using, for example, the interface shown in FIG. 54.

Figure 57:
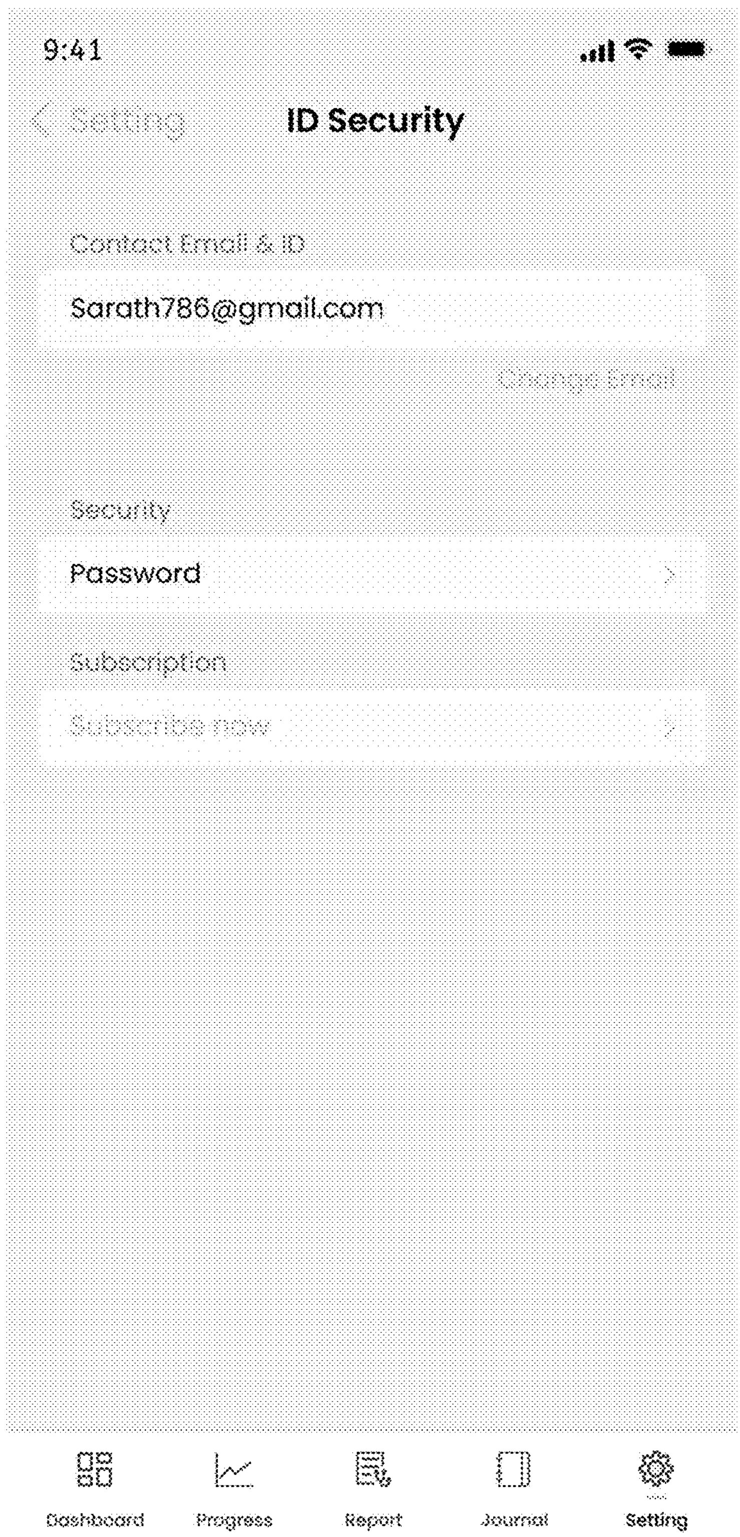

FIG. 57 shows a user interface for configuring ID security. A user can use said user interface for configuring/specifying the user's email address, wherein said email address can be used to contact and/or identify the user. A user can further use said user interface to update a password used for account access and/or to update a subscription plan associated with the user's account. A user can access said user interface using, for example, the interface shown in FIG. 54.

Figure 58:
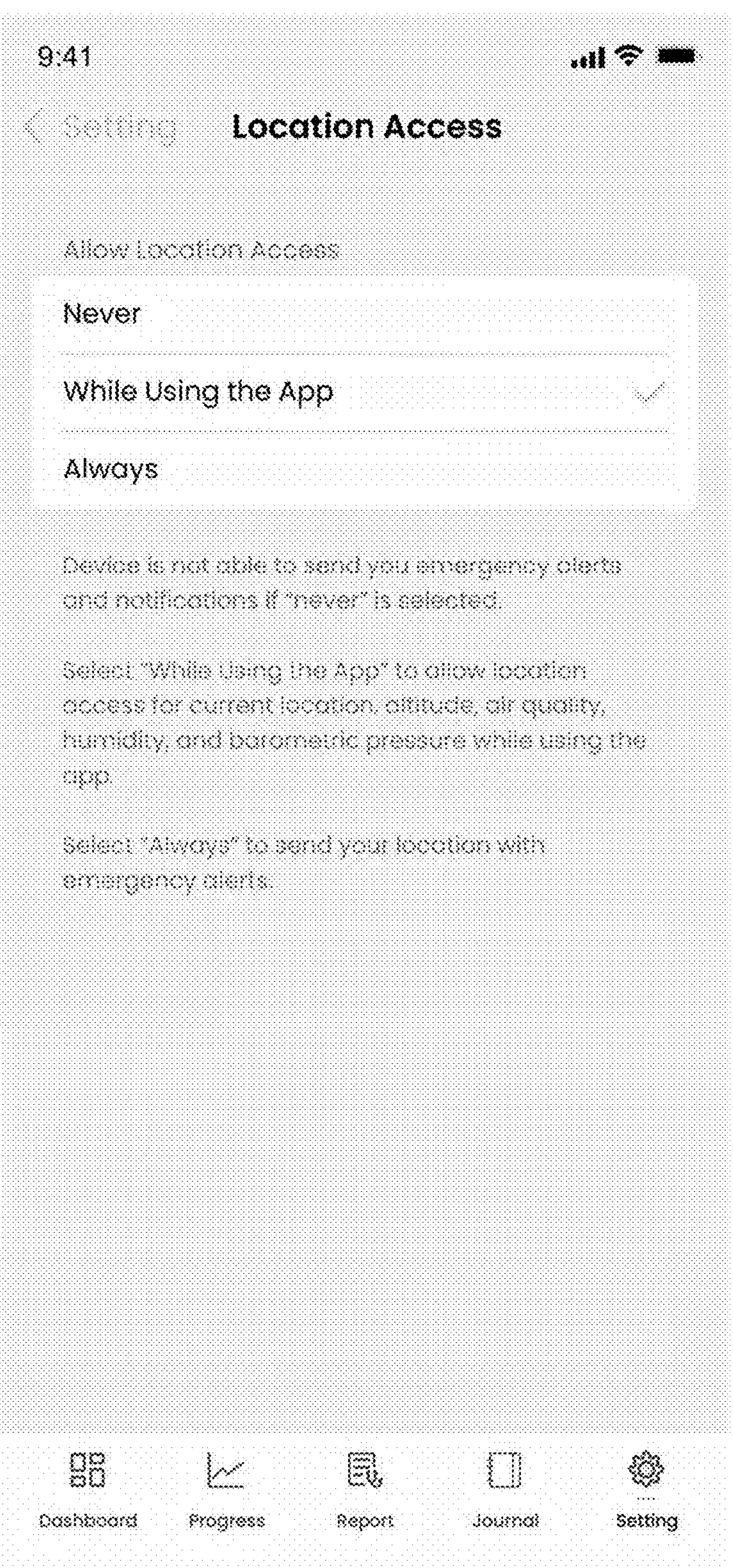

FIG. 58 shows a user interface for configuring location access in relation to a mobile app configured for use with one or more wearable oxygen devices. A user can configure location access to provide data indicating a user's geographic location to one or more programs related to a wearable oxygen device. A user can access said user interface using, for example, the interface shown in FIG. 54.

FIG. 59 shows a user interface for configuring a user profile. Said user interface can comprise a name field, gender field, birthday field, weight field, and/or height field. Said user interface can further be used to populate information about a primary user of one or more wearable oxygen devices. A user can access said user interface using, for example, the interface shown in FIG. 54.

FIG. 60 shows a user interface for configuring an $SpO_2$ threshold for triggering an alert. A user can set said $SpO_2$ threshold between a range of, for example, 92% and 97%. Said threshold can trigger, for example, the alert sub-window shown in FIG. 49. The user interface can include an interactive element such as a slider, drop-down menu, radio buttons, or any other graphical or text-based element, with which the user can interact to set the $SpO_2$ threshold. A user can access said user interface using, for example, the interface shown in FIG. 54.

Figure 61B:
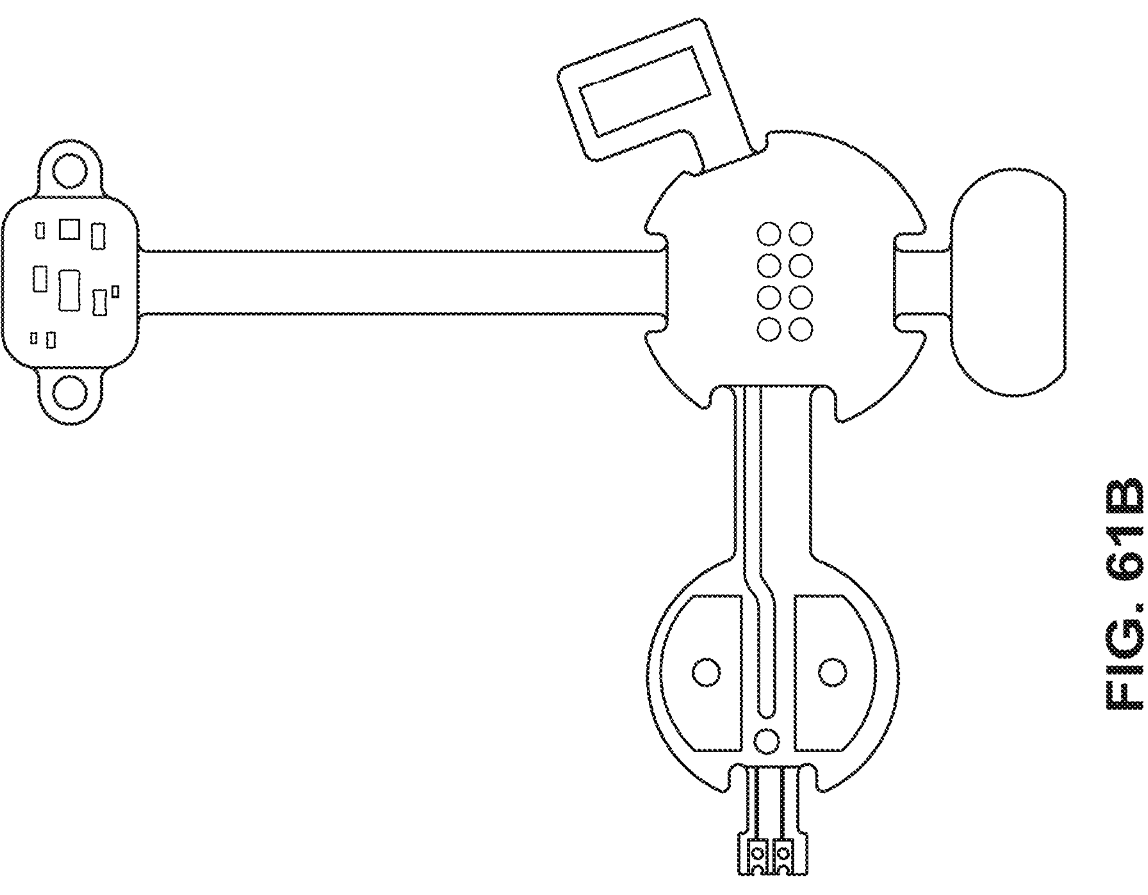
FIGS. 61A-61N are renderings of a flexible electronics assembly for a wearable oxygen monitor and components therein, according to some embodiments.
Figure 61A:
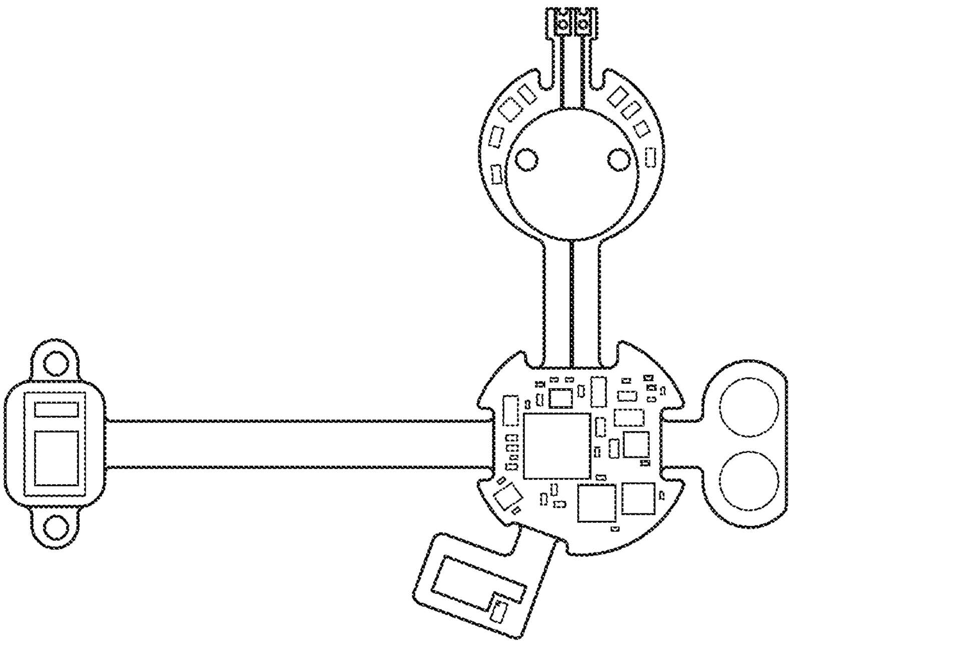
Figure 61D:
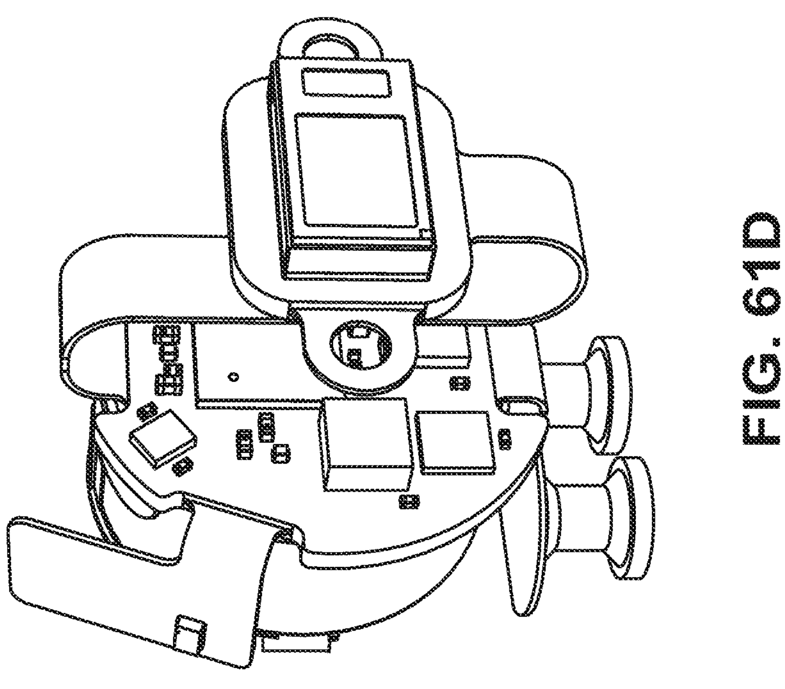
Figure 61C:
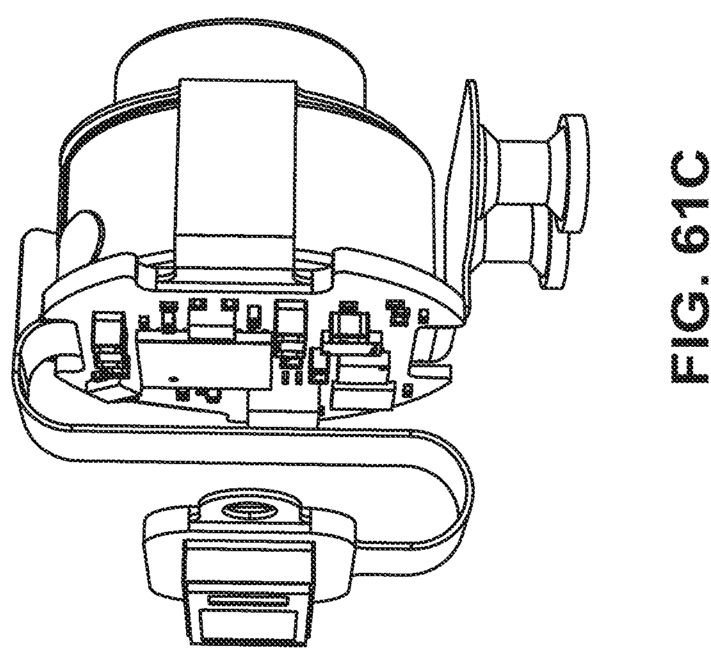
Figure 61F:
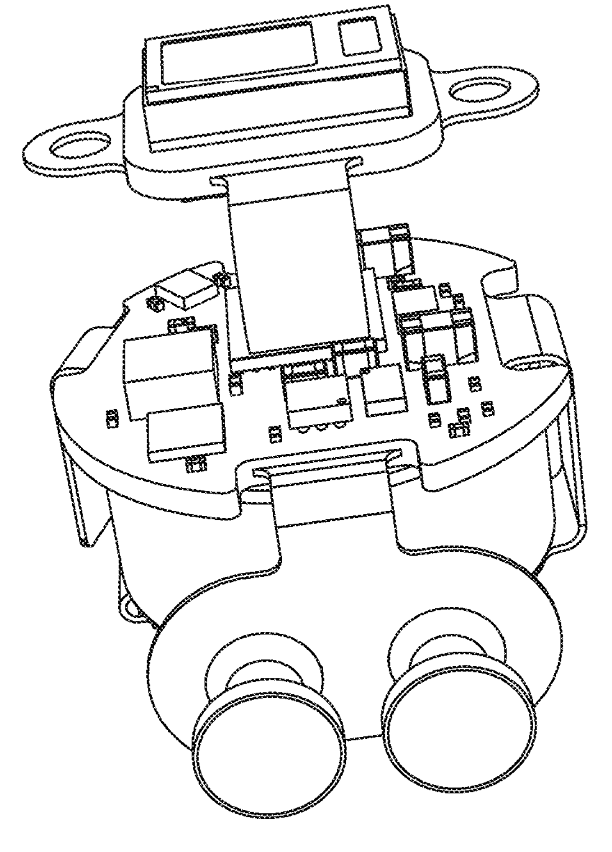
Figure 61E:
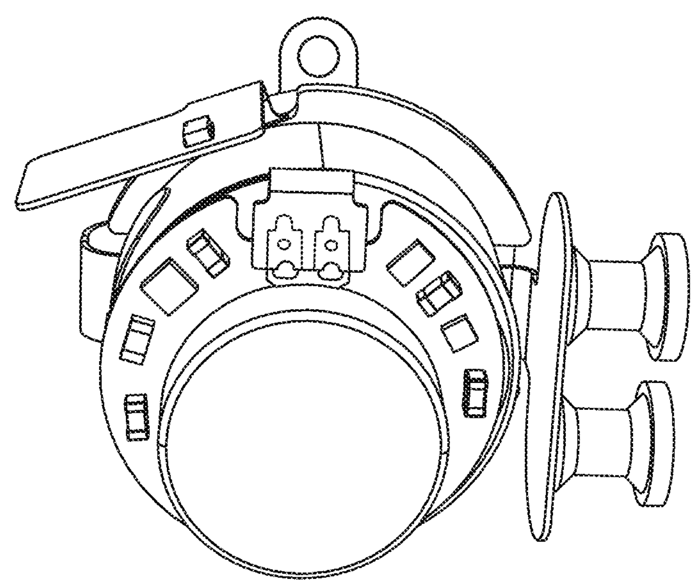
Figure 61G:
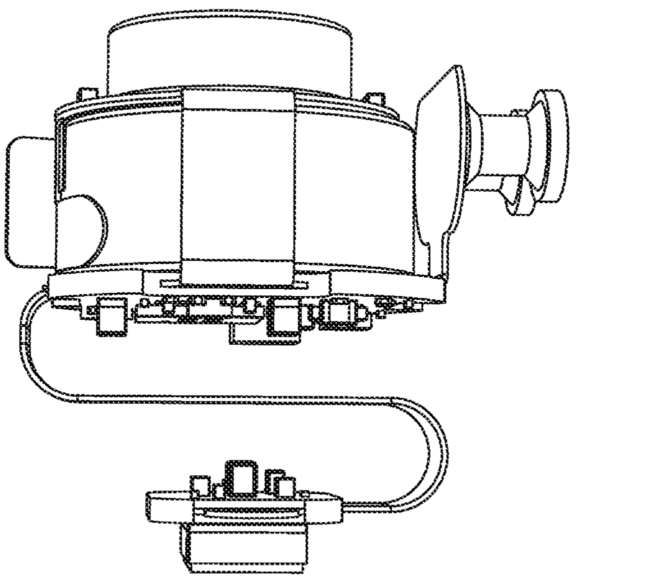
Figure 61H:
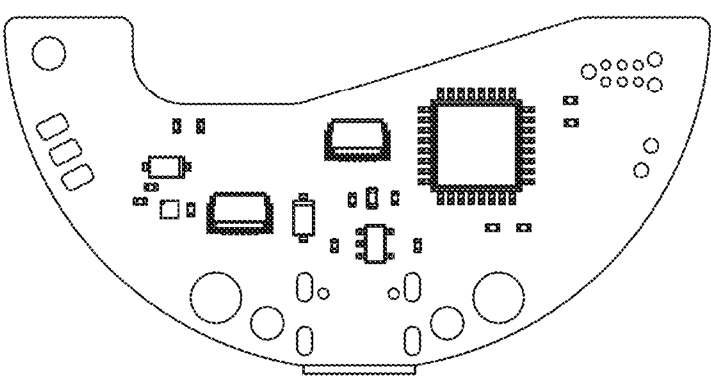
Figure 61I:
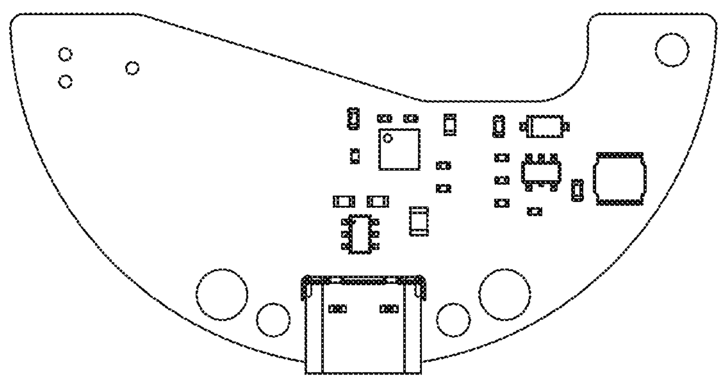
Figure 61J:
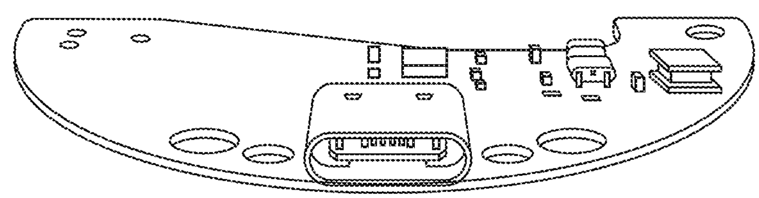
Figures 61K, 61L:
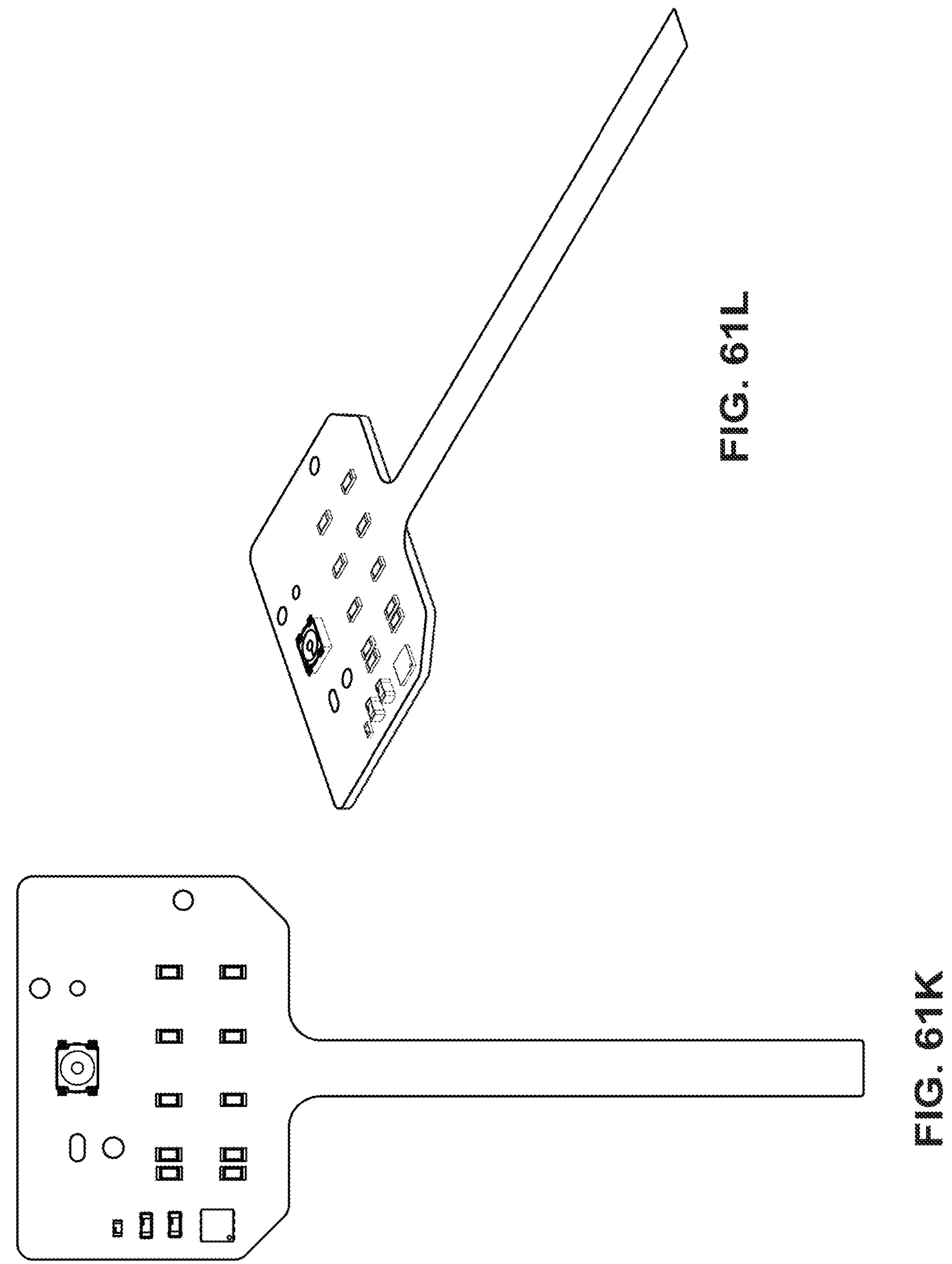
Figure 61N:
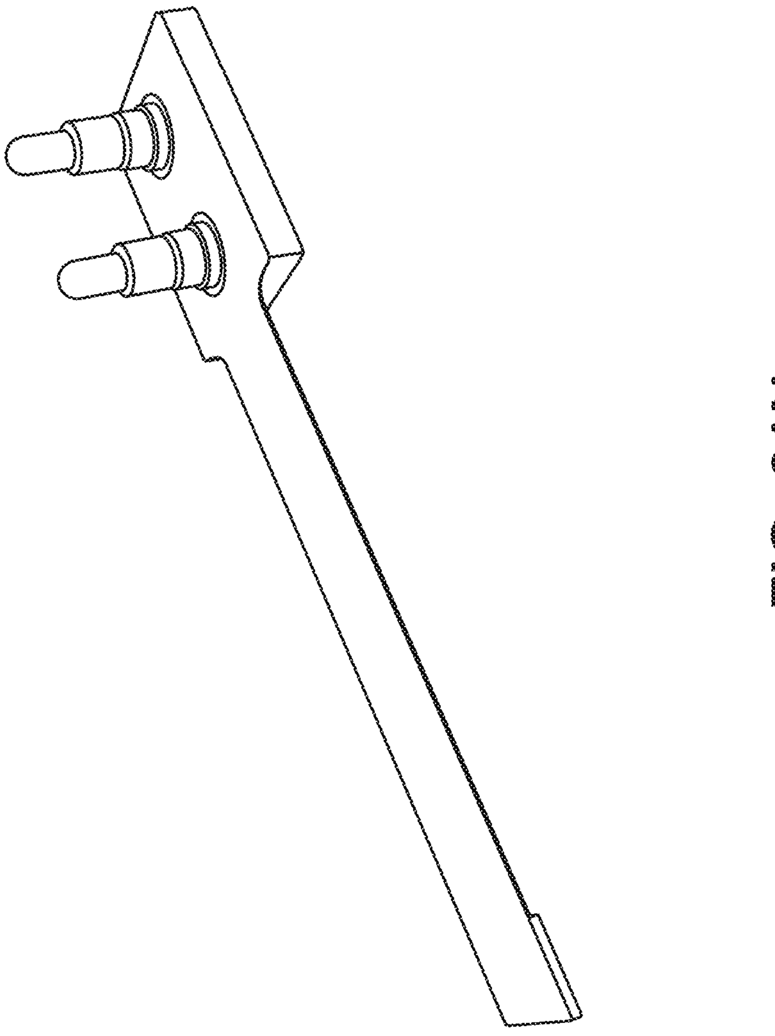
Figure 61M:

FIGS. 61A-61N include renderings of a flexible electronics assembly (e.g., electronics 760 of FIG. 7A-7C) for a wearable oxygen monitor, in various configurations, illustrating the foldability/flexibility of the assembly, as well as components thereof, according to some embodiments.

In some embodiments, a method of manufacturing an ear-wearable apparatus includes bonding an electronics board to an earpad using at least one of silicone or epoxy such that the electronics board is affixed to the earpad within a cavity defined in a surface of the earpad, and attaching the earpad to a chassis.

Additional details regarding embodiments of the wearable oxygen monitor described herein can be found, by way of example, in Appendices A through D accompanying this disclosure.

Wearable Oxygen Monitor Applications-COVID-19

The novel coronavirus (Coronavirus disease 2019 (COVID-19) is an infectious disease, caused by severe acute respiratory syndrome coronavirus 2 (SARS-CoV-2), that disrupts functions of many organ systems and has resulted in hundreds of thousands of deaths to date. COVID-19 impacts the respiratory system, with effects ranging from mild upper respiratory symptoms to pneumonia and acute respiratory distress syndrome. One potential COVID-19-induced symptom is silent hypoxia, in which a patient experiences below-average (or "low") tissue and blood oxygen saturation, yet does not exhibit breathlessness. Although the mechanisms through which silent hypoxia emerges are unclear, the phenomenon warrants significant clinical and public health attention. Silent hypoxia presents at least two problems, with regard to public health: 1) Infected individuals may progress to more severe disease states yet may be unaware that they are COVID-positive, and 2) Infected, silently hypoxic patients may serve as vectors to infect those around them ("asymptomatic spread"). For hypoxic patients, continuous blood oxygen saturation monitoring is important. As such, there is a desire for smart, portable, and wearable devices that provide real-time SpO2 monitoring and alarm users when their SpO2 levels drop below acceptable levels.

One or more embodiments of the wearable oxygen monitor set forth herein can perform robust blood oxygen saturation level monitoring, for a variety of applications, including: the identification of silently hypoxic patients, helping alert healthcare providers to patients at risk of serious disease progression, augmenting existing COVID-19 diagnostic platforms such as nasopharyngeal swabs, preventing the spread of COVID-19, assisting healthcare providers in the coordination of care, and monitoring one or more of a variety of health conditions detailed below. Normal blood oxygen saturation levels are approximately 95 percent. When a patient exhibits blood oxygen saturation below this threshold, the patient's organ systems, particularly the brain, may receive inadequate oxygen supply, which could lead to confusion or lethargy. If the oxygen level drops below 80 percent, there is risk of serious damage to vital organs, potentially leading to death.

COVID-19 has been reported to induce silent hypoxia in patients. According to Dr. Richard Levitan, an emergency doctor at New York City's Bellevue Hospital, those suffering from COVID-induced silent hypoxia do not experience difficulty breathing until the day they arrive at the hospital. It follows that a subset of COVID-19 patients is entirely asymptomatic despite having COVID-induced hypoxia for a period of time, suggesting that the silently hypoxic patients could spread the infection to others and also progress to more serious COVID-19 stages.

A continuous blood oxygen saturation monitor is desirable, to protect vulnerable members of the population and to facilitate the detection of low blood oxygen saturation as early as possible. High-sensitivity monitoring can help to ensure that patients receive medical assistance before their condition deteriorates, thereby improving patient outcomes and helping the healthcare system manage the current burden of the pandemic.

COVID-19 Symptoms and Risk Factors

Fever, designated by the Centers for Disease Control and Prevention as body temperature above 100.4 degrees Celsius, is the symptom most commonly associated with COVID-19 among the public. However, clinical observational analysis at Northwell Health, the largest provider system in New York, indicates that only 30.7% of patients diagnosed with COVID-19 were febrile upon clinical presentation. The weak correlation between fever and infection suggests that the presentation of COVID-19 is enormously variable, and that providers should screen patients for multiple parameters when assessing the presence or severity of infection.

Although the relationship between febrility and infection is unclear, clinical studies demarcate specific risk factors that can make patient populations more vulnerable to serious infection. According to observations of COVID-19 positive patients at Northwell Health, 56.6% had a history of hypertension, 41.7% had a history of obesity, and 33.8% were diabetic. The strong correlations between chronic pre-existing conditions and COVID-19 hospitalization underscore the desirability of robust monitoring, particularly of high-risk populations.

Clinical observations also suggest the desirability of prognostic markers for COVID-19, which could help ensure that patients are treated earlier and more aggressively, and help in preventing progression to mechanical ventilation, which is associated with significantly higher mortality. In connection with planned reopenings of workplaces and schools, some entities are planning to use thermal scanners to flag febrile individuals. Afebrile individuals, however, may act as vectors for the spread of infection despite not exhibiting this benchmark symptom of COVID-19. More expansive symptom tracking could help to contain the spread of COVID-19.

Risk of COVID-19 Among Elderly and Significance of Hypertension

Individuals older than 65 are overrepresented in the composition of COVID-19 infection, hospitalization, ICU admission, and death. The greater risk COVID-19 that poses to the elderly has greatly contributed to social distancing and the implementation of other public health measures intended to slow the spread of the disease. The strong correlation between hypertension and COVID-19 is believed to play a central role in the overrepresentation of the elderly among infected patients. 63.1% of adults above the age of 60 are hypertensive, and many in this patient population use Angiotensin Converting Enzyme (ACE) inhibitors to lower their blood pressure. Sustained use of ACE inhibitors may serve to increase expression of the ACE-2 receptor in the cardiovascular, renal, gastrointestinal, and pulmonary organ systems. Because SARS-CoV-2 is believed to enter cells through the ACE-2 receptor, the upregulation of ACE-2 in hypertensive patients, who are disproportionately elderly, could serve to increase their disease burden.

COVID-19 and Hospital Transmission for High-Risk Patients

Dr. Shu-Yuan Xiao, a gastroenterologist affiliated with the University of Chicago School of Medicine, studied two patients in Zhongnan hospital in Wuhan, China. The patients, undergoing lung lobectomies for adenocarcinoma, were found to have COVID-19 during the surgery. Pathology reports revealed that both patients had pulmonary edema and inflamed alveoli, both characteristic of pneumonia. At the time of the surgery, neither patient exhibited symptoms of pneumonia, suggesting that patients remained in an early phase of the disease progression. The unexpected cases of pneumonia in a patient population reporting for a surgical procedure for a non-COVID condition illustrates the risk of asymptomatic patients serving as vectors for healthcare providers and other patients in the hospital. To counteract the spread of COVID-19 within healthcare settings, aggressive monitoring of symptoms is desirable, to isolate patients suspected to be positive.

Silent Hypoxia: A Clinical Conundrum

Hypoxemia refers to below-average blood oxygenation, while hypoxia is the clinical state of diminished tissue oxygen tension. Clinically, normal arterial blood oxygen saturation is designated as between 94% and 100%. Reduced blood and tissue oxygenation can disrupt cellular metabolism, growth, and development. Healthcare professionals have traditionally understood hypoxia to be coincident with symptoms of respiratory distress, such as shortness of breath. The clinical presentation of COVID-19, however, partly contradicts this understanding. Dr. Richard Levitan, a volunteer emergency medical provider at Bellevue Hospital in New York, reports cases in which patients, despite having undergone imaging that confirmed viral pneumonia and sub-average blood oxygen saturation, did not report respiratory discomfort for several days before presenting at a hospital. Such cases document a phenomenon referred to as "silent hypoxia." referenced above Classification levels for hypoxemia are presented in the following table:

CLASSIFICATION OF HYPOXEMIA

| Classification | $PaO_2$ (mmhg) | $SaO_2$ (%) |
| --- | --- | --- |
| Normal | 80-100 | >95 |
| Mild Hypoxemia | 60-70 | 90-94 |

-continued

CLASSIFICATION OF HYPOXEMIA

| Classification | $PaO_2$ (mmhg) | $SaO_2$ (%) |
|---|---|---|
| Moderate Hypoxemia | 40-59 | 75-89 |
| Severe Hypoxemia | <40 | <75 |

COVID-19 binds to receptors on alveolar cells, which produce surfactant. Surfactant breaks up the surface tension of water within the alveoli, thereby preventing the alveolar space from collapsing following exhalation. Infection contributes to reduced surfactant production and collapsed air spaces. White blood cells, or leukocytes, mount an inflammatory response within the alveoli. Leukocytes also release cytokines which promote fluid leakage from the pulmonary microvasculature into the space around the alveoli. The buildup of fluid also contributes to the alveolar collapse. Alveolar collapse reduces the interface for oxygen to diffuse into the bloodstream, contributing to hypoxemia. At this stage in disease progression, the lung's compliance may remain unchanged. Consequently, patients may still be able to exhale normal amounts of carbon dioxide, which prevents the onset of breathlessness making them "silently hypoxic." In certain cases, the buildup of fluid and inflammation can progress to a point in which total lung volume decreases, which impedes the clearance of carbon dioxide and results in breathlessness. This transition can be rapid and necessitate ventilatory assistance, which can burden the healthcare system in the aggregate.

COVID-19 and ARDS

Acute respiratory distress syndrome (ARDS) is characterized by the acute development of pulmonary edema, hypoxia, and a subsequent reliance on mechanical ventilation. ARDS is a prominent cause of respiratory failure and was evident in 10% of patients in ICUs prior to the emergence of COVID-19. Unlike cases of silent hypoxia, ARDS is associated with diminished exhalation of carbon dioxide, which contributes to increased shortness of breath. Severe injury to the alveolar cells of the lung contributes to ARDS. Alveolar damage results in an increase in alveolar permeability to fluid—a process that is mediated by inflammatory signals known as cytokines. Disease progression can lead to widespread pulmonary scarring and adverse changes in lung compliance.

ARDS has particular relevance with respect to COVID-19. A retrospective clinical study of 107 patients in Wuhan, China, indicated that 26.2% of all COVID patients had developed ARDS. Among deceased COVID patients, 78.9% had reported ARDS. Another Wuhan clinical study indicates that patients developed ARDS between 8 and 15 days after the onset of illness. The seemingly benign hypoxia in "silent hypoxia" can progress to ARDS, which can be fatal for COVID patients. As such, robust monitoring of blood oxygen saturation can alert patients of hypoxia before the onset of ARDS, potentially improving outcomes and helping providers organize care.

Clinical Management of ARDS

Severe inflammation and fluid accumulation within the lungs of ARDS patients can result in advanced lung fibrosis potentially culminating in total lung collapse. According to the American Thoracic Society, ARDS is associated with a 30-40% mortality rate. Among patients who recover, lung function can gradually recover in a process that can take between six months to a year. Such recovery is only partial, however, as surviving patients will have below-average lung volume and remaining lung fibrosis. According to Dr. Gregory Cosgrove, Chief Medical Officer of the Pulmonary Fibrosis Foundation, patients who survive ARDS can have reduced quality of life which can contribute to anxiety, depression, and/or PTSD. Thus, it is desirable for clinical workflows to include symptom monitoring to rapidly identify patients whose mild COVID-19 symptoms may progress to more severe states such as ARDS.

Clotting and Silent Hypoxia

With increased awareness regarding silent hypoxia in COVID-19 patients, theories have emerged regarding the origin of the phenomenon which seems to contradict medical convention. Dr. Elnara Marcia Negri, a pulmonologist in Sao Paulo, Brazil, emphasizes the role of clotting in inducing a silent hypoxic state in COVID-19 patients. According to Negri, an inflammatory reaction within the pulmonary vasculature may result in subtle increases in blood clot formation in patients with COVID-19. Increased clot formation would interfere with the diffusion of oxygen from the alveoli into the bloodstream, resulting in hypoxia. Negri administered heparin, a common anticoagulant, to patients with hypoxia, regardless of whether they experienced symptoms. According to Negri, 24 of 27 patients have recovered, lending support to her theory. Negri advises patients to routinely monitor their blood oxygen saturation levels, visiting the hospital in the event that their blood oxygen saturation levels dip below 93%.

Hypoxic Strokes in COVID-19

Large-vessel stroke is a condition in which blood flow in one of the major arteries perfusing the brain becomes interrupted. Interrupted blood flow reduces the availability of oxygen in the brain. Physicians affiliated with the Mount Sinai Health System in New York reported five cases of stroke in COVID-19 positive patients below the age of 50 years old. Furthermore, a retrospective study of data from Wuhan indicates that the incidence of stroke among COVID-19 patients was approximately 5%.

Additionally, the average age of COVID-19 patients afflicted with strokes in Wuhan was 55 years, suggesting that COVID-19-related strokes pose a distinctive risk to a slightly younger patient population. Physicians attribute the incidence of strokes in COVID-19 patients to the role the infection plays in inducing dysfunction in endothelial cells, which line the interior of blood vessels. The association of COVID-19 with other serious pathologies, such as large-vessel strokes, underscores the desirability of robust monitoring of blood oxygen saturation.

Shortcomings in Known COVID-19 Diagnostic Technology

Cleveland Clinic researchers have investigated the efficacy of existing diagnostic technology used to identify patients who are positive for COVID-19. These diagnostic tests include Abbott's ID NOW machine, which has been said to produce results in under 15 minutes. According to the study, the ID NOW had a false-negative rate of 14.8% and a true positive rate of 85.2%. The study's results suggest that approximately 15% of positive patients would falsely be labeled as being uninfected with the ID NOW test. The study also investigated the DiaSorin Simplexa test, which had a true-positive rate of 89.3%. According to Dr. Gary Procop, head of COVID-19 testing at the Cleveland Clinic, diagnostic tests should have true-positive rates of at least 95% to assure the public of the test's efficacy. Although diagnostic platforms made by Roche and Cepheid had accuracy rates above 95%, the subthreshold accuracy of the DiaSorin Simplexa and ID NOW platforms suggest that there are lingering inadequacies within areas of diagnostics for COVID-19. The challenges within COVID-19 testing render the monitoring of other clinical variables, like blood oxygen saturation, even more important. It is possible that robust oxygen monitoring could be used to supplement traditional nasopharyngeal swab tests to yield an even higher accuracy of COVID-19 diagnosis, quickly identifying patients who need medical assistance.

Known Monitoring Solutions to Combat Silent Hypoxia—Pulse Oximetry

Given the possibility that a patient may experience severe hypoxia prior to the onset of breathlessness, some medical providers have called for widespread pulse oximetry. Pulse oximetry can provide patients with a non-invasive way to monitor their blood oxygen saturation levels, alarming them of hypoxia even if they report no other symptoms. A pulse oximeter includes a light emitting sensor that can be clipped to a patient's finger. Patients using at-home pulse oximeters may consult their medical providers, facilitating proper interpretation of blood oxygen saturation levels. Dr. Levitan, an emergency medical physician at Bellevue hospital who noted cases of silent hypoxia, has called for all COVID-19 positive patients to routinely check their blood oxygen saturation levels within the two weeks following diagnosis. Oxygenation monitoring for patients that have not been diagnosed, yet have symptoms of cough, fatigue, and/or fever, may also be prudent Known pulse oximeters, such as finger clips, can be useful for patient assessment, but are often difficult to transport and/or use. Some pulse oximeters, such as the Nonin Onyx, are bulky and can fall off during patient transport or as a result of routine daily movements such as getting up, sitting down, and wiggling one's fingers. In addition, some patients may have a weak pulse or tissue damage, which can skew measurement results. Other known wearable devices provide measurements only at the wrist, and such devices typically do not provide oxygen monitoring or associated warnings. Rather, such devices measure pulse and fitness-related measurements such as step count and sleep time.

In the case of COVID-19, the pulse oximeter finger cuff typically does not provide and/or is not used for continuous monitoring. In cases of silent hypoxia, when patients do not feel any respiratory distress, it may not occur to patients to check their blood oxygen saturation levels, and be unaware of their hypoxia for extended periods of time.

As discussed above, blood oxygen saturation is a valuable biomarker of COVID-19, both for symptomatic and asymptomatic individuals. Embodiments of the wearable oxygen monitor set forth herein facilitate the continuous monitoring of blood oxygen saturation levels, via measurements taken on a wearer's ear (e.g., the helix, scapha, pinna, etc.), with relevant measurement data displayed via a mobile software application. When the wearer's SpO2 levels drop below acceptable levels, an alarm is generated and communicated to the wearer (e.g., via one or more of: an audio indication, a light indication, a GUI display, etc.). In addition, the wearer can trigger a call to emergency services by clicking a button on the wearable oxygen monitor.

All combinations of the foregoing concepts and additional concepts discussed here within (provided such concepts are not mutually inconsistent) are contemplated as being part of the subject matter disclosed herein. The terminology explicitly employed herein that also may appear in any disclosure incorporated by reference should be accorded a meaning most consistent with the particular concepts disclosed herein.

The drawings are primarily for illustrative purposes, and are not intended to limit the scope of the subject matter described herein. The drawings are not necessarily to scale; in some instances, various aspects of the subject matter disclosed herein may be shown exaggerated or enlarged in the drawings to facilitate an understanding of different features. In the drawings, like reference characters generally refer to like features (e.g., functionally similar and/or structurally similar elements).

The entirety of this application (including the Cover Page, Title, Headings, Background, Summary, Brief Description of the Drawings, Detailed Description, Embodiments, Abstract, Figures, Appendices, and otherwise) shows, by way of illustration, various embodiments in which the embodiments may be practiced. The advantages and features of the application are of a representative sample of embodiments only, and are not exhaustive and/or exclusive. Rather, they are presented to assist in understanding and teach the embodiments, and are not representative of all embodiments. As such, certain aspects of the disclosure have not been discussed herein. That alternate embodiments may not have been presented for a specific portion of the innovations or that further undescribed alternate embodiments may be available for a portion is not to be considered to exclude such alternate embodiments from the scope of the disclosure. It will be appreciated that many of those undescribed embodiments incorporate the same principles of the innovations and others are equivalent. Thus, it is to be understood that other embodiments may be utilized and functional, logical, operational, organizational, structural and/or topological modifications may be made without departing from the scope and/or spirit of the disclosure. As such, all examples and/or embodiments are deemed to be non-limiting throughout this disclosure.

Also, no inference should be drawn regarding those embodiments discussed herein relative to those not discussed herein other than it is as such for purposes of reducing space and repetition. For instance, it is to be understood that the logical and/or topological structure of any combination of any program components (a component collection), other components and/or any present feature sets as described in the figures and/or throughout are not limited to a fixed operating order and/or arrangement, but rather, any disclosed order is exemplary and all equivalents, regardless of order, are contemplated by the disclosure.

The term "automatically" is used herein to modify actions that occur without direct input or prompting by an external source such as a user. Automatically occurring actions can occur periodically, sporadically, in response to a detected event (e.g., a user logging in), or according to a predetermined schedule.

As used herein, the term "substantially" has a meaning similar to "mostly" or "to a great extent." For example, the phrase "a substantially uniform thickness" refers to a thickness value plus or minus a range of 10%.

The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

The term "processor" should be interpreted broadly to encompass a general purpose processor, a central processing unit (CPU), a microprocessor, a digital signal processor (DSP), a controller, a microcontroller, a state machine and so forth. Under some circumstances, a "processor" may refer to an application specific integrated circuit (ASIC), a programmable logic device (PLD), a field programmable gate array (FPGA), etc. The term "processor" may refer to a combination of processing devices, e.g., a combination of a DSP and a microprocessor, a plurality of microprocessors, one or more microprocessors in conjunction with a DSP core or any other such configuration.

The term "memory" should be interpreted broadly to encompass any electronic component capable of storing electronic information. The term memory may refer to various types of processor-readable media such as random access memory (RAM), read-only memory (ROM), non-volatile random access memory (NVRAM), programmable read-only memory (PROM), erasable programmable read only memory (EPROM), electrically erasable PROM (EEPROM), flash memory, magnetic or optical data storage, registers, etc. Memory is said to be in electronic communication with a processor if the processor can read information from and/or write information to the memory. Memory that is integral to a processor is in electronic communication with the processor.

The terms "instructions" and "code" should be interpreted broadly to include any type of computer-readable statement(s). For example, the terms "instructions" and "code" may refer to one or more programs, routines, sub-routines, functions, procedures, etc. "Instructions" and "code" may comprise a single computer-readable statement or many computer-readable statements.

Some embodiments described herein relate to a computer storage product with a non-transitory computer-readable medium (also can be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) may be those designed and constructed for the specific purpose or purposes. Examples of non-transitory computer-readable media include, but are not limited to, magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices. Other embodiments described herein relate to a computer program product, which can include, for example, the instructions and/or computer code discussed herein.

Some embodiments and/or methods described herein can be performed by software (executed on hardware), hardware, or a combination thereof. Hardware modules may include, for example, a general-purpose processor, a field programmable gate array (FPGA), and/or an application specific integrated circuit (ASIC). Software modules (executed on hardware) can be expressed in a variety of software languages (e.g., computer code), including C, C++, Java™, Ruby, Visual Basic™, and/or other object-oriented, procedural, or other programming language and development tools. Examples of computer code include, but are not limited to, micro-code or micro-instructions, machine instructions, such as produced by a compiler, code used to produce a web service, and files including higher-level instructions that are executed by a computer using an interpreter. For example, embodiments may be implemented using imperative programming languages (e.g., C, Fortran, etc.), functional programming languages (Haskell, Erlang, etc.), logical programming languages (e.g., Prolog), object-oriented programming languages (e.g., Java, C++, etc.) or other suitable programming languages and/or development tools. Additional examples of computer code include, but are not limited to, control signals, encrypted code, and compressed code.

Various concepts may be embodied as one or more methods, of which at least one example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments. Put differently, it is to be understood that such features may not necessarily be limited to a particular order of execution, but rather, any number of threads, processes, services, servers, and/or the like that may execute serially, asynchronously, concurrently, in parallel, simultaneously, synchronously, and/or the like in a manner consistent with the disclosure. As such, some of these features may be mutually contradictory, in that they cannot be simultaneously present in a single embodiment. Similarly, some features are applicable to one aspect of the innovations, and inapplicable to others.

In addition, the disclosure may include other innovations not presently described. Applicant reserves all rights in such innovations, including the right to embodiment such innovations, file additional applications, continuations, continuations-in-part, divisionals, and/or the like thereof. As such, it should be understood that advantages, embodiments, examples, functional, features, logical, operational, organizational, structural, topological, and/or other aspects of the disclosure are not to be considered limitations on the disclosure as defined by the embodiments or limitations on equivalents to the embodiments. Depending on the particular desires and/or characteristics of an individual and/or enterprise user, database configuration and/or relational model, data type, data transmission and/or network framework, syntax structure, and/or the like, various embodiments of the technology disclosed herein may be implemented in a manner that enables a great deal of flexibility and customization as described herein.

All definitions, as defined and used herein, should be understood to control over dictionary definitions, definitions in documents incorporated by reference, and/or ordinary meanings of the defined terms.

As used herein, in particular embodiments, the terms "about" or "approximately" when preceding a numerical value indicates the value plus or minus a range of 10%. Where a range of values is provided, it is understood that each intervening value, to the tenth of the unit of the lower limit unless the context clearly dictates otherwise, between the upper and lower limit of that range and any other stated or intervening value in that stated range is encompassed within the disclosure. That the upper and lower limits of these smaller ranges can independently be included in the smaller ranges is also encompassed within the disclosure, subject to any specifically excluded limit in the stated range. Where the stated range includes one or both of the limits, ranges excluding either or both of those included limits are also included in the disclosure.

The indefinite articles "a" and "an," as used herein in the specification and in the embodiments, unless clearly indicated to the contrary, should be understood to mean "at least one."

The phrase "and/or," as used herein in the specification and in the embodiments, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the embodiments, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the embodiments, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the embodiments, shall have its ordinary meaning as used in the field of patent law.

As used herein in the specification and in the embodiments, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the embodiments, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. A kit, comprising:

a wearable device configured to be positioned on an ear of a wearer, the wearable device including a first body portion, a second body portion, and a connection member mechanically coupled to each of the first body portion and the second body portion, the first body portion having a processor, a memory operably coupled to the processor, at least one light-emitting diode, and at least one optical sensor configured to detect, during operation, a reflected portion of light emitted from the at least one light-emitting diode, the reflected portion of light being reflected from a surface of the ear of the wearer, the memory storing instructions to cause the processor to calculate a blood oxygen saturation level of the wearer based on the reflected portion of light;

a charger case configured to contain and supply power to the wearable device; and a plurality of flexible earpads, each flexible earpad from the plurality of flexible earpads configured to be mechanically coupled to the second body portion.

2. The kit of claim 1, wherein the second body portion includes an annular opening, and each flexible earpad from the plurality of flexible earpads is configured to be mechanically coupled to the second body portion via the annular opening.

3. The kit of claim 1, wherein the wearable device and the charger case are configured such that data can be exchanged between the wearable device and the charger case.

4. The kit of claim 1, wherein the wearable device and the charger case are configured such that at least one of data or power can be exchanged between the wearable device and the charger case via a plurality of electrical contacts.

5. The kit of claim 1, wherein the wearable device further includes a haptic actuator operatively coupled to the processor, the memory further storing instructions to operate the haptic actuator in response to detecting an event.

6. The kit of claim 5, wherein the event includes at least one of:

an alarm condition;

a low battery condition; or a successful positioning of the wearable device on the ear of the wearer.

7. The kit of claim 1, wherein the connection member includes nylon.

8. The kit of claim 1, wherein the connection member includes plastic.

9. The kit of claim 1, wherein the at least one optical sensor is secured within a cavity of the first body portion by an epoxy.

10. The kit of claim 1, wherein the processor and the memory are positioned on a circuit board, and the at least one optical sensor is electrically coupled to the circuit board via a flexible conductor.

11. The kit of claim 10, wherein the flexible conductor is substantially S-shaped.

12. The kit of claim 1, wherein the wearable device further includes at least one of a microphone or a speaker operatively coupled to the processor, the memory further storing instructions to cause the processor to activate the at least one of the microphone or the speaker in response to detecting an alarm condition.

13. The kit of claim 1, wherein the wearable device further includes a wireless transceiver, operatively coupled to the processor and configured to communicate with a mobile software application, the memory further storing instructions to cause the processor to send signals representing measurement data to the mobile software application via the wireless transceiver.

14. The kit of claim 1, wherein the memory further stores instructions to cause the processor to send signals, according to a predetermined schedule, to a mobile software application, the signals representing measurement data.

15. The kit of claim 1, wherein the wearable device further includes at least one additional sensor operatively coupled to the processor, the at least one additional sensor including at least one of: a body temperature sensor, an air quality sensor, a humidity sensor, an altimeter, or a barometric pressure sensor, the memory further storing instructions to cause the processor to at least one of: (1) store, in the memory, data collected by the at least one additional sensor, or (2) send signals, according to a predefined schedule, to a mobile software application, the signals representing data collected by the at least one additional sensor.

16. The kit of claim 1, wherein the second body portion does not include any electronic components.

17. The kit of claim 1, wherein the wearable device is waterproof.

18. The kit of claim 1, wherein the memory further stores instructions to generate and send a signal representing an alert in response to detecting a user interaction with an alert actuator.

19. The kit of claim 1, wherein the memory further stores instructions to initiate a predefined emergency plan in response to detecting a user interaction with an alert mechanism.

20. The kit of claim 1, wherein the memory further stores instructions to initiate a telephone call in response to detecting a user interaction with an alert mechanism.

* * * * *